United States Patent
Pitera et al.

(10) Patent No.: US 8,114,645 B2
(45) Date of Patent: Feb. 14, 2012

(54) METHODS FOR INCREASING ISOPRENOID AND ISOPRENOID PRECURSOR PRODUCTION BY MODULATING FATTY ACID LEVELS

(75) Inventors: Douglas J. Pitera, Oakland, CA (US); Jack D. Newman, San Francisco, CA (US); Jeffrey Lance Kizer, San Francisco, CA (US); Jay D. Keasling, Berkeley, CA (US); Brian F. Pfleger, Ann Arbor, MI (US)

(73) Assignee: The Regents of the University of California, Oakland, CA (US)

( * ) Notice: Subject to any disclaimer, the term of this patent is extended or adjusted under 35 U.S.C. 154(b) by 286 days.

(21) Appl. No.: 12/299,004

(22) PCT Filed: May 17, 2007

(86) PCT No.: PCT/US2007/012111
§ 371 (c)(1),
(2), (4) Date: Mar. 23, 2009

(87) PCT Pub. No.: WO2007/136847
PCT Pub. Date: Nov. 29, 2007

(65) Prior Publication Data
US 2010/0055754 A1    Mar. 4, 2010

Related U.S. Application Data

(60) Provisional application No. 60/802,266, filed on May 19, 2006.

(51) Int. Cl.
*C12N 1/00* (2006.01)
*C12N 1/21* (2006.01)
*C12P 7/64* (2006.01)

(52) U.S. Cl. ............ 435/167; 435/243; 435/44; 435/252

(58) Field of Classification Search ................. None
See application file for complete search history.

(56) References Cited

U.S. PATENT DOCUMENTS

| 5,460,949 | A | 10/1995 | Saunders et al. | |
| 6,531,303 | B1 | 3/2003 | Millis et al. | |
| 6,689,593 | B2 | 2/2004 | Millis et al. | |
| 7,129,392 | B2 * | 10/2006 | Hahn et al. | 800/282 |
| 7,172,886 | B2 | 2/2007 | Keasling et al. | |
| 7,183,089 | B2 | 2/2007 | Keasling et al. | |
| 7,192,751 | B2 | 3/2007 | Keasling et al. | |
| 2003/0148416 | A1 * | 8/2003 | Berry et al. | 435/67 |
| 2004/0005678 | A1 * | 1/2004 | Keasling et al. | 435/146 |
| 2004/0029239 | A1 | 2/2004 | Ohto et al. | |
| 2004/0063182 | A1 | 4/2004 | Ohto et al. | |
| 2004/0072323 | A1 | 4/2004 | Matsuda et al. | |
| 2004/0077068 | A1 | 4/2004 | Brzostowicz et al. | |
| 2004/0110257 | A1 | 6/2004 | Millis et al. | |

OTHER PUBLICATIONS

Martin et al. Engineering a Me~,alonate Pathway in *Escherichia coli* for Production of Terpenoids. Nature Biotechnology, Jul. 2003, vol. 21, No. 7, pp. 796-802.*
Takagi et al. (J. Bacteriol. Aug. 2000; 182(15):4153-7.*
Martin et al. Engineering a mevalonate pathway in *Escherichia coli* for production of terpenoids. (2003) Nat. Biotech. 21(7):796-802.
Pitera et al. Balancing a heterologous mevalonate pathway for improved isoprenoid production in *Escherichia coli*. Metabolic Engineering, 2007, col. 9, 193-207.

* cited by examiner

*Primary Examiner* — Kagnew H Gebreyesus
(74) *Attorney, Agent, or Firm* — Paula A. Borden; Bozicevic Field & Francis LLP

(57) ABSTRACT

The present invention provides methods of increasing production of an isoprenoid or an isoprenoid precursor in a host cell, the methods generally involving modulating the level of activity of a fatty acid biosynthetic pathway enzyme in the host cell and/or culturing the host cell in a culture medium comprising a fatty acid or a compound that can be metabolized in a cell or broken down in the medium to yield a fatty acid and/or culturing the host cell in a culture medium having increased osmolarity.

11 Claims, 25 Drawing Sheets

FIG. 4A

GenBank AE014075
*E. coli* malonyl-CoA:ACP transacylase

```
  1  atgacgcaatttgcatttgtgttccctggacagggttctcaaaccgttggaatgctggct
 61  gatatggcggcgagctatccaattgtcgaagaaacgtttgcagaagcttctgcggcgctg
121  ggctacgatctgtgggcgctgacccagcagggccagctgaagaactgaataaaacctgg
181  caaactcagccagcgctgttgactgcatctgttgcgctgtatcgcgtatggcagcagcag
241  ggcggtaaagcaccggcaatgatggccggtcacagcctggggaatactccgcgctggtt
301  tgcgctggtgtaattgatttcgctgatgcggtgcgtttggttgagatgcgcggcaagttc
361  atgcaagaagccgtaccggaaggcacgggcgctatggcggcaatcatcggtctggatgat
421  gcgtctattgcgaaagcgtgtgaagaagctgcagaaggtcaggtcgtttctccggtaaac
481  tttaactctccgggacaggtggttattgccggtcataagaagcagttgagcgtgctggc
541  gctgcctgtaaagctgcgggcgcaaaacgcgctctgccgttaccagtgagcgtaccgtct
601  cactgtgcgctgatgaaaccagcagccgacaaactggcagtagaattagcgaaaatcacc
661  tttaacgcaccaacagttcctgttgtgaataacgttgatgtgaaatgcgaaaccaatggt
721  gatgccatccgtgacgcactggtacgtcagttgtataaccggttcagtggacgaagtct
781  gttgagtacatggcagcgcaaggcgtagaacatctctatgaagtcggcccgggcaaagtg
841  cttactggcctgacgaaacgcattgtcgacaccctgaccgcctcggcgctgaacgaacct
901  tcagcgatggcagcggcgctcgagctttaa (SEQ ID NO:1)
```

FIG. 4B

GenBank AAN79832.1
*E. coli* malonyl-CoA:ACP transacylase

```
MTQFAFVFPGQGSQTVGMLADMAASYPIVEETFAEASAALGYDL
WALTQQGPAEELNKTWQTQPALLTASVALYRVWQQQGGKAPAMMAGHSLGEYSALVCA
GVIDFADAVRLVEMRGKFMQEAVPEGTGAMAAIIGLDDASIAKACEEAAEGQVVSPVN
FNSPGQVVIAGHKEAVERAGAACKAAGAKRALPLPVSVPSHCALMKPAADKLAVELAK
ITFNAPTVPVVNNVDVKCETNGDAIRDALVRQLYNPVQWTKSVEYMAAQGVEHLYEVG
PGKVLTGLTKRIVDTLTASALNEPSAMAAALEL (SEQ ID NO:2)
```

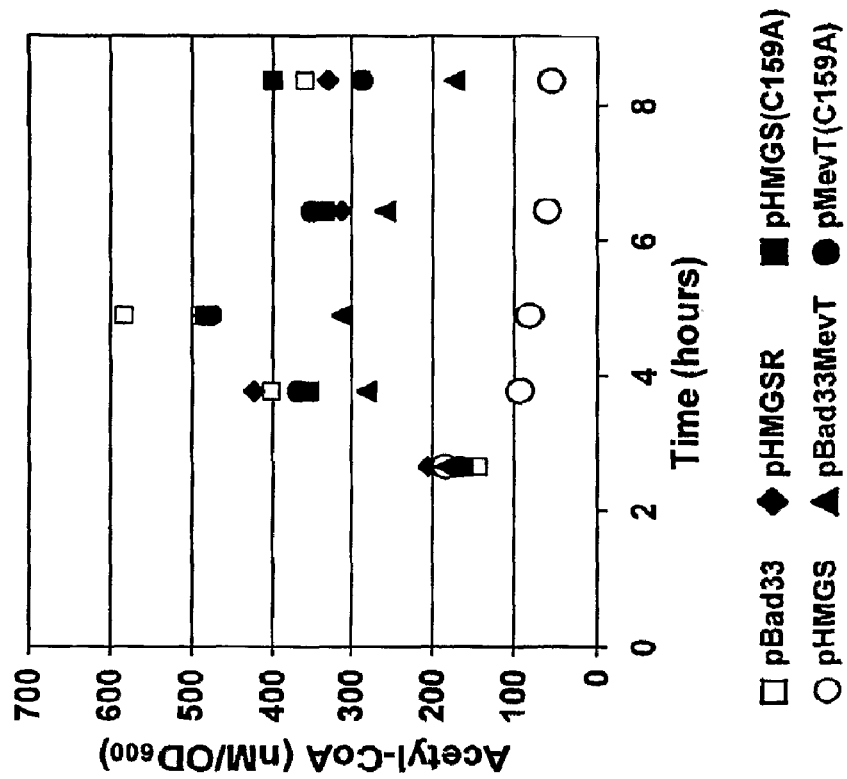
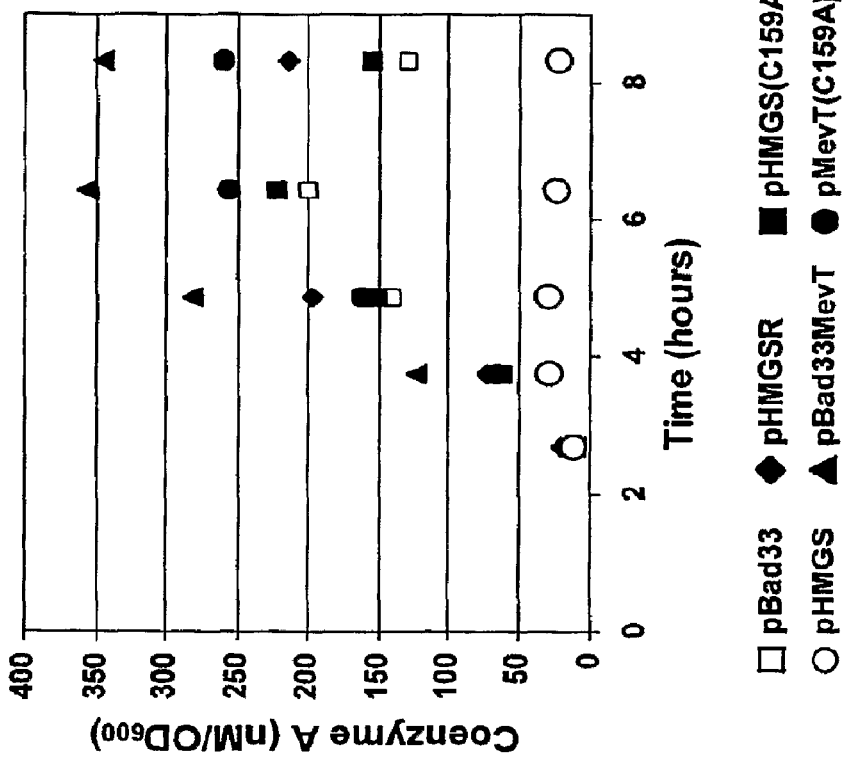
FIG. 6A
FIG. 6B

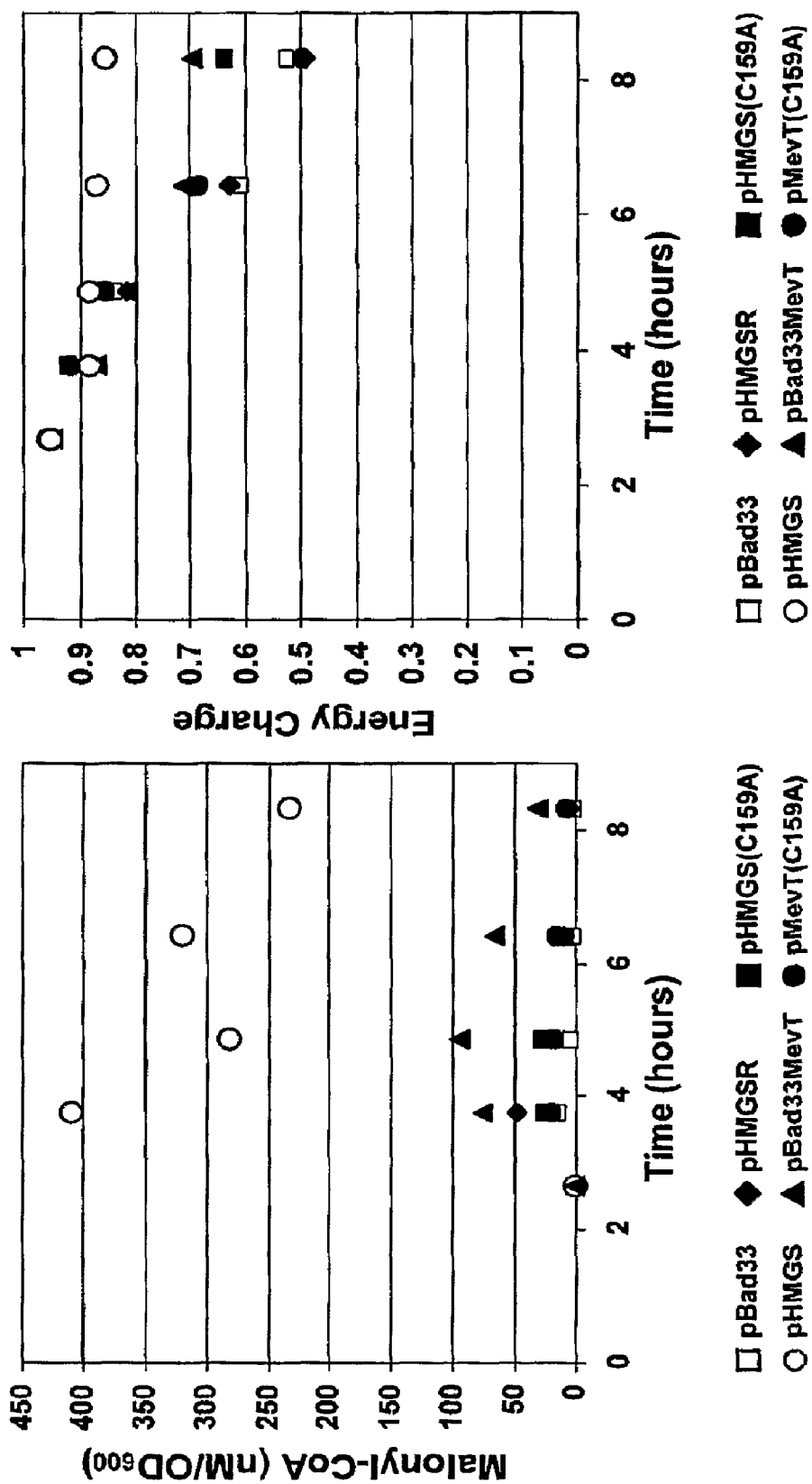

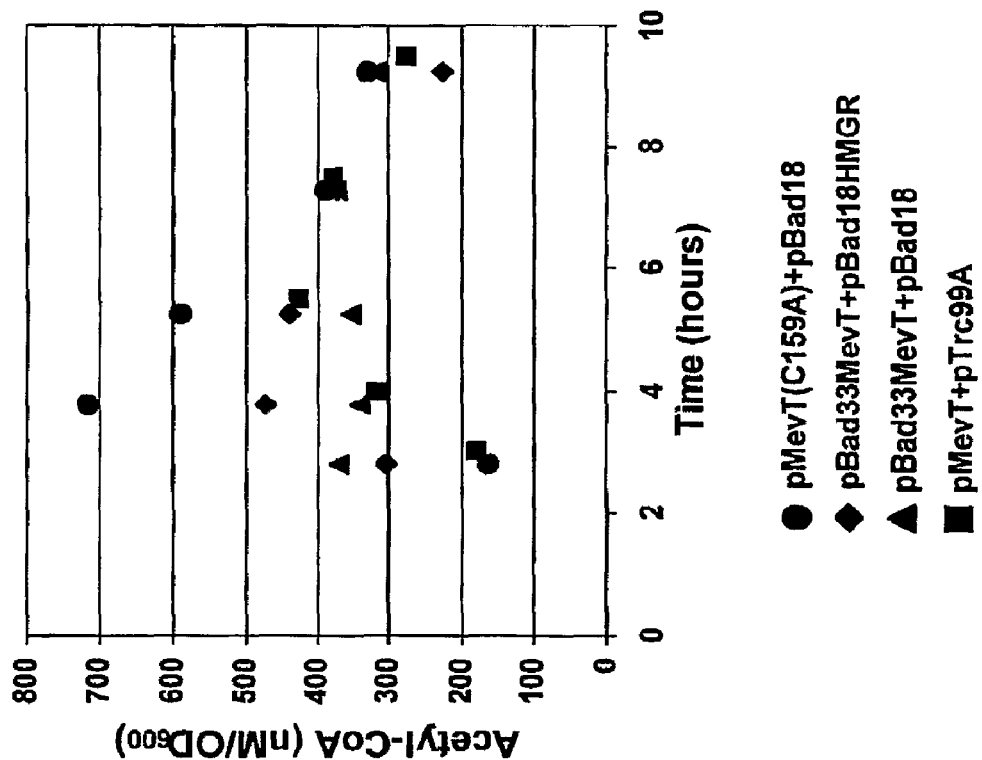
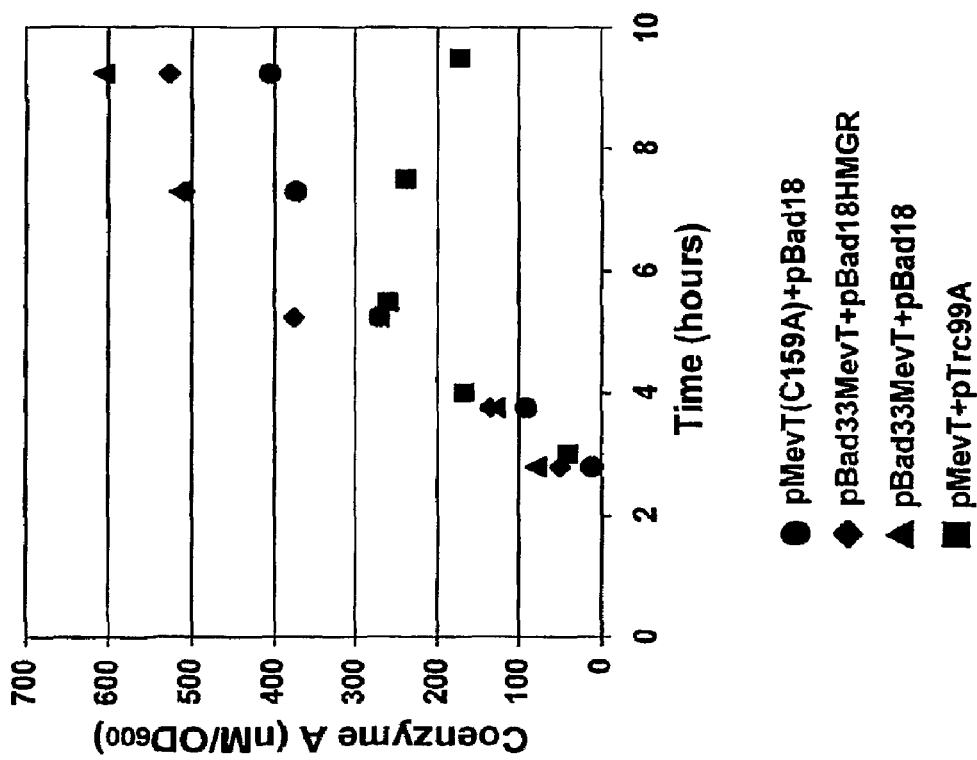

FIG. 9

Oxidative Stress

| MevT | 1 hr | 3 hr |
|---|---|---|
| dps | 2.9 (3.1) | 4.1 (4.0) |
| sufA | 2.1 (3.1) | 3.6 (4.0) |
| poxB | 1.8 (2.6) | 2.2 (3.8) |
| ahpC | 1.9 (2.5) | 2.6 (2.0) |
| ynhC | 1.7 (3.2) | 3.1 (3.5) |
| sufB | 1.4 (2.4) | 3.2 (3.3) |
| katE | 1.2 (2.6) | 3.0 (3.6) |
| sufD | 1.8 (2.9) | 2.9 (3.7) |
| sufC | 2.1 (2.3) | 2.4 (3.2) |

| MevT vs MevT-C159A | 1 hr | 3 hr |
|---|---|---|
| katE | ND | 3.8 (3.2) |
| katG | 2.6 (2.8) | 3.8 (3.1) |
| dps | 2.2 (3.1) | 3.2 (12.1) |
| sufA | 1.6 (2.1) | 2.4 (4.7) |
| sufB | 1.6 (2.2) | 2.4 (6.5) |
| sufC | 1.7 (2.2) | 2.2 (4.0) |
| sufD | 1.9 (2.2) | 2.1 (3.7) |

| MevT-C159A | 1 hr | 3 hr |
|---|---|---|
| dps | 1.4 (1.1) | 2.1 (2.3) |
| soxS | 1.4 (1.2) | 2.4 (1.9) |
| sodB | 1.6 (1.5) | 2.2 (1.5) |

Osmotic Stress

| MevT | 1 hr | 3 hr |
|---|---|---|
| osmC | 3.3 (4.2) | 5.5 (6.0) |
| osmY | 2.9 (3.8) | 6.6 (6.3) |
| osmE | 2.4 (3.8) | 3.0 (4.5) |
| otsA | 1.8 (2.4) | 3.9 (5.2) |
| betA | 1.5 (2.0) | 2.8 (4.1) |
| otsB | 1.9 (2.4) | 2.9 (4.1) |
| betB | 1.7 (2.1) | 2.5 (3.5) |
| proP | 1.6 (1.6) | 2.1 (2.8) |

| MevT vs MevT-C159A | 1 hr | 3 hr |
|---|---|---|
| otsB | 1.3 (4.2) | 5.3 (4.9) |
| otsA | 1.2 (2.5) | 5.3 (4.5) |
| osmC | 3.2 (4.1) | 4.6 (3.5) |
| osmY | 2.3 (4.6) | 3.6 (5.8) |
| betA | 1.3 (2.7) | 3.2 (3.7) |
| osmB | 0.9 (2.8) | 3.2 (3.0) |
| betB | 1.6 (2.7) | 2.4 (2.8) |
| osmE | 1.3 (2.2) | 2.1 (3.3) |
| proP | 1.4 (2.3) | 1.9 (3.3) |
| betT | 0.8 (2.0) | 1.5 (2.7) |
| kdpA | 1.2 (1.8) | 1.9 (2.8) |

Heat Shock

| MevT | 1 hr | 3 hr |
|---|---|---|
| clpB | 8.4 (5.5) | 2.9 (3.2) |
| ibpB | 6.6 (6.6) | 2.5 (3.3) |
| ibpA | 5.6 (5.2) | 3.7 (4.2) |
| dnaK | 5.1 (6.0) | 2.6 (2.0) |
| groS | 3.1 (4.6) | 2.8 (2.1) |
| grpE | 3.0 (3.1) | 1.3 (0.9) |
| hslV | 2.9 (3.1) | 2.3 (2.5) |
| htpG | 2.8 (3.6) | 1.4 (1.4) |
| groL | 2.3 (2.7) | 1.7 (1.2) |
| clpA | 2.2 (2.4) | 1.4 (1.2) |
| dnaJ | 2.1 (2.2) | 1.6 (1.5) |
| hslU | 2.0 (2.3) | 1.4 (1.1) |
| lon | 1.9 (2.0) | 1.9 (2.0) |

| MevT vs MevT-C159A | 1 hr | 3 hr |
|---|---|---|
| clpB | 2.5 (6.8) | 0.4 (-2.3) |
| ibpB | 2.5 (5.8) | 0.5 (-4.3) |
| ibpA | 1.7 (2.3) | 0.3 (-4.6) |
| grpE | 0.8 (1.1) | 0.4 (-3.3) |
| hchA | 2.4 (3.5) | ND |
| pphA | 2.2 (4.0) | ND |
| dnaK | 2.0 (5.6) | 0.7 (-2.1) |
| htpG | 2.0 (3.2) | 0.7 (-2.0) |
| groS | 1.1 (1.4) | 0.5 (-2.9) |
| groL | 0.8 (-1.0) | 0.3 (-3.1) |

| MevT-C159A | 1 hr | 3 hr |
|---|---|---|
| ibpB | 5.3 (9.2) | 37.9 (6.1) |
| clpB | 9.4 (6.8) | 22.5 (7.9) |
| ibpA | 5.7 (6.9) | 42.1 (6.2) |
| grpE | 5.3 (4.3) | 5.0 (5.9) |
| dnaK | 6.4 (5.3) | 6.0 (6.8) |
| htpG | 3.4 (3.3) | 3.3 (4.4) |
| groS | 4.1 (1.7) | 4.4 (5.4) |
| hslU | 3.2 (2.5) | 2.7 (4.1) |
| groL | 3.4 (1.8) | 3.8 (4.1) |
| hslV | 2.7 (1.8) | 2.1 (3.5) |
| dnaJ | 2.2 (2.2) | 2.6 (2.8) |
| clpA | 1.7 (2.8) | 2.8 (1.9) |
| htpX | 1.8 (2.5) | 2.5 (2.2) |
| lon | 2.2 (1.8) | 2.1 (2.6) |
| gapA | 1.9 (1.1) | 2.5 (2.7) |
| clpP | 1.5 (1.9) | 2.1 (1.6) |

SEQUENCE LISTING

```
<160> NUMBER OF SEQ ID NOS: 4

<210> SEQ ID NO 1
<211> LENGTH: 930
<212> TYPE: DNA
<213> ORGANISM: Escherichia coli

<400> SEQUENCE: 1
atgacgcaat ttgcatttgt gttccctgga cagggttctc aaaccgttgg aatgctggct      60
gatatggcgg cgagctatcc aattgtcgaa gaaacgtttg cagaagcttc tgcggcgctg     120
ggctacgatc tgtgggcgct gacccagcag gggccagctg aagaactgaa taaaacctgg     180
caaactcagc cagcgctgtt gactgcatct gttgcgctgt atcgcgtatg gcagcagcag     240
ggcggtaaag caccggcaat gatggccggt cacagcctgg gggaatactc cgcgctggtt     300
```

```
tgcgctggtg taattgattt cgctgatgcg gtgcgtttgg ttgagatgcg cggcaagttc    360
atgcaagaag ccgtaccgga aggcacgggc gctatggcgg caatcatcgg tctggatgat    420
gcgtctattg cgaaagcgtg tgaagaagct gcagaaggtc aggtcgtttc tccggtaaac    480
tttaactctc cgggacaggt ggttattgcc ggtcataaag aagcagttga gcgtgctggc    540
gctgcctgta agctgcgggc gcaaaacgc gctctgccgt taccagtgag cgtaccgtct    600
cactgtgcgc tgatgaaacc agcagccgac aaactggcag tagaattagc gaaaatcacc    660
tttaacgcac caacagttcc tgttgtgaat aacgttgatg tgaaatgcga accaatggt     720
gatgccatcc gtgacgcact ggtacgtcag ttgtataacc cggttcagtg gacgaagtct    780
gttgagtaca tggcagcgca aggcgtagaa catctctatg aagtcggccc gggcaaagtg    840
cttactggcc tgacgaaacg cattgtcgac accctgaccg cctcggcgct gaacgaacct    900
tcagcgatgg cagcggcgct cgagctttaa                                     930
```

<210> SEQ ID NO 2
<211> LENGTH: 309
<212> TYPE: PRT
<213> ORGANISM: Escherichia coli

<400> SEQUENCE: 2

```
Met Thr Gln Phe Ala Phe Val Phe Pro Gly Gln Gly Ser Gln Thr Val
 1               5                  10                  15
Gly Met Leu Ala Asp Met Ala Ala Ser Tyr Pro Ile Val Glu Glu Thr
             20                  25                  30
Phe Ala Glu Ala Ser Ala Ala Leu Gly Tyr Asp Leu Trp Ala Leu Thr
         35                  40                  45
Gln Gln Gly Pro Ala Glu Glu Leu Asn Lys Thr Trp Gln Thr Gln Pro
     50                  55                  60
Ala Leu Leu Thr Ala Ser Val Ala Leu Tyr Arg Val Trp Gln Gln Gln
 65                  70                  75                  80
Gly Gly Lys Ala Pro Ala Met Met Ala Gly His Ser Leu Gly Glu Tyr
                 85                  90                  95
Ser Ala Leu Val Cys Ala Gly Val Ile Asp Phe Ala Asp Ala Val Arg
            100                 105                 110
Leu Val Glu Met Arg Gly Lys Phe Met Gln Glu Ala Val Pro Glu Gly
        115                 120                 125
Thr Gly Ala Met Ala Ala Ile Ile Gly Leu Asp Asp Ala Ser Ile Ala
    130                 135                 140
Lys Ala Cys Glu Glu Ala Ala Glu Gly Gln Val Val Ser Pro Val Asn
145                 150                 155                 160
Phe Asn Ser Pro Gly Gln Val Val Ile Ala Gly His Lys Glu Ala Val
                165                 170                 175
Glu Arg Ala Gly Ala Ala Cys Lys Ala Ala Gly Ala Lys Arg Ala Leu
            180                 185                 190
Pro Leu Pro Val Ser Val Pro Ser His Cys Ala Leu Met Lys Pro Ala
        195                 200                 205
Ala Asp Lys Leu Ala Val Glu Leu Ala Lys Ile Thr Phe Asn Ala Pro
    210                 215                 220
Thr Val Pro Val Val Asn Asn Val Asp Val Lys Cys Glu Thr Asn Gly
225                 230                 235                 240
Asp Ala Ile Arg Asp Ala Leu Val Arg Gln Leu Tyr Asn Pro Val Gln
                245                 250                 255
Trp Thr Lys Ser Val Glu Tyr Met Ala Ala Gln Gly Val Glu His Leu
            260                 265                 270
```

```
Tyr Glu Val Gly Pro Gly Lys Val Leu Thr Gly Leu Thr Lys Arg Ile
        275                 280                 285

Val Asp Thr Leu Thr Ala Ser Ala Leu Asn Glu Pro Ser Ala Met Ala
    290                 295                 300

Ala Ala Leu Glu Leu
305

<210> SEQ ID NO 3
<211> LENGTH: 1750
<212> TYPE: DNA
<213> ORGANISM: Escherichia coli

<400> SEQUENCE: 3
gctcgtcaaa atctcggaaa caggtgtacc ctcagcatta aattcgaggt tggcaggttg      60
tatggagtag tgtttcacgt aagttactcg tcttacaggc ggtggctcga tcttagcgat     120
gtgtgtaagg ctgcgcaaat ttctctatta aatggctgat cggacttgtt cggcgtacaa     180
gtgtacgcta ttgtgcattc gaaacttact ctatgtgcga cttacagagg tattgaatga     240
aacgtgcagt gattactggc ctgggcattg tttccagcat cggtaataac cagcaggaag     300
tcctggcatc tctgcgtgaa ggacgttcag ggatcacttt ctctcaggag ctgaaggatt     360
ccggcatgcg tagccacgtc tggggcaacg taaaactgga taccactggc ctcattgacc     420
gcaaagttgt gcgctttatg agcgacgcat ccatttatgc attcctttct atggagcagg     480
caatcgctga tgcgggcctc tctccggaag cttaccagaa taccccgcgc gttggcctga     540
ttgcaggttc cggcggcggc tccccgcgtt tccaggtgtt cggcgctgac gcaatgcgcg     600
gcccgcgcgg cctgaaagcg gttggcccgt atgtggtcac caaagcgatg gcatccggcg     660
tttctgcctg cctcgccacc ccgtttaaaa ttcatggcgt taactactcc atcagctccg     720
cgtgtgcgac ttccgcacac tgtatcggta acgcagtaga gcagatccaa ctgggcaaac     780
aggacatcgt gtttgctggc ggcggcgaag agctgtgctg ggaaatggct tgcgaattcg     840
acgcaatggg tgcgctgtct actaaataca cgacacccc ggaaaaagcc tcccgtactt     900
acgacgctca ccgtgacggt ttcgttatcg ctggcggcgg cggtatggta gtggttgaag     960
agctggaaca cgcgctggcg cgtggtgctc acatctatgc tgaaatcgtt ggctacggcg    1020
caacctctga tggtgcagac atggttgctc cgtctggcga aggcgcagta cgctgcatga    1080
agatggcgat gcatggcgtt gataccccaa tcgattacct gaactcccac ggtacttcga    1140
ctccggttgg cgacgtgaaa gagctggcag ctatccgtga agtgttcggc gataagagcc    1200
cggcgatttc tgcaaccaaa gccatgaccg tcactctct gggcgctgct ggcgtacagg    1260
aagctatcta ctctctgctg atgctggaac acggcttcat cgccccgagc atcaacattg    1320
aagagctgga cgagcaggct gcaggtctga acatcgtgac gaaacgacc gatcgcgaac    1380 tgaccaccgt tatgtctaac agcttcggct tcggcggcac caacgccacg ctggtaatgc    1440
gcaagctgaa agattaattc gccgtaggtc gggtaaggcg cgccagcgtc gcatccgacg    1500
ttacgcgcca atgcggcctc cggcactaac acaaaaaggg aacccgatgg ttccctttt    1560 cacatcattg acaatcgccg cctgttccag gcaaacttcc cgctttgtcg atttccttct    1620
gaaaagacgt acgcgttaaa tcctgccaac gcactgtaac cctgaaacca gagagatgag    1680
acggggatac tcctcgcctt gcgctgcatt ctggagtaat gcatgactgc tgtaagccaa    1740
accgaaacac                                                           1750

<210> SEQ ID NO 4
```

```
<211> LENGTH: 406
<212> TYPE: PRT
<213> ORGANISM: Escherichia coli

<400> SEQUENCE: 4

Met Lys Arg Ala Val Ile Thr Gly Leu Gly Ile Val Ser Ser Ile Gly
 1               5                  10                  15

Asn Asn Gln Gln Glu Val Leu Ala Ser Leu Arg Glu Gly Arg Ser Gly
             20                  25                  30

Ile Thr Phe Ser Gln Glu Leu Lys Asp Ser Gly Met Arg Ser His Val
         35                  40                  45

Trp Gly Asn Val Lys Leu Asp Thr Thr Gly Leu Ile Asp Arg Lys Val
     50                  55                  60

Val Arg Phe Met Ser Asp Ala Ser Ile Tyr Ala Phe Leu Ser Met Glu
 65                  70                  75                  80

Gln Ala Ile Ala Asp Ala Gly Leu Ser Pro Glu Ala Tyr Gln Asn Asn
                 85                  90                  95

Pro Arg Val Gly Leu Ile Ala Gly Ser Gly Gly Gly Ser Pro Arg Phe
            100                 105                 110

Gln Val Phe Gly Ala Asp Ala Met Arg Gly Pro Arg Gly Leu Lys Ala
        115                 120                 125

Val Gly Pro Tyr Val Val Thr Lys Ala Met Ala Ser Gly Val Ser Ala
    130                 135                 140

Cys Leu Ala Thr Pro Phe Lys Ile His Gly Val Asn Tyr Ser Ile Ser
145                 150                 155                 160

Ser Ala Cys Ala Thr Ser Ala His Cys Ile Gly Asn Ala Val Glu Gln
                165                 170                 175

Ile Gln Leu Gly Lys Gln Asp Ile Val Phe Ala Gly Gly Gly Glu Glu
            180                 185                 190

Leu Cys Trp Glu Met Ala Cys Glu Phe Asp Ala Met Gly Ala Leu Ser
        195                 200                 205

Thr Lys Tyr Asn Asp Thr Pro Glu Lys Ala Ser Arg Thr Tyr Asp Ala
    210                 215                 220

His Arg Asp Gly Phe Val Ile Ala Gly Gly Gly Met Val Val
225                 230                 235                 240

Glu Glu Leu Glu His Ala Leu Ala Arg Gly Ala His Ile Tyr Ala Glu
                245                 250                 255

Ile Val Gly Tyr Gly Ala Thr Ser Asp Gly Ala Asp Met Val Ala Pro
            260                 265                 270

Ser Gly Glu Gly Ala Val Arg Cys Met Lys Met Ala Met His Gly Val
        275                 280                 285

Asp Thr Pro Ile Asp Tyr Leu Asn Ser His Gly Thr Ser Thr Pro Val
    290                 295                 300

Gly Asp Val Lys Glu Leu Ala Ala Ile Arg Glu Val Phe Gly Asp Lys
305                 310                 315                 320

Ser Pro Ala Ile Ser Ala Thr Lys Ala Met Thr Gly His Ser Leu Gly
                325                 330                 335

Ala Ala Gly Val Gln Glu Ala Ile Tyr Ser Leu Leu Met Leu Glu His
            340                 345                 350

Gly Phe Ile Ala Pro Ser Ile Asn Ile Glu Glu Leu Asp Glu Gln Ala
        355                 360                 365

Ala Gly Leu Asn Ile Val Thr Glu Thr Thr Asp Arg Glu Leu Thr Thr
    370                 375                 380
```

```
Val Met Ser Asn Ser Phe Gly Phe Gly Gly Thr Asn Ala Thr Leu Val
385                 390             395                 400

Met Arg Lys Leu Lys Asp
                405
```

METHODS FOR INCREASING ISOPRENOID AND ISOPRENOID PRECURSOR PRODUCTION BY MODULATING FATTY ACID LEVELS

CROSS-REFERENCE

This application claims the benefit of U.S. Provisional Patent Application No. 60/802,266, filed May 19, 2006, which application is incorporated herein by reference in its entirety.

BACKGROUND

Engineering microorganisms for the production of industrial products has become increasingly attractive in the past decades due to multiple advantages over traditional synthetic methods. Creating new biosynthetic capabilities in microorganisms allows previously limited products, such as therapeutic proteins and complex natural chemicals to be produced and purified at high levels while reducing the use of petroleum-based organic precursors and environmentally destructive chemical processes. In this effort, research has shifted focus from engineering the production of a single recombinant protein to the production of small molecule (e.g., non-protein) products, both natural and synthetic.

Isoprenoids are a highly diverse class of natural products from which numerous commercial flavors, fragrances, chemicals, and medicines are derived. Isoprenoids constitute an extremely large and diverse group of natural products that have a common biosynthetic origin, i.e., a single metabolic precursor, isopentenyl diphosphate (IPP). At least 20,000 isoprenoids have been described. By definition, isoprenoids are made up of so-called isoprene (C5) units. The number of C-atoms present in the isoprenoids is typically divisible by five (C5, C10, C15, C20, C25, C30 and C40), although irregular isoprenoids and polyterpenes have been reported. Isoprenoid compounds are also referred to as "terpenes" or "terpenoids." Important members of the isoprenoids include the carotenoids, monoterpenoids, sesquiterpenoids, diterpenoids, and hemiterpenes. Carotenoids include, e.g., lycopene, β-carotene, and the like, many of which function as antioxidants. Monoterpenoids include, e.g., menthol and camphor, which are flavor and fragrance agents. Sesquiterpenoids include, e.g., artemisinin, a compound having anti-malarial activity. Diterpenoids include, e.g., taxol, a cancer chemotherapeutic agent.

These valuable compounds are commonly isolated from plants, microbes, and marine organisms where they are naturally produced in small quantities. As such, purification from native sources suffers from low yields, impurities, and excessive consumption of natural resources. Furthermore, most of these compounds are chemically complex, resulting in chemical synthesis routes that are difficult, expensive, and suffer from low yields. For these reasons, the engineering of metabolic pathways to produce large quantities of complex isoprenoids in a tractable biological host presents an attractive alternative to extractions from environmental sources or chemical syntheses. Production consistency, scalability, and efficiency of substrate-to-product conversion of microbial fermentation are of particular importance to producing isoprenoid products on the scale and cost of commodity chemicals.

There is a need in the art for methods of making various products of medical and commercial interest, where the products, or precursors of same, are synthesized in genetically modified host cells.

LITERATURE

U.S. Pat. No. 7,183,089; U.S. Pat. No. 7,192,751; U.S. Pat. No. 7,172,886; Martin et al. (2003) *Nat. Biotech.* 21(7): 796-802; U.S. Pat. No. 7,129,392; U.S. Patent Publication No. 2004/0072323; U.S. Patent Publication No. 2004/0029239; U.S. Patent Publication No. 2004/0110257; U.S. Patent Publication No. 2004/0063182; U.S. Pat. No. 5,460,949; U.S. Patent Publication No. 2004/0077068; U.S. Pat. No. 6,531,303; U.S. Pat. No. 6,689,593.

SUMMARY OF THE INVENTION

The present invention provides methods of increasing production of an isoprenoid or an isoprenoid precursor in a host cell, the methods generally involving modulating the level of activity of a fatty acid biosynthetic pathway enzyme in the host cell and/or culturing the host cell in a culture medium comprising a fatty acid or a compound that can be metabolized in a cell or broken down in the medium to yield a fatty acid and/or culturing the host cell in a culture medium having increased osmolarity.

BRIEF DESCRIPTION OF THE DRAWINGS

FIGS. 4A and 4B provide nucleotide (4A) and amino acid (4B) sequences of a malonyl-CoA:ACP acyltransferase.

FIGS. 6A-G depict acyl-CoA levels, adenylate energy charge, and growth of cells expressing MevT operon genes.

FIGS. 7A-H depict acyl-CoA levels, adenylate energy charge, growth, and mevalonate production of cells overexpressing tHMGR and MevT operons.

FIGS. 8A-C and FIG. 9 depict the response of *E. coli* stress regulon genes to the accumulation of HMG-CoA

DEFINITIONS

The terms "isoprenoid," "isoprenoid compound," "terpene," "terpene compound," "terpenoid," and "terpenoid compound" are used interchangeably herein. Isoprenoid compounds are made up various numbers of so-called isoprene (C5) units. The number of C-atoms present in the isoprenoids is typically evenly divisible by five (e.g., C5, C10, C15, C20, C25, C30 and C40). Irregular isoprenoids and polyterpenes have been reported, and are also included in the definition of "isoprenoid." Isoprenoid compounds include, but are not limited to, monoterpenes, diterpenes, triterpenes, sesquiterpenes, and polyterpenes.

"Fatty acid" refers to a compound of the formula RCOOH, where R is a hydrocarbon. An unsaturated fatty acid refers to a compound where R includes at least one carbon-carbon double bond. A polyunsaturated fatty acid refers to a compound where R includes a plurality of carbon-carbon double bonds. A saturated fatty acid refers to a compound where R is a saturated aliphatic group.

As used herein, the term "prenyl diphosphate" is used interchangeably with "prenyl pyrophosphate," and includes monoprenyl diphosphates having a single prenyl group (e.g., IPP and DMAPP), as well as polyprenyl diphosphates that include 2 or more prenyl groups. Monoprenyl diphosphates include isopentenyl pyrophosphate (IPP) and its isomer dimethylallyl pyrophosphate (DMAPP).

As used herein, the term "terpene synthase" refers to any enzyme that enzymatically modifies IPP, DMAPP, or a polyprenyl pyrophosphate, such that a terpene or a terpenoid precursor compound is produced.

The word "pyrophosphate" is used interchangeably herein with "diphosphate." Thus, e.g., the terms "prenyl diphosphate" and "prenyl pyrophosphate" are interchangeable; the terms "isopentenyl pyrophosphate" and "isopentenyl diphosphate" are interchangeable; the terms farnesyl diphosphate" and farnesyl pyrophosphate" are interchangeable; etc.

The term "mevalonate pathway" or "MEV pathway" is used herein to refer to the biosynthetic pathway that converts acetyl-CoA to IPP. The mevalonate pathway comprises enzymes that catalyze the following steps: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate. The mevalonate pathway is illustrated schematically in FIG. 1. The "top half" of the mevalonate pathway refers to the enzymes responsible for the conversion of acetyl-CoA to mevalonate through a MEV pathway intermediate.

Figure 1:
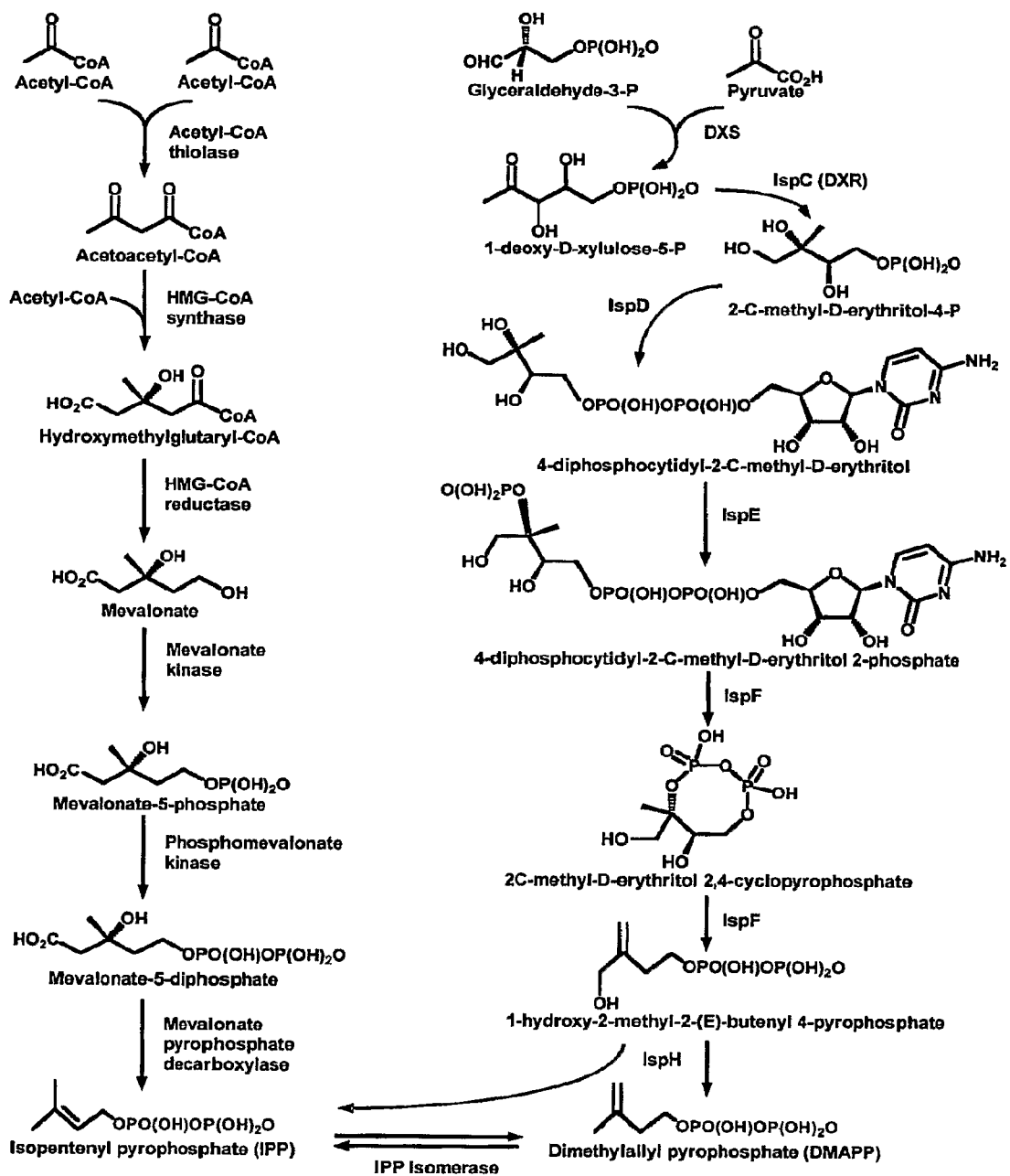
FIG. 1 is a schematic depiction of mevalonate and 1-deoxy-D-xylulose 5-diphosphate (DXP) pathways.

The term "1-deoxy-D-xylulose 5-diphosphate pathway" or "DXP pathway" is used herein to refer to the pathway that converts glyceraldehyde-3-phosphate and pyruvate to IPP and DMAPP through a DXP pathway intermediate, where DXP pathway comprises enzymes that catalyze the reactions depicted schematically in FIG. 1.

As used herein, the term "prenyl transferase" is used interchangeably with the terms "isoprenyl diphosphate synthase" and "polyprenyl synthase" (e.g., "GPP synthase," "FPP synthase," "OPP synthase," etc.) to refer to an enzyme that catalyzes the consecutive 1'-4 condensation of isopentenyl diphosphate with allylic primer substrates, resulting in the formation of prenyl diphosphates of various chain lengths.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "naturally-occurring" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell. For example, the nucleic acids encoding HMGS, mevalonate kinase, and phosphomevalonate kinase in represent exogenous nucleic acids to *E. coli*. These mevalonate pathway nucleic acids were cloned from *Sacchromyces cerevisiae*. In *S. cerevisiae*, the gene sequences encoding HMGS, MK, and PMK on the chromosome would be "endogenous" nucleic acids.

The term "heterologous nucleic acid," as used herein, refers to a nucleic acid wherein at least one of the following is true: (a) the nucleic acid is foreign ("exogenous") to (i.e., not naturally found in) a given host microorganism or host cell; (b) the nucleic acid comprises a nucleotide sequence that is naturally found in (e.g., is "endogenous to") a given host microorganism or host cell (e.g., the nucleic acid comprises a nucleotide sequence that is endogenous to the host microorganism or host cell) but is either produced in an unnatural (e.g., greater than expected or greater than naturally found) amount in the cell, or differs in sequence from the endogenous nucleotide sequence such that the same encoded protein (having the same or substantially the same amino acid sequence) as found endogenously is produced in an unnatural (e.g., greater than expected or greater than naturally found) amount in the cell; (c) the nucleic acid comprises two or more nucleotide sequences or segments that are not found in the same relationship to each other in nature, e.g., the nucleic acid is recombinant.

The term "heterologous polypeptide," as used herein, refers to a polypeptide that is not naturally associated with a given polypeptide. For example, an isoprenoid precursor-modifying enzyme that comprises a "heterologous transmembrane domain" refers to an isoprenoid precursor-modifying enzyme that comprises a transmembrane domain that is not normally associated with (e.g., not normally contiguous with; not normally found in the same polypeptide chain with) the isoprenoid precursor-modifying enzyme in nature.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination can be accomplished by chemical synthesis means, by the artificial manipulation of isolated segments of nucleic acids, e.g., by genetic engineering techniques, or a combination of such methods.

Similarly, the term "recombinant" polypeptide refers to a polypeptide which is not naturally occurring, e.g., is made by the artificial combination of two otherwise separated segments of amino sequence through human intervention.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

As used herein, the terms "operon" and "single transcription unit" are used interchangeably to refer to two or more contiguous coding regions (nucleotide sequences that encode a gene product such as an RNA or a protein) that are coordinately regulated by one or more controlling elements (e.g., a promoter). As used herein, the term "gene product" refers to RNA encoded by DNA (or vice versa) or protein that is encoded by an RNA or DNA, where a gene will typically comprise one or more nucleotide sequences that encode a protein, and may also include introns and other non-coding nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in viva or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products such as mevalonate pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acids substitution groups are: valine-leucine-isoleucine, phenylalanine-tyrosine, lysine-arginine, alanine-valine, and asparagine-glutamine.

"Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. The nucleotide sequence of the nucleic acids can be modified for optimal expression based on optimization of nucleotide sequence to reflect the codon bias of the host cell. The skilled artisan appreciates the likelihood of successful expression if codon usage is biased towards those codons favored by the host. Determination of preferred codons can be based on a survey of genes derived from the host cell where sequence information is available.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/0.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1× SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a fatty acid synthase" includes a plurality of such synthases and reference to "the fatty acid synthase inhibitor" includes reference to one or more fatty acid synthase inhibitors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides methods of increasing production of an isoprenoid or an isoprenoid precursor in a host cell, the methods generally involving modulating the level of activity of a fatty acid biosynthetic pathway enzyme in the host cell and/or culturing the host cell in a culture medium comprising a fatty acid or a compound that can be metabolized in a cell or broken down in the medium to yield a fatty acid and/or culturing the host cell in a culture medium having increased osmolarity.

Figure 2:
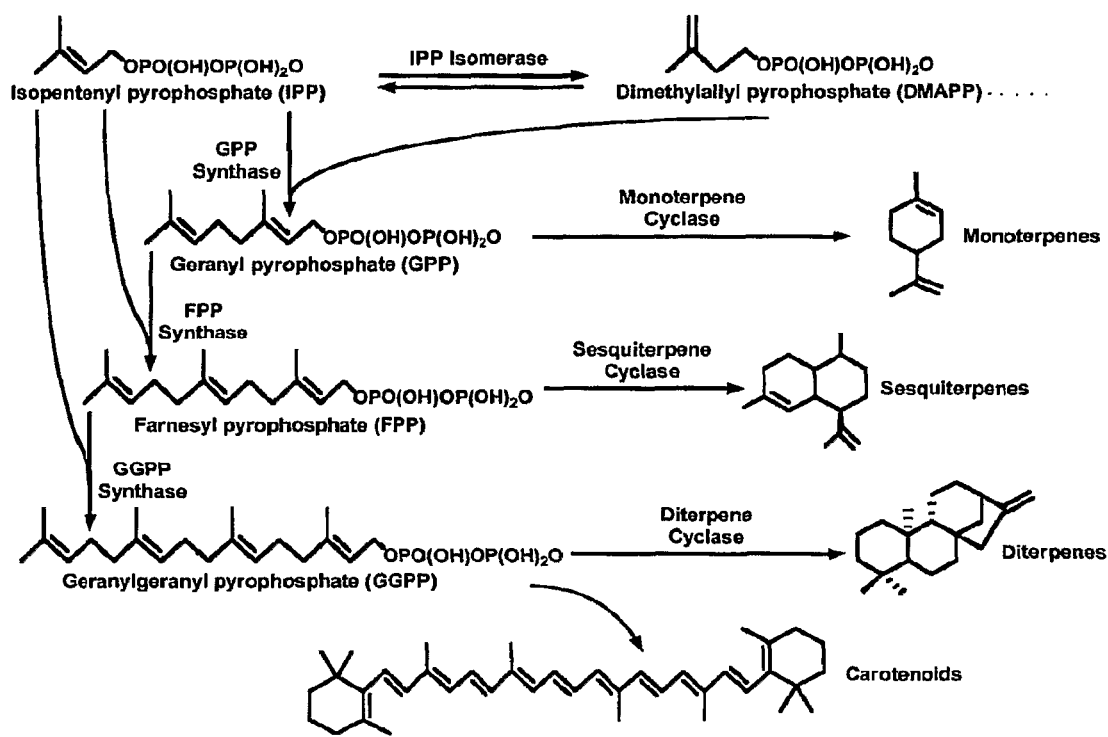
FIG. 2 is a schematic depiction of synthesis of various isoprenoid compounds from the precursors isopentenyl pyrophosphate and dimethylallyl pyrophosphate.
Figure 3:
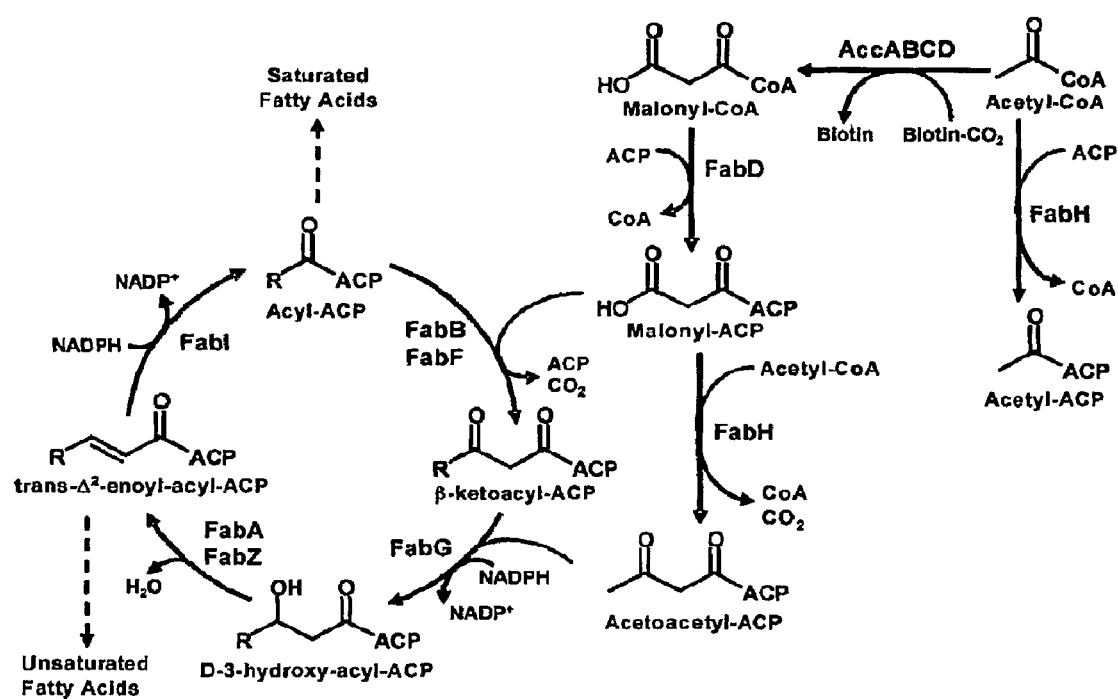
FIG. 3 is a schematic depiction of the initial steps in the type II fatty acid biosynthetic pathway.

The various biosynthetic pathways discussed herein are depicted schematically in FIGS. 1-3. These pathways include biosynthetic pathways leading to isoprenoid compounds and/or isoprenoid precursors; and fatty acid biosynthetic pathways.

Isoprenoid compounds are synthesized from a universal five carbon precursor, isopentenyl pyrophosphate (IPP) IPP is synthesized via two different pathways: the mevalonate (MEV) pathway and the 1-deoxyxylulose-5-phosphate (DXP) or non-mevalonate pathway. The MEV pathway and the DXP pathway are depicted schematically in FIG. 1. The mevalonate pathway comprises the following enzymatic reactions: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate.

The DXP pathway produces EPP and DMAPP from pyruvate and glyceraldehyde-3-phosphate, as depicted schematically in FIG. 1. The pathway begins with the formation of 1-deoxy-D-xylulose-5-phosphate (DXP) from pyruvate and glyceraldehyde-3-phosphate by DXP synthase (Dxs). DXP is then isomerized and reduced to 2-C-methyl-D-erythritol-4-phosphate (IEP), the first committed step of the non-mevalonate pathway, by DXP reductoisomerase (IspC or Dxr). In the next step, a cytidylic acid moiety is added to MEP by the action 2-C-methylerythritol-4-phosphate cytidyltransferase (IspD) to produce 4-diphosphocytidyl-2C-methyl-D-erythritol. 4-diphosphocytidyl-2C-methyl-D-erythritol is then phosphorylated by 4-diphosphocytidyl-2C-methyl-D-erythritol kinase (IspE) and further converted to 1-hydroxy-2-methyl-2-(E)-butenyl-4-diphosphate by the sequential action of 2-C-methylerythritol-2,4-cyclodiphosphate synthase (IspF) and 1-hydroxy-2-methyl-2-(E)-butenyl-4-diphosphate synthase (IspG). The terminal enzyme of the DXP pathway in *E. coli* has recently been identified as the product of ispH (formerly lytB), and has been shown to convert 1-hydroxy-2-methyl-2-(E)-butenyl 4-diphosphate to both IPP and DMAPP at a 5:1 ratio.

As depicted schematically in FIG. 2, DMAPP acts as a primer for the sequential additions of IPP by the isoprenyl pyrophosphate synthases (also known as the prenyl transferases) to form $C_{10}$ geranyl pyrophosphate (GPP), $C_{15}$ farnesyl pyrophosphate (FPP), $C_{20}$ geranylgeranyl pyrophosphate (GGPP), and larger isoprenyl pyrophosphates. The isoprenyl pyrophosphates are then cyclized by the terpene cyclases (synthases) to form the various terpene classes. Carotenoids are synthesized by a series of enzymatic reactions beginning with the condensation of two GGPP molecules.

Production of isoprenoid compounds (and/or precursors such as mevalonate, IPP, and polyprenyl diphosphates) in host cells (e.g., a host microorganism) transformed ("genetically modified") with one or more heterologous nucleic acids comprising nucleotide sequences encoding one or more mevalonate pathway enzymes can lead to production of isoprenoid and/or isoprenoid precursor compounds. However, HMG-CoA, an intermediate in the mevalonate pathway, is toxic when it accumulates in a microbial host genetically modified to produce isoprenyl pyrophosphate (IPP) or an IPP precursor via the mevalonate pathway. The present invention is based in part on the observation that HMG-CoA toxicity in *Escherichia coli* is due, at least in part, to inhibition of the early steps of the type II fatty acid biosynthesis pathway in *E. coli*. The type II fatty acid biosynthesis pathway in *E. coli* is depicted in FIG. 3.

Features of the Invention

The present invention features a method of producing an isoprenoid or an isoprenoid precursor in a genetically modified host cell (e.g., a prokaryotic cell cultured in vitro). In some embodiments, the methods involve culturing a genetically modified host cell (e.g., a plurality of genetically modified host cells) in vitro in a culture medium comprising a $C_{12}$-$C_{22}$ fatty acid. The genetically modified host cells are genetically modified with one or more nucleic acids comprising nucleotide sequences encoding heterologous mevalonate pathway enzymes that convert acetyl-CoA to isopentenyl pyrophosphate. The genetically modified host cell includes an endogenous type II fatty acid biosynthetic pathway. In some embodiments, the $C_{12}$-$C_{22}$ fatty acid is a $C_{12}$ saturated fatty acid. In other embodiments, the $C_{12}$-$C_{22}$ fatty acid is a $C_{14}$ saturated fatty acid. In other embodiments, the $C_{12}$-$C_{22}$ fatty acid is a $C_{16}$ saturated fatty acid. In other embodiments, the $C_{12}$-$C_{22}$ fatty acid is a $C_{18}$ saturated fatty acid. In other embodiments, the $C_{12}$-$C_{22}$ fatty acid is a $C_{20}$ saturated fatty acid. In other embodiments, the $C_{12}$-$C_{22}$ fatty acid is a $C_{22}$ saturated fatty acid. In an exemplary embodiment, the fatty acid is palmitic acid. The isoprenoid or isoprenoid precursor is produced in the genetically modified host cell(s) at a level that is higher than the level of the isoprenoid or isoprenoid precursor that would be produced by the genetically modified host cell(s) when cultured in a control culture medium not comprising a $C_{12}$-$C_{22}$ fatty acid. In some embodiments, the culture medium further comprises a supplement that increases the osmolarity compared to the osmolarity of the control culture medium. In some embodiments, the supplement is a salt in a concentration range of from about 50 mM to about 500 mM.

The present invention features a method of producing an isoprenoid or an isoprenoid precursor in a genetically modified host cell (e.g., a prokaryotic cell cultured in vitro). In some embodiments, the methods involve culturing a genetically modified host cell (e.g., a plurality of genetically modified host cells) in vitro in a culture medium comprising a supplement that increases the osmolarity compared to the osmolarity of a control culture medium. The genetically modified host cells are genetically modified with one or more nucleic acids comprising nucleotide sequences encoding heterologous mevalonate pathway enzymes that convert acetyl-CoA to isopentenyl pyrophosphate. The isoprenoid or isoprenoid precursor is produced in the genetically modified host cell(s) at a level that is higher than the level of the isoprenoid or isoprenoid precursor that would be produced by the genetically modified host cell(s) when cultured in a control culture medium not comprising the supplement that increases osmolarity. In some embodiments, the supplement is a salt in a concentration range of from about 50 mM to about 500 mM.

The present invention features a genetically modified host cell, where the genetically modified host cell comprises is genetically modified with at least one heterologous nucleic acid encoding a mevalonate pathway enzyme and a type II fatty acid biosynthetic enzyme; and where the genetically modified host cell comprises an endogenous type II fatty acid biosynthetic pathway. In some embodiments, the genetically modified host cell comprises all of the enzymes of the mevalonate pathway that convert acetyl-CoA to isopentenyl pyrophosphate. In some embodiments, the at least one heterologous nucleic acid encodes acetoacetyl-CoA thiolase, hydroxymethylglutaryl-CoA synthase, hydroxymethylglutaryl-CoA reductase, mevalonate kinase, phosphomevalonate kinase, mevalonate pyrophosphate decarboxylase, isopentenyl pyrophosphate isomerase, and a prenyl transferase. In some embodiments, the type II fatty acid biosynthetic enzyme is an enzyme that converts malonyl-CoA to malonyl-ACP. In some embodiments, the type II fatty acid biosynthetic enzyme is malonyl-CoA:ACP transferase. In some embodiments, the type II fatty acid biosynthetic enzyme is FadD. In some embodiments, the at least one heterologous nucleic acid encodes a plurality of type II fatty acid biosynthetic enzymes. In some embodiments, the plurality of type II fatty acid biosynthetic enzymes includes an enzyme that converts malonyl-CoA to malonyl-ACP and an enzyme that converts acyl-ACP to β-ketoacyl-ACP. In some embodiments, the plurality of type II fatty acid biosynthetic enzymes includes malonyl-CoA:ACP transferase and β-ketoacyl-ACP synthase I. In some embodiments, the plurality of type II fatty acid biosynthetic enzymes includes FadD and FadB.

Methods Enhancing Production Isoprenoids and Isoprenoid Precursors

The present invention provides methods of reducing HMG-CoA accumulation-induced toxicity in a host cell; and methods of increasing production of isoprenoid and isoprenoid precursor compounds in the host cell. In some embodiments, the methods generally involve modulating the level of activity of a fatty acid biosynthetic pathway enzyme in the host cell and/or culturing the host cell in a culture medium comprising a fatty acid or a compound that can be metabolized in a cell or broken down in the medium to yield a fatty acid and/or culturing the host cell in a culture medium having increased osmolarity.

Reducing HMG-CoA Accumulation-Induced Toxicity

In some embodiments, the host cell is one that comprises, or is genetically modified to comprise, nucleic acid(s) comprising nucleotide sequences encoding one or more enzymes in the mevalonate pathway. The host cell that comprises, or is genetically modified to comprise, nucleic acid(s) comprising nucleotide sequences encoding one or more enzymes in the mevalonate pathway, and that exhibits HMG-CoA accumulation-induced toxicity, is referred to herein as a "parent host cell" or "control parent host cell." The level of HMG-CoA accumulation-induced toxicity and/or isoprenoid or isoprenoid production in a host cell is compared to the level of HMG-CoA accumulation-induced toxicity and/or isoprenoid or isoprenoid production in a parent host cell.

The present invention is applicable to host cells that produce IPP and/or mevalonate via the mevalonate pathway. Such host cells are referred to herein as "parent" host cells and comprise, or are genetically modified to comprise, nucleic acids comprising nucleotide sequences encoding one or more enzymes in the mevalonate pathway (and therefore produce IPP and/or mevalonate via the mevalonate pathway). Parent host cells exhibit HMG-CoA accumulation-induced toxicity, where the level of intracellular HMG-CoA inhibits cell growth, in the absence of an additional genetic modification and/or culture condition, as described herein; thus, e.g., a parent host cell is one that, but for a genetic modification and/or culture condition as described herein, would accumulate HMG-CoA intracellularly and exhibit HMG-CoA accumulation-induced toxicity.

In one exemplary embodiment, a control parent cell is a prokaryotic host cell that has been genetically modified with one or more nucleic acids comprising nucleotide sequences encoding acetoacetyl-CoA thiolase, HMGS, and HMGR, where HMG-CoA is produced and accumulates intracellularly at levels that are growth inhibiting or toxic to the cell. As one non-limiting example, a control parent cell is an *E. coli* host cell that has been genetically modified with an expression construct comprising a nucleotide sequence encoding acetoacetyl-CoA thiolase, HMGS, and HMGR in a single polycistronic operon in the recited order on a plasmid or in the chromosome; and the genetically modified host cell is an *E. coli* genetically modified with expression construct(s) comprising the nucleotide sequences encoding acetoacetyl-CoA thiolase; HMGR, and HMGS in a single polycistronic operon in the adjusted recited order on a plasmid or in the chromosome. As an additional non-limiting example, a control parent cell is an *E. coli* host cell that has been genetically modified with an expression construct comprising a nucleotide sequence encoding acetoacetyl-CoA thiolase, HMGS, and HMGR in a single polycistronic operon in the recited order on a medium copy plasmid; and the genetically modified host cell is an *E. coli* genetically modified with expression construct(s) comprising a nucleotide sequence encoding acetoacetyl-CoA thiolase and HMGS in the recited order on a low copy plasmid, and a nucleotide sequence HMGR on a separate high copy plasmid. As an additional non-limiting example, a control parent cell is an *E. coli* host cell that has been genetically modified with an expression construct comprising a nucleotide sequence encoding acetoacetyl-CoA thiolase, HMGS, and HMGR in a single polycistronic operon in the recited order on a medium copy plasmid; and the genetically modified host cell is an *E. coli* genetically modified with expression construct(s) comprising a nucleotide sequence encoding acetoacetyl-CoA thiolase and HMGS in the recited order on a medium copy plasmid in which the ribosome binding site has been altered to reduce translation, and a nucleotide sequence HMGR on a separate medium copy plasmid for which the promoter has been changed to a stronger version. As an additional non-limiting example, a control parent cell is an *E. coli* host cell that has been genetically modified with an expression construct comprising a nucleotide sequence encoding acetoacetyl-CoA thiolase, HMGS, and HMGR in a single polycistronic operon in the recited order on a medium copy plasmid; and the genetically modified host cell is an *E. coli* genetically modified with expression construct(s) comprising a nucleotide sequence encoding acetoacetyl-CoA thiolase, HMGS with a engineered protease site, and HMGR to which a highly soluble protein such as glutathione transferase has been fused in the recited order on a medium copy plasmid. In some embodiments, the HMGR that is encoded is a truncated HMGR, as described in more detail below.

Using a subject method, HMG-CoA accumulation-induced growth inhibition is reduced, compared to the level of HMG-CoA accumulation-induced growth inhibition in a parent host cell. In addition, production of an isoprenoid or an isoprenoid precursor is increased in the host cell that is genetically modified and/or cultured according to a subject method, compared to the level of isoprenoid or isoprenoid precursor produced by the parent host cell. Thus, e.g., production of an isoprenoid or isoprenoid precursor is increased by at least about 10%, at least about 20%, at least about 50%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, in a host cell that is genetically modified and/or cultured according to a subject method, compared to the parent host cell.

Enhancing Isoprenoid or Isoprenoid Precursor Production

The present invention provides a method of producing an isoprenoid or an isoprenoid precursor in a genetically modified host cell (e.g., a prokaryotic cell cultured in vitro). In some embodiments, the methods involve culturing a genetically modified host cell (e.g., a plurality of genetically modified host cells) in vitro in a culture medium comprising a $C_{12}$-$C_{22}$ fatty acid. The genetically modified host cells are genetically modified with one or more nucleic acids comprising nucleotide sequences encoding heterologous mevalonate pathway enzymes that convert acetyl-CoA to isopentenyl pyrophosphate. The genetically modified host cell includes an endogenous type II fatty acid biosynthetic pathway.

The genetically modified host cells are cultured in a medium supplemented with one or more $C_{12}$-$C_{22}$ fatty acids. In some embodiments, the $C_{12}$-$C_{22}$ fatty acid is a $C_{12}$ saturated fatty acid. In other embodiments, the $C_{12}$-$C_{22}$ fatty acid is a $C_{14}$ saturated fatty acid. In other embodiments, the $C_{12}$-$C_{22}$ fatty acid is a $C_{16}$ saturated fatty acid. In other embodiments, the $C_{12}$-$C_{22}$ fatty acid is a $C_{18}$ saturated fatty acid. In other embodiments, the $C_{12}$-$C_{22}$ fatty acid is a $C_{20}$ saturated fatty acid. In other embodiments, the $C_{12}$-$C_{22}$ fatty acid is a $C_{22}$ saturated fatty acid. Suitable $C_{12}$-$C_{22}$ fatty acids are described in more detail below. In an exemplary embodiment, the fatty acid is palmitic acid.

The isoprenoid or isoprenoid precursor is produced in the genetically modified host cell(s) at a level that is higher than the level of the isoprenoid or isoprenoid precursor that would be produced by the genetically modified host cell(s) when cultured in a control culture medium not comprising a $C_{12}$-$C_{22}$ fatty acid. Thus, e.g., when the genetically modified host cell is cultured in a medium comprising one or more $C_{12}$-$C_{22}$ fatty acids, the isoprenoid or isoprenoid precursor is produced in the genetically modified host cell(s) at a level that is at least about 10%, at least about 20%, at least about 50%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, higher than the level of the isoprenoid or isoprenoid precursor that would be produced by the genetically modified host cell when cultured in a control culture medium not supplemented with the one or more $C_{12}$-$C_{22}$ fatty acids. In some embodiments, a subject method provides for production of an isoprenoid or isoprenoid precursor in a recoverable amount of from about 1 mg/L to about 50 g/L, e.g., from about 1 mg/L to about 5 mg/L, from about 5 mg/L to about 10 mg/L, from about 10 mg/L to about 25 mg/L, from about 25 mg/L to about 50 mg/L, from about 50 mg/L to about 100 mg/L, from about 100 mg/L to about 250 mg/L, from about 250 mg/L to about 500 mg/L, from about 500 mg/L to about 1 g/L, from about 1 g/L to about 5 g/L, from about 5 g/L to about 10 g/L, from about 10 g/L to about 15 g/L, from about 15 g/L to about 20 g/L, from about 20 g/L to about 25 g/L, from about 25 g/L to about 30 g/L, from about 30 g/L to about 40 g/L, or from about 40 g/L to about 50 g/L.

In some embodiments, the culture medium further comprises a supplement that increases the osmolarity compared to the osmolarity of the control culture medium. Suitable supplements are described in more detail below. In some embodiments, the supplement is a salt in a concentration range of from about 50 mM to about 500 mM.

The present invention provides a method of producing an isoprenoid or an isoprenoid precursor in a genetically modified host cell (e.g., a prokaryotic cell cultured in vitro). In some embodiments, the methods involve culturing a genetically modified host cell (e.g., a plurality of genetically modified host cells) in vitro in a culture medium comprising a supplement that increases the osmolarity compared to the osmolarity of a control culture medium. The genetically modified host cells are genetically modified with one or more nucleic acids comprising nucleotide sequences encoding heterologous mevalonate pathway enzymes that convert acetyl-CoA to isopentenyl pyrophosphate. The isoprenoid or isoprenoid precursor is produced in the genetically modified host cell(s) at a level that is higher than the level of the isoprenoid or isoprenoid precursor that would be produced by the genetically modified host cell(s) when cultured in a control culture medium not comprising the supplement that increases osmolarity. Thus, e.g., when the genetically modified host cell is cultured in a medium comprising the supplement that increased the osmolarity of the culture medium the isoprenoid or isoprenoid precursor is produced in the genetically modified host cell(s) at a level that is at least about 10%, at least about 20%, at least about 50%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, higher than the level of the isoprenoid or isoprenoid precursor that would be produced by the genetically modified host cell when cultured in a control culture medium not supplemented with the supplement that increased the osmolarity of the culture medium. In some embodiments, the supplement is a salt in a concentration range of from about 50 mM to about 500 mM. In some embodiments, a subject method provides for production of an isoprenoid or isoprenoid precursor in a recoverable amount of from about 1 mg/L to about 50 g/L, e.g., from about 1 mg/L to about 5 mg/L, from about 5 mg/L to about 10 mg/L, from about 10 mg/L to about 25 mg/L, from about 25 mg/L to about 50 mg/L, from about 50 mg/L to about 100 mg/L, from about 100 mg/L to about 250 mg/L, from about 250 mg/L to about 500 mg/L, from about 500 mg/L to about 1 g/L, from about 1 g/L to about 5 g/L, from about 5 g/L to about 10 g/L, from about 10 g/L to about 15 g/L, from about 15 g/L to about 20 g/L, from about 20 g/L to about 25 g/L, from about 25 g/L to about 30 g/L, from about 30 g/L to about 40 g/L, or from about 40 g/L to about 50 g/L.

Modulating a Level of a Fatty Acid Biosynthetic Enzyme in the Cell

In some embodiments, the present invention provides methods of reducing HMG-CoA accumulation-induced toxicity; and methods of increasing isoprenoid or isoprenoid precursor compound production in a host cell, where the methods generally involve modulating a level of a fatty acid biosynthetic enzyme in the host cell. The present invention further provides genetically modified host cells that are suitable for use in a subject method. The present invention further provides recombinant nucleic acid constructs for use in generating a subject genetically modified host cell.

In some embodiments, modulating a level of a fatty acid biosynthetic enzyme in a host cell involves modulating the level of a type II fatty acid biosynthetic enzyme in a host cell. In some embodiments, a subject method involves increasing the activity level of a type II fatty acid biosynthetic enzyme in the genetically modified host cell.

HMG-CoA can accumulate in a cell at levels that are toxic and that induce growth inhibition. In some embodiments, increasing the level of enzymatic activity of a type II fatty acid biosynthetic enzyme in a cell reduces growth inhibition by HMG-CoA accumulation in the cell. Thus, in some embodiments, increasing the level of enzymatic activity of a type I or a type II fatty acid biosynthetic enzyme in a cell reduces HMG-CoA accumulation-mediated growth inhibition by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to a control cell that exhibits HMG-CoA accumulation-induced growth inhibition. Growth of genetically modified host cells is readily determined using well-known methods, e.g., optical density (OD) measurement at about 600 nm ($OD_{600}$) of liquid cultures of bacteria; colony size; growth rate; and the like.

Increasing the Level of a Type II Fatty Acid Biosynthetic Pathway Enzyme in a Host Cell In some embodiments, a subject method involves genetically modifying a parent host cell with one or more nucleic acids comprising a nucleotide sequence encoding a type II fatty acid biosynthetic pathway enzyme. In some embodiments, the nucleic acid is overexpressed in the genetically modified host cell, thereby increasing the level of the type II fatty acid biosynthetic pathway enzyme in the host cell. In other embodiments, the fatty acid biosynthetic pathway enzyme that is encoded has increased specific activity compared to the specific activity of the enzyme that is produced by the parent host cell.

Increasing the level of activity of a type II fatty acid biosynthetic pathway enzyme in a cell is achieved in a number of ways, including, but not limited to: 1) increasing transcription of a nucleic acid encoding a type II fatty acid biosynthetic pathway enzyme; 2) increasing translation of an mRNA encoding a type II fatty acid biosynthetic pathway enzyme; 3) increasing stability of the mRNA encoding a type II fatty acid biosynthetic pathway enzyme; 4) increasing stability of the type II fatty acid biosynthetic pathway enzyme; and 5) increasing enzymatic activity of the type II fatty acid biosynthetic pathway enzyme.

Type II fatty acid biosynthetic pathway enzymes include, but are not limited to, malonyl-CoA:ACP transacylase, β-ketoacyl-ACP synthase I, β-ketoacyl-ACP synthase II, β-ketoacyl-ACP synthase III, acetyl-CoA:ACP transacylase, malonyl-ACP decarboxylase, β-ketoacyl-ACP reductase, β-hydroxyacyl-ACP dehydratase, β-hydroxydecanoyl-ACP dehydrase, trans-2-decenoyl-ACP isomerase, and enoyl-ACP reductase. "ACP" is "acetyl carrier protein."

The source of the type II fatty acid biosynthetic pathway enzyme-encoding nucleotide sequence will in some embodiments be a naturally-occurring source. In other embodiments, the type II fatty acid biosynthetic pathway enzyme-encoding nucleotide sequence is synthetic.

Naturally-occurring sources of type II fatty acid biosynthetic pathway enzyme-encoding nucleotide sequences include any cell, tissue, or organism that harbors a type II fatty acid biosynthetic pathway. Such sources include, but are not limited to, a eubacterium; an archaebacterium; a plant; an organelle of a eukaryotice cell, e.g., a mitochondrion of a eukaryotic cell; and the like. Suitable plant sources include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable prokaryotic cells include bacteria (e.g., Eubacteria) and archaebacteria. Suitable archaebacteria include a methanogen, an extreme halophile, an extreme thermophile, and the like. Suitable archaebacteria include, but are not limited to, any member of the groups Crenarchaeota (e.g., *Sulfolobus solfataricus, Defulfurococcus mobilis, Pyrodictium occultum, Thermofilum pendens, Thermoproteus tenax*), Euryarchaeota (e.g., *Thermococcus celer, Methanococcus thermolithotrophicus, Methanococcus jannaschii, Methanobacterium thermoautotrophicum, Methanobacterium formicicum, Methanothermus fervidus, Archaeoglobus fulgidus, Thermoplasma acidophilum, Haloferax volcanni, Methanosarcina barkeri, Methanosaeta concilli, Methanospririllum hungatei, Methanomicrobium mobile*), and Korarchaeota. Suitable eubacteria include, but are not limited to, any member of Hydrogenobacteria, Thermotogales, Green nonsulfphur bacteria, Denococcus Group, Cyanobacteria, Purple bacteria, Planctomyces, Spirochetes, Green Sulphur bacteria, Cytophagas, and Gram positive bacteria (e.g., *Mycobacterium* sp., *Micrococcus* sp., *Streptomyces* sp., *Lactobacillus* sp., *Helicobacterium* sp., *Clostridium* sp., *Mycoplasma* sp., *Bacillus* sp., etc.).

In some embodiments, a type II fatty acid biosynthetic pathway enzyme-encoding nucleotide sequence has at least about 50%, at least about 60%, at least about 70%, at least about 75%, at least about 80%, at least about 85%, at least about 90%, at least about 95%, at least about 98%, or more, nucleotide sequence identity to the nucleotide sequence of a naturally-occurring type II fatty acid biosynthetic pathway enzyme-encoding nucleotide sequence.

For example, in some embodiments, a type II fatty acid biosynthetic pathway enzyme-encoding nucleotide sequence encodes a malonyl-CoA:ACP transacylase, and has at least about 50%, at least about 60%, at least about 70%, at least about 75%, at least about 80%, at least about 85%, at least about 90%, at least about 95%, at least about 98%, or more (e.g., 99%, 100%), nucleotide sequence identity to any one of the following sequences (or the coding sequence thereof): 1) the nucleotide sequence of *E. coli* malonyl-CoA:ACP transacylase as depicted in FIG. 4A and set forth in GenBank Accession No. AE014075 (gene=FabD; locus tag c1361); 2) the nucleotide sequence of *E. coli* malonyl-CoA:ACP transacylase as set forth in nucleotides 532-1461 of the nucleotide sequence set forth in GenBank Accession No. M870040; 3) the nucleotide sequence of a *Pseudomonas* malonyl-CoA:ACP transacylase as set forth in GenBank Accession number AB025101; 4) the nucleotide sequence of a *Streptomyces avermitilis* MA-4680 malonyl-CoA:ACP transacylase as set forth in GenBank Accession No. NC_00315 (locus tag SAV5788; gene ID 1211344); 5) the nucleotide sequence of a *Rhodobacter sphaeroides* malonyl-CoA:ACP transacylase as set forth in GenBank Accession No. NC_007493 (locus tag RSP_2682; gene ID 3720373); 6) the nucleotide sequence of a *Streptomyces coelicolor* malonyl-CoA:ACP transacylase as set forth in GenBank Accession No. NC_003888 (locus tag SCO2387; gene ID 1097821); and 7) the nucleotide sequence of an *Arabidopsis thaliana* malonyl-CoA:ACP transacylase as set forth in GenBank Accession No. NC_003071 (locus tag AT2G30200; gene ID 817570).

In other embodiments, a type II fatty acid biosynthetic pathway enzyme-encoding nucleotide sequence encodes a β-ketoacyl-ACP synthase I, and has at least about 50%, at least about 60%, at least about 70%, at least about 75%, at least about 80%, at least about 85%, at least about 90%, at least about 95%, at least about 98%, or more (e.g., 99%, 100%), nucleotide sequence identity to any one of the following sequences (or the coding sequence thereof): 1) the nucleotide sequence of *E. coli* β-ketoacyl-ACP synthase I as set forth in GenBank Accession No. M24427; 2) the nucleotide sequence of *Pseudomonas putida* β-ketoacyl-ACP synthase I as set forth in GenBank Accession No. NC_002947 (locus tag PP4175; gene ID 1042370); and 3) the nucleotide sequence of *Rhodobacter sphaeroides* β-ketoacyl-ACP synthase I as set forth in GenBank Accession No. NC_007493 (locus tag RSP-2777; gene ID 3720510). For example, in some embodiments, a type II fatty acid biosynthetic pathway enzyme-encoding nucleotide sequence encodes a β-ketoacyl-ACP synthase I, and has at least about 50%, at least about 60%, at least about 70%, at least about 75%, at least about 80%, at least about 85%, at least about 90%, at least about 95%, at least about 98%, or more (e.g., 99%, 100%), nucleotide sequence identity to nucleotides 237-1457 of the nucleotide sequence set forth in GenBank Accession No. M24427 (e.g., nucleotides 237-1457 of the nucleotide sequence set forth in SEQ ID NO:3).

In some embodiments, a type II fatty acid biosynthetic pathway enzyme-encoding nucleotide sequence encodes a type II fatty acid biosynthetic pathway enzyme having at least about 50%, at least about 60%, at least about 70%, at least about 75%, at least about 80%, at least about 85%, at least about 90%, at least about 95%, at least about 98%, or more (e.g., 99%, 100%), amino acid sequence identity to the amino acid sequence of a naturally-occurring type II fatty acid biosynthetic pathway enzyme.

For example, in some embodiments, a type II fatty acid biosynthetic pathway enzyme-encoding nucleotide sequence encodes a malonyl-CoA:ACP transacylase that has at least about 50%, at least about 60%, at least about 70%, at least about 75%, at least about 80%, at least about 85%, at least about 90%, at least about 95%, at least about 98%, or more (e.g., 99%, 100%), amino acid sequence identity to any one of the following amino acid sequences: 1) the amino acid sequence of *E. coli* malonyl-CoA:ACP transacylase as depicted in FIG. 4B and set forth in GenBank Accession No. AAN79832.1; 2) the amino acid sequence of *E. coli* malonyl-CoA:ACP transacylase as set forth in GenBank Accession No. CAA77658; 3) the amino acid sequence of *Bacteroides fragilis* malonyl-CoA:ACP transacylase as set forth in GenBank Accession No. CAH08050; 4) the amino acid sequence of *Mycobacterium bovis* malonyl-CoA:ACP transacylase as set forth in GenBank Accession No. NP_855916; 5) the amino acid sequence of *Erwinia carotovora* malonyl-CoA:ACP transacylase as set forth in GenBank Accession No. YP_049896; and 6) the amino acid sequence of a *Pseudomonas* malonyl-CoA:ACP transacylase as set forth in GenBank Accession No. BAA76353.

In other embodiments, a type II fatty acid biosynthetic pathway enzyme-encoding nucleotide sequence encodes a β-ketoacyl-ACP synthase I that has at least about 50%, at least about 60%, at least about 70%, at least about 75%, at least about 80%, at least about 85%, at least about 90%, at least about 95%, at least about 98%, or more (e.g., 99%, 100%), amino acid sequence identity to any one of the following amino acid sequences: 1) the amino acid sequence of *E. coli* β-ketoacyl-ACP synthase I as set forth in GenBank Accession No. AAC67304 (SEQ ID NO:4); 2) the amino acid sequence of *Yersinia pestis* β-ketoacyl-ACP synthase I as set forth in GenBank Accession No. CAC92996; and 3) the amino acid sequence of *Erwinia carotovora* β-ketoacyl-ACP synthase I as set forth in GenBank Accession No. CAG75962.

Genetically modifying a parent host cell with nucleic acid(s) comprising nucleotide sequences encoding one or more type II fatty acid biosynthetic pathway enzymes generates a genetically modified host cell that: i) exhibits reduced HMG-CoA accumulation-induced growth inhibition, compared to the parent host cell. Thus, genetic modification with one or more nucleic acids encoding one or more type II fatty acid biosynthetic pathway enzymes reduces HMG-CoA accumulation-mediated growth inhibition by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to a control parent cell that exhibits HMG-CoA accumulation-induced growth inhibition. Growth of genetically modified host cells is readily determined using well-known methods, e.g., optical density (OD) measurement at about 600 nm ($OD_{600}$) of liquid cultures of bacteria; colony size; growth rate; and the like.

Genetically modifying a parent host cell with nucleic acid(s) comprising nucleotide sequences encoding one or more type II fatty acid biosynthetic pathway enzymes generates a genetically modified host cell that: i) exhibits reduced HMG-CoA accumulation-induced growth inhibition, compared to the parent host cell; and ii) produces a level of an isoprenoid or isoprenoid precursor that is higher than the level produced by the parent host cell. For example, in some embodiments, a subject method involves: (a) genetically modifying a parent host cell to contain one or more heterologous nucleic acids encoding one or more type II fatty acid biosynthetic pathway enzymes, generating a genetically modified host cell, where the one or more enzymes, when produced in the cell, reduce HMG-CoA accumulation-induced growth inhibition, as compared to a control parent host cell that is not genetically modified with the heterologous nucleic acids; and (b) culturing the genetically modified host cell under conditions such that the level of isoprenoid or isoprenoid precursor produced in the genetically modified host cell is higher than the level of isoprenoid or isoprenoid precursor produced in the control parent host cell.

In some embodiments, a heterologous nucleic acid comprising a nucleotide sequence encoding a heterologous type II fatty acid biosynthetic pathway enzyme is introduced into a parent control host cell, generating a genetically modified host cell. In some embodiments, the heterologous type II fatty acid biosynthetic pathway enzyme is produced in the cell at a level that is higher than a corresponding endogenous type II fatty acid biosynthetic pathway enzyme, e.g., the level of heterologous type II fatty acid biosynthetic pathway enzyme is produced in the cell is at least about 10%, at least about 25%, at least about 50%, at least about 75%, at least about 100% or 2-fold, at least about 5-fold, at least about 10-fold, at least about 20-fold, or higher, than the level of the corresponding endogenous type II fatty acid biosynthetic pathway enzyme. In some embodiments, the type II fatty acid biosynthetic pathway enzyme-encoding nucleotide sequence is operably linked to a strong promoter. In other embodiments, the type II fatty acid biosynthetic pathway enzyme-encoding nucleotide sequence is on a high copy number plasmid.

In some embodiments, the promoter to which the type II fatty acid biosynthetic pathway enzyme-encoding nucleotide sequence is operably linked is a stronger promoter than a reference promoter, e.g., the level of mRNA transcribed is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 5-fold, at least about 10-fold, or more, higher than the level of mRNA transcribed using the reference promoter. Suitable strong promoters include, but are not limited to, a consensus lac promoter, a trp promoter, a tac promoter, a trc promoter, a lambda promoter, a salicylate promoter, and a T7 promoter.

Increasing the plasmid copy number is achieved by selecting a plasmid backbone that is known to be a medium or high copy number plasmid. Low copy number plasmids generally provide for fewer than about 20 plasmid copies per cell. Medium copy number plasmids generally provide for from about 20 plasmid copies per cell to about 50 plasmid copies per cell, or from about 20 plasmid copies per cell to about 80 plasmid copies per cell. High copy number plasmids generally provide for from about 80 plasmid copies per cell to about 200 plasmid copies per cell, or more. In many embodiments, a nucleic acid comprising a nucleotide sequence encoding HMGR is a high copy number plasmid vector comprising a nucleic acid comprising a nucleotide sequence encoding HMGR. Suitable high copy number plasmids include, but are not limited to, pUC vectors (e.g., pUC8, pUC18, pUC19, and the like), pBluescript vectors, pGEM vectors, and pTZ vectors.

In other embodiments, the heterologous type II fatty acid biosynthetic pathway enzyme has a specific activity that is higher than the specific activity of the corresponding endogenous type II fatty acid biosynthetic pathway enzyme. Certain genetic modifications resulting in changes to the amino acid sequence of proteins, will result in changes in the relative catalytic activity (as measured by Vmax or Vmax/Km) of a type II fatty acid biosynthetic pathway enzyme. Thus, in some embodiments, increasing the level of type II fatty acid biosynthetic pathway enzyme activity comprises increasing the catalytic activity, on a per cell basis, of the type II fatty acid biosynthetic pathway enzyme by at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, compared to the type II fatty acid biosynthetic pathway enzyme activity in the parent host cell. Growth of genetically modified host cells is readily determined using well-known methods, e.g., optical density (OD) measurement at about 600 nm ($OD_{600}$) of liquid cultures of bacteria; colony size; growth rate; and the like.

Modulating Cell Culture Conditions

In some embodiments, the present invention provides methods of reducing HMG-CoA accumulation-induced toxicity; and methods of increasing isoprenoid or isoprenoid precursor compound production in a host cell, where the methods generally involve modulating cell culture conditions. For example, in some embodiments, a subject method involves culturing a host cell that exhibits HMG-CoA accumulation-induced growth inhibition in a culture medium comprising one or more supplements, such that, when grown in the supplemented culture medium, the host cell exhibits reduced HMG-CoA accumulation-induced growth inhibition, compared to when the host cell is grown in control culture medium not comprising the supplement(s). In some embodiments, modulating cell culture conditions involves including in the cell culture medium a fatty acid or a compound that is metabolized in the host cell or broken down in the culture medium to yield a fatty acid and/or including in the culture medium one or more agents that increase osmolarity of the culture medium.

The present invention provides a method of producing an isoprenoid or an isoprenoid precursor in a genetically modified host cell (e.g., a prokaryotic cell cultured in vitro). In some embodiments, the methods involve culturing a genetically modified host cell (e.g., a plurality of genetically modified host cells) in vitro in a culture medium comprising a $C_{12}$-$C_{22}$ fatty acid. The genetically modified host cells are genetically modified with one or more nucleic acids comprising nucleotide sequences encoding heterologous mevalonate pathway enzymes that convert acetyl-CoA to isopentenyl pyrophosphate. The genetically modified host cell includes an endogenous type II fatty acid biosynthetic pathway.

The genetically modified host cells are cultured in a medium supplemented with one or more $C_{12}$-$C_{22}$ fatty acids. In some embodiments, the $C_{12}$-$C_{22}$ fatty acid is a $C_{12}$ saturated fatty acid. In other embodiments, the $C_{12}$-$C_{22}$ fatty acid is a $C_{14}$ saturated fatty acid. In other embodiments, the $C_{12}$-$C_{22}$ fatty acid is a $C_{16}$ saturated fatty acid. In other embodiments, the $C_{12}$-$C_{22}$ fatty acid is a $C_{18}$ is saturated fatty acid. In other embodiments, the $C_{12}$-$C_{22}$ fatty acid is a $C_{20}$ saturated fatty acid. In other embodiments, the $C_{12}$-$C_{22}$ fatty acid is a $C_{22}$ saturated fatty acid. Suitable $C_{12}$-$C_{22}$ fatty acids are described in more detail below. In an exemplary embodiment, the fatty acid is palmitic acid.

The isoprenoid or isoprenoid precursor is produced in the genetically modified host cell(s) at a level that is higher than the level of the isoprenoid or isoprenoid precursor that would be produced by the genetically modified host cell(s) when cultured in a control culture medium not comprising a $C_{12}$-$C_{22}$ fatty acid. Thus, e.g., when the genetically modified host cell is cultured in a medium comprising one or more $C_{12}$-$C_{22}$ fatty acids, the isoprenoid or isoprenoid precursor is produced in the genetically modified host cell(s) at a level that is at least about 10%, at least about 20%, at least about 50%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, higher than the level of the isoprenoid or isoprenoid precursor that would be produced by the genetically modified host cell when cultured in a control culture medium not supplemented with the one or more $C_{12}$-$C_{22}$ fatty acids. In some embodiments, a subject method provides for production of an isoprenoid or isoprenoid precursor in a recoverable amount of from about 1 mg/L to about 50 g/L, e.g., from about 1 mg/L to about 5 mg/L, from about 5 mg/L to about 10 mg/L, from about 10 mg/L to about 25 mg/L, from about 25 mg/L to about 50 mg/L, from about 50 mg/L to about 100 mg/L, from about 100 mg/L to about 250 mg/L, from about 250 mg/L to about 500 mg/L, from about 500 mg/L to about 1 g/L, from about 1 g/L to about 5 g/L, from about 5 g/L to about 10 g/L, from about 10 g/L to about 15 g/L, from about 15 g/L to about 20 g/L, from about 20 g/L to about 25 g/L, from about 25 g/L to about 30 g/L, from about 30 g/L to about 40 g/L, or from about 40 g/L to about 50 g/L.

In some embodiments, the culture medium further comprises a supplement that increases the osmolarity compared to the osmolarity of the control culture medium. Suitable supplements are described in more detail below. In some embodiments, the supplement is a salt in a concentration range of from about 50 mM to about 500 mM.

The present invention provides a method of producing an isoprenoid or an isoprenoid precursor in a genetically modified host cell (e.g., a prokaryotic cell cultured in vitro). In some embodiments, the methods involve culturing a genetically modified host cell (e.g., a plurality of genetically modified host cells) in vitro in a culture medium comprising a supplement that increases the osmolarity compared to the osmolarity of a control culture medium. The genetically modified host cells are genetically modified with one or more nucleic acids comprising nucleotide sequences encoding heterologous mevalonate pathway enzymes that convert acetyl-CoA to isopentenyl pyrophosphate. The isoprenoid or isoprenoid precursor is produced in the genetically modified host cell(s) at a level that is higher than the level of the isoprenoid or isoprenoid precursor that would be produced by the genetically modified host cell(s) when cultured in a control culture medium not comprising the supplement that increases osmolarity. Thus, e.g., when the genetically modified host cell is cultured in a medium comprising the supplement that increased the osmolarity of the culture medium the isoprenoid or isoprenoid precursor is produced in the genetically modified host cell(s) at a level that is at least about 10%, at least about 20%, at least about 50%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, higher than the level of the isoprenoid or isoprenoid precursor that would be produced by the genetically modified host cell when cultured in a control culture medium not supplemented with the supplement that increased the osmolarity of the culture medium. In some embodiments, the supplement is a salt in a concentration range of from about 50 mM to about 500 mM. In some embodiments, a subject method provides for production of an isoprenoid or isoprenoid precursor in a recoverable amount of from about 1 mg/L to about 50 g/L, e.g., from about 1 mg/L to about 5 mg/L, from about 5 mg/L to about 10 mg/L, from about 10 mg/L to about 25 mg/L, from about 25 mg/L to about 50 mg/L, from about 50 mg/L to about 100 mg/L, from about 100 mg/L to about 250 mg/L, from about 250 mg/L to about 500 mg/L, from about 500 mg/L to about 1 g/L, from about 1 g/L to about 5 g/L, from about 5 g/L to about 10 g/L, from about 10 g/L to about 15 g/L, from about 15 g/L to about 20 g/L, from about 20 g/L to about 25 g/L, from about 25 g/L to about 30 g/L, from about 30 g/L to about 40 g/L, or from about 40 g/L to about 50 g/L.

In some embodiments, a supplemented culture medium comprises one or more fatty acids; a salt of a fatty acid; a fatty acid derivative; a salt of a fatty acid derivative; a compound that can be broken down in the culture medium to yield a fatty acid; or a compound that can be metabolized in the cell to yield a fatty acid. In some embodiments, a supplemented culture medium comprises one or more saturated fatty acids, a salt of a saturated fatty acid, a derivative of a saturated fatty acid, or a salt of a saturated fatty acid derivative. In other embodiments, a supplemented culture medium comprises one or more unsaturated fatty acids, a salt of an unsaturated fatty acid, a derivative of an unsaturated fatty acid, or a salt of an unsaturated fatty acid derivative. In other embodiments, a supplemented culture medium comprises one or more saturated fatty acids, or a salt or a derivative thereof; and one or more unsaturated fatty acids, or a salt or a derivative thereof.

Suitable fatty acids include, but are not limited to, $C_{12}$-$C_{22}$ fatty acids. In some embodiments, the fatty acid is a saturated fatty acid. In other embodiments, the fatty acid is an unsaturated fatty acid. Suitable saturated fatty acids include, but are not limited to, $C_{12}$-$C_{22}$ saturated fatty acids, e.g. $C_{12}$ saturated fatty acids, $C_{14}$ saturated fatty acids, $C_{16}$ saturated fatty acids, $C_{18}$ saturated fatty acids, $C_{20}$ saturated fatty acids, and $C_{22}$ saturated fatty acids. Suitable saturated fatty acids include, but are not limited to, myristic acid (tetradecanoic acid), pentadecanoic acid, palmitic acid (hexadecanoic acid), stearic acid (octadecanoic acid), arachidic acid (eicosanoic acid), docosanoic acid, and tetracosanoic acid. Also suitable for use are salts of a saturated fatty acid, derivatives of a saturated fatty acid, and salts of a derivative of a saturated fatty acid. Suitable salts include, but are not limited to, lithium salts, potassium salts, sodium salts, and the like.

Suitable unsaturated fatty acids include, but are not limited to, oleic acid, vaccenic acid, linoleic acid, palmitelaidic acid, and arachidonic acid. Also suitable for use are salts of an unsaturated fatty acid, derivatives of an unsaturated fatty acid, and salts of a derivative of an unsaturated fatty acid. Suitable salts include, but are not limited to, lithium salts, potassium salts, sodium salts, and the like.

In other embodiments, a supplemented culture medium comprises a lipid or a triglyceride, or other compound that is taken up into the host cell and metabolized to release a fatty acid.

In some embodiments, the culture medium will include an agent that provides for solubilization of a fatty acid (or lipid, triglyceride, etc.). Suitable solubilizing agents include surfactants, a variety of which are known to those skilled in the art, and include biocompatible nonionic surfactants such as Brij (e.g., polyoxyethylene (4) lauryl ether, also known as Brij-30; polyoxyethylene (2) oleyl ether; polyoxyethylene (2) stearyl ether; etc.); micelles; and the like. For example, in some embodiments, the fatty acid is mixed with a biocompatible nonionic surfactant, and the mixture is added to the culture medium.

The fatty acid (or compound that yields a fatty acid) will in some embodiments be present in the culture medium in an amount or a concentration that is effective to reduce HMG-CoA accumulation-induced growth inhibition of the cell. In some embodiments, the culture medium comprises a fatty acid in a concentration range of from about 0.10 mM to about 0.50 mM, e.g., from about 0.1 mM to about 0.15 mM, from about 0.15 mM to about 0.2 mM, from about 0.2 mM to about 0.25 mM, from about 0.25 mM to about 0.3 mM, from about 0.3 mM to about 0.35 mM, from about 0.3 M to about 0.4 mM, from about 0.35 mM to about 0.4 mM, from about 0.35 mM to about 0.45 mM, or from about 0.45 mM to about 0.5 mM.

In other embodiments, a supplemented culture medium comprises one or more agents that increase osmolarity of the culture medium. An agent(s) that increases osmolarity is present in the culture medium at a concentration that increases the osmolarity of the culture medium by at least about 10%, at least about 20%, at least about 25%, at least about 50%, at least about 75%, at least about 100% (or 2-fold), at least about 2.5 fold, at least about 3 fold, at least about 3.5 fold, at least about 4 fold, at least about 5 fold, at least about 10 fold, at least about 25 fold, at least about 50 fold, at least about 100 fold, at least about 200 fold, at least about 300 fold, at least about 400 fold, or at least about 500 fold, or more, compared to the osmolarity of a control culture medium, e.g., a culture medium in which cells exhibit HMG-CoA accumulation-induced toxicity (e.g., cell growth inhibition).

For example, in some embodiments the osmolarity of control culture medium is from about 50 mOsM to about 100 mOsM; and a supplemented culture medium comprising one or more agents that increase osmolarity has an osmolarity of from about 100 mOsM to about 500 mOsM, e.g., from about 100 mOsM to about 110 mOsM, from about 100 mOsM to about 125 mOsM, from about 125 mOsM to about 150 mOsM, from about 150 mOsM to about 200 mOsM, from about 200 mOsM to about 250 mOsM, from about 250 mOsM to about 300 mOsM, from about 300 mOsM to about 350 mOsM, from about 350 mOsM to about 400 mOsM, from about 400 mOsM to about 450 mOsM, or from about 450 mOsM to about 500 mOsM, or greater than 500 mOsM.

Agents that increase osmolarity include, but are not limited to, salts, sugars (e.g. monosaccharides such as glucose; disaccharides; etc.), sugar alcohols, starches, polysaccharides, glycerol, and the like. Suitable salts include, but are not limited to, NaCl, sodium citrate, $Na_2HPO_4$, $CaCl_2$, KCl, $KH_2PO_4$, $K_2HPO_4$, $NH_4Cl$, $MgSO_4$, and the like. Suitable sugars and sugar alcohols include sorbitol, trehalose, and the like.

In some embodiments, the culture medium comprises a salt, a sugar, or a sugar alcohol in a concentration range of from about 50 mM to about 500 mM, e.g., from about 50 mM to about 75 mM, from about 75 mM to about 100 mM, from about 100 mM to about 125 mM, from about 125 mM to about 150 mM, from about 150 mM to about 175 mM, from about 175 mM to about 200 mM, from about 200 mM to about 250 mM, from about 250 mM to about 300 mM, from about 300 mM to about 350 mM, from about 350 mM to about 400 mM, from about 400 mM to about 450 mM, or from about 450 mM to about 500 mM.

Increasing Isoprenoid or Isoprenoid Precursor Production

The above-described methods result in relief from HMG-CoA accumulation-induced toxicity and/or cell growth inhibition in a cell; and provide for increased production of an isoprenoid compound and/or an isoprenoid precursor compound in the cell. Thus, the present invention provides methods for increasing production of an isoprenoid compound or an isoprenoid precursor compound in a cell, where the methods generally involve modulating the activity levels of a fatty acid biosynthetic pathway enzyme in the cell and/or modulating fatty acid composition (or lipid or triglyceride composition) of the culture medium and/or modulating osmolarity of the culture medium, such that HMG-CoA accumulation-induced toxicity and/or growth inhibition is reduced, and such that production of an isoprenoid compound or an isoprenoid precursor compound is increased, either on a per cell basis, on a per unit volume of cell culture basis, or on a per cell mass basis.

The present invention provides methods for increasing production of an isoprenoid compound, or an isoprenoid compound precursor (e.g., mevalonate, IPP, a polyprenyl disphosphate, etc.) by a cell or cultures of a cell. The methods generally involve increasing the activity level of a fatty acid biosynthetic pathway enzyme in the cell and/or modulating fatty acid composition of the culture medium and/or modulating osmolarity of the culture medium, where the parent cell exhibits HMG-CoA accumulation-induced cell growth inhibition. A cell that exhibits HMG-CoA accumulation-induced cell growth inhibition is in some embodiments a parent host cell that does not normally synthesize IPP or mevalonate via a mevalonate pathway, and that has been genetically modified with one or more nucleic acids comprising nucleotide sequences encoding mevalonate pathway enzyme(s), which enzymes are produced at levels that result in accumulation of toxic or growth inhibiting levels of HMG-CoA in the cell. A cell that exhibits HMG-CoA accumulation-induced cell growth inhibition is in some embodiments a parent host cell that does normally synthesize IPP or mevalonate via a mevalonate pathway, but that is genetically modified such that intracellular HMG-CoA accumulates at growth inhibiting or toxic levels. In one embodiment, the compound is the isoprenoid precursor compound IPP. In one embodiment, the host cell is an *E. coli* cell. In another embodiment, the host cell is a yeast cell.

In some embodiments, increasing the activity level of a fatty acid biosynthetic pathway enzyme in the cell and/or modulating fatty acid composition of the culture medium and/or modulating osmolarity of the culture medium increases mevalonate production by the genetically modified host cell, or by a culture of the genetically modified host cell. Thus, in some embodiments, increasing the activity level of a fatty acid biosynthetic pathway enzyme in the cell and/or modulating fatty acid composition of the culture medium and/or modulating osmolarity of the culture medium increases mevalonate production by at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, in the genetically modified host cell, compared to the parent host cell. Mevalonate production is readily determined using well-known methods, e.g., gas chromatography-mass spectrometry, liquid chromatography-mass spectrometry, ion chromatography-mass spectrometry, thin layer chromatography, pulsed amperometric detection, uv-vis spectrometry, and the like.

In some embodiments, increasing the activity level of a fatty acid biosynthetic pathway enzyme in the cell and/or modulating fatty acid composition of the culture medium and/or modulating osmolarity of the culture medium increases IPP production by the genetically modified host cell, or by a culture of the genetically modified host cell. Thus, in some embodiments, increasing the activity level of a fatty acid biosynthetic pathway enzyme in the cell and/or modulating fatty acid composition of the culture medium and/or modulating osmolarity of the culture medium increases IPP production by at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, in the genetically modified host cell, compared to the parent host cell. IPP production is readily determined using well-known methods, e.g., liquid chromatography-mass spectrometry, thin layer chromatography, ion chromatography-mass spectrometry, pulsed amperometric detection, uv-vis spectrometry, and the like.

In some embodiments, increasing the activity level of a fatty acid biosynthetic pathway enzyme in the cell and/or modulating fatty acid composition of the culture medium and/or modulating osmolarity of the culture medium increases isoprenoid production by the genetically modified host cell. Thus, in some embodiments, increasing the activity level of a fatty acid biosynthetic pathway enzyme in the cell and/or modulating fatty acid composition of the culture medium and/or modulating osmolarity of the culture medium increases isoprenoid production by at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, in the genetically modified host cell, compared to the parent host cell. Isoprenoid production is readily determined using well-known methods, e.g., gas chromatography-mass spectrometry, liquid chromatography-mass spectrometry, ion chromatography-mass spectrometry, pulsed amperometric detection, uv-vis spectrometry, and the like.

In some embodiments, a subject method provides for enhanced production of isoprenoid or isoprenoid precursor per cell, e.g., the amount of isoprenoid or isoprenoid precursor compound produced using a subject method is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, higher than the amount of the isoprenoid or isoprenoid precursor compound produced by a control parent cell, on a per cell basis. Amount of cells measured by measuring dry cell weight or measuring optical density of the cell culture.

In other embodiments, a subject method provides for enhanced production of isoprenoid or isoprenoid precursor per unit volume of cell culture, e.g., the amount of isoprenoid or isoprenoid precursor compound produced using a subject method is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, higher than the amount of the isoprenoid or isoprenoid precursor compound produced by a control parent cell, on a per unit volume of cell culture basis.

Isoprenoids that can be produced using the method of the invention include, but are not limited to, monoterpenes, including but not limited to, limonene, citronellol, geraniol, menthol, perillyl alcohol, linalool, thujone; sesquiterpenes, including but not limited to, periplanone B, gingkolide B, amorphadiene, artemisinin, artemisinic acid, valencene, nootkatone, epi-cedrol, epi-aristolochene, framesol, gossypol, sanonin, periplanone, santatol, and forskolin; diterpenes, including but not limited to, casbene, eleutherobin, paclitaxel, prostratin, and pseudopterosin; triterpenes, including but not limited to, arbruside E, bruceantin, testosterone, progesterone, cortisone, digitoxin. Isoprenoids also include, but are not limited to, carotenoids such as lycopene, $\alpha$- and $\beta$-carotene, $\alpha$- and $\beta$-cryptoxanthin, bixin, zeaxanthin, astaxanthin, and lutein. Isoprenoids also include, but are not limited to, triterpenes, steroid compounds, and compounds that are composed of isoprenoids modified by other chemical groups, such as mixed terpene-alkaloids, and coenzyme Q-10.

A subject method is useful for production of a variety of isoprenoid or isoprenoid precursor compounds, as noted above. A host cell that is genetically modified with a nucleic acid comprising a nucleotide sequence encoding a fatty acid biosynthetic pathway enzyme, as described above, is in many embodiments cultured in vitro in a suitable medium and at a suitable temperature. The temperature at which the cells are cultured is generally from about 18° C. to about 40° C., e.g., from about 18° C. to about 20° C., from about 20° C. to about 25° C., from about 25° C. to about 30° C., from about 30° C. to about 35° C., or from about 35° C. to about 40° C. (e.g., at about 37° C.).

In some embodiments, a subject method of producing an isoprenoid or isoprenoid precursor compound comprises culturing a genetically modified host cell, as described above; and further comprises recovering the isoprenoid or isoprenoid precursor compound. An isoprenoid or isoprenoid produced by the genetically modified host cell can be recovered (e.g., isolated, purified) from a cell lysate, from a cell supernatant, or both cell lysate and cell supernatant. Methods of recovering an isoprenoid or isoprenoid precursor compound from cell lysate and from cell supernatant (e.g., from cell culture medium) are known in the art. For example, a genetically modified prokaryotic cell can be sonicated, subjected to detergent lysis, or subjected to another method for releasing the contents of the cytosol. An isoprenoid or isoprenoid precursor compound can be recovered from the cell culture medium and/or a cell lysate using any of a variety of methods, including, but not limited to, high performance liquid chromatography (HPLC), size exclusion chromatography, and the like. In some embodiments, an isoprenoid or isoprenoid precursor compound is secreted from the genetically modified host cell, and is captured in an organic solvent which overlays the cell culture medium; in these embodiments, the isoprenoid or isoprenoid precursor compound can be recovered from the organic solvent.

In some embodiments, the host cell that is genetically modified with a nucleic acid comprising a nucleotide sequence encoding a fatty acid biosynthetic pathway enzyme is cultured in a suitable medium (e.g., Luria-Bertoni broth, optionally supplemented with one or more additional agents, such as an inducer (e.g., where the fatty acid biosynthetic pathway enzyme-encoding nucleotide sequence is under the control of an inducible promoter), etc.); and the culture medium is overlaid with an organic solvent, e.g. dodecane, forming an organic layer. The isoprenoid compound produced by the genetically modified host cell partitions into the organic layer, from which it can be purified. In some embodiments, where the isoprenoid-modifying enzyme-encoding nucleotide sequence is operably linked to an inducible promoter, an inducer is added to the culture medium; and, after a suitable time, the isoprenoid compound is isolated from the organic layer overlaid on the culture medium.

In some embodiments, the isoprenoid or isoprenoid precursor compound will be separated from other products which may be present in the organic layer. Separation of the isoprenoid compound from other products that may be present in the organic layer is readily achieved using, e.g., standard chromatographic techniques.

In some embodiments, the isoprenoid or isoprenoid precursor compound that is recovered is pure, e.g., at least about 40% pure, at least about 50% pure, at least about 60% pure, at least about 70% pure, at least about 80% pure, at least about 90% pure, at least about 95% pure, at least about 98%, or more than 98% pure, where "pure" in the context of an isoprenoid compound refers to an isoprenoid compound that is free from other isoprenoid or isoprenoid precursor compounds, macromolecules, contaminants, etc.

Genetically Modified Host Cells

The present invention provides genetically modified host cells; and compositions comprising the genetically modified host cells. The genetically modified host cells are useful for producing an isoprenoid compound or an isoprenoid precursor compound, as discussed above.

As discussed above, a subject method for producing an isoprenoid or isoprenoid precursor generally involves culturing a genetically modified host cell in a suitable medium. In some embodiments, the genetically modified host cell is one that has been genetically modified with one or more heterologous nucleic acids comprising nucleotide sequences encoding a type I or a type II fatty acid biosynthetic pathway enzymes that, when produced in the cell, relieves HMG-CoA accumulation-induced growth inhibition (toxicity) in the cell, and that results in increased production of isoprenoid or isoprenoid precursor compound in the genetically modified cell or in a population of the genetically modified cells. The parent cell (e.g., the cell not genetically modified with one or more heterologous nucleic acids comprising nucleotide sequences encoding one or more fatty acid biosynthetic enzymes) is in some embodiments a cell that produces, or is genetically modified to produce, IPP via a mevalonate pathway.

Thus, e.g., a "parent" (or "parental") host cell is genetically modified to include one or more nucleic acids heterologous to the host cell, where the one or more nucleic acids comprise nucleotide sequences encode a fatty acid biosynthetic pathway enzyme. The parent host cell produces IPP via a mevalonate pathway and/or produces mevalonate via a mevalonate pathway. The parent cell comprises, or is genetically modified to comprise, nucleic acids comprising nucleotide sequences encoding one or more enzymes in the mevalonate pathway (and produces IPP via the mevalonate pathway and/or produces mevalonate via a mevalonate pathway). A parent cell that has been genetically modified to include one or more nucleic acids heterologous to the host cell, where the one or more nucleic acids comprise nucleotide sequences encoding a fatty acid biosynthetic pathway enzyme, is referred to as a "genetically modified host cell." HMG-CoA accumulation-induced growth inhibition in the genetically modified parent host cell is reduced, compared a parent host cell not genetically modified with the one or more heterologous nucleic acids comprising nucleotide sequences encoding the fatty acid biosynthetic pathway enzyme. Further the genetically modified host cell exhibits increased levels of mevalonate or isoprenoid products derived from a combination of increased per cell production of mevalonate and/or increased cell viability. It is understood that this invention can be iteratively applied to incrementally increase production of isoprenoid compounds so that in one context a particular cell line may be a genetically modified host cell and then in a later context it may be a parent host cell utilized as a starting point for further improvement.

In some embodiments, the parent cell is a cell that does not normally produce IPP or mevalonate via the mevalonate pathway; e.g., the parent cell is one that has been genetically modified with one or more heterologous nucleic acids comprising nucleotide sequences encoding one or more enzymes in the mevalonate pathway. As an example, a parent cell is a prokaryotic cell that does not normally produce IPP or mevalonate via the mevalonate pathway, and that has been genetically modified with one or more nucleic acids comprising nucleotide sequences encoding acetoacetyl-CoA thiolase, HMGS, and HMGR, where the levels of acetoacetyl-CoA thiolase and HMGS activity are such that HMG-CoA accumulates intracellularly at a level that is growth inhibiting or toxic. An example is an *E. coli* cell that has been genetically modified with a pBAD24MevT construct comprising a nucleotide sequence as set forth in SEQ ID NO:1 of U.S. Pat. No. 7,183,089. A second example of a parent host cell is an *E. coli* cell that has been genetically modified with a pBAD33MevT construct comprising a nucleotide sequence as set forth in SEQ ID NO:2 of U.S. Pat. No. 7,183,089.

In some embodiments, the present invention provides a genetically modified host cell, where the genetically modified host cell comprises is genetically modified with at least one heterologous nucleic acid encoding a mevalonate pathway enzyme and a type II fatty acid biosynthetic enzyme; and where the genetically modified host cell comprises an endogenous type II fatty acid biosynthetic pathway. In some embodiments, the genetically modified host cell comprises all of the enzymes of the mevalonate pathway that convert acetyl-CoA to isopentenyl pyrophosphate. In some embodiments, the at least one heterologous nucleic acid encodes acetoacetyl-CoA thiolase, hydroxymethylglutaryl-CoA synthase, hydroxymethylglutaryl-CoA reductase, mevalonate kinase, phosphomevalonate kinase, mevalonate pyrophosphate decarboxylase, isopentenyl pyrophosphate isomerase, and a prenyl transferase. In some embodiments, the type II fatty acid biosynthetic enzyme is an enzyme that converts malonyl-CoA to malonyl-ACP. In some embodiments, the type II fatty acid biosynthetic enzyme is malonyl-CoA:ACP transferase. In some embodiments, the type II fatty acid biosynthetic enzyme is FadD. In some embodiments, the at least one heterologous nucleic acid encodes a plurality of type II fatty acid biosynthetic enzymes. In some embodiments, the plurality of type II fatty acid biosynthetic enzymes includes an enzyme that converts malonyl-CoA to malonyl-ACP and an enzyme that converts acyl-ACP to β-ketoacyl-ACP. In some embodiments, the plurality of type II fatty acid biosynthetic enzymes includes malonyl-CoA:ACP transferase and β-ketoacyl-ACP synthase I. In some embodiments, the plurality of type II fatty acid biosynthetic enzymes includes FadD and FadB. In some embodiments, a subject genetically modified host cell, when cultured in an appropriate culture medium (e.g., a culture medium as described above), produces an isoprenoid or isoprenoid precursor in a recoverable amount of from about 1 mg/L to about 50 g/L, e.g., from about 1 mg/L to about 5 mg/L, from about 5 mg/L to about 10 mg/L, from about 10 mg/L to about 25 mg/L, from about 25 mg/L to about 50 mg/L, from about 50 mg/L to about 100 mg/L, from about 100 mg/L to about 250 mg/L, from about 250 mg/L to about 500 mg/L, from about 500 mg/L to about 1 g/L, from about 1 g/L to about 5 g/L, from about 5 g/L to about 10 g/L, from about 10 g/L to about 15 g/L, from about 15 g/L to about 20 g/L, from about 20 g/L to about 25 g/L, from about 25 g/L to about 30 g/L, from about 30 g/L to about 40 g/L, or from about 40 g/L to about 50 g/L.

To generate a subject genetically modified host cell, one or more nucleic acids comprising nucleotide sequences encoding fatty acid biosynthetic pathway enzyme(s) is introduced stably or transiently into a parent host cell, using established techniques, including, but not limited to, electroporation, calcium phosphate precipitation, DEAE-dextran mediated transfection, liposome-mediated transfection, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like.

Mevalonate Pathway Enzymes

As noted above, a parent cell is a host cell that produces, or is genetically modified to produce, IPP via a mevalonate pathway and/or mevalonate via a mevalonate pathway, and that exhibits HMG-CoA accumulation-induced toxicity or growth inhibition. The mevalonate pathway comprises: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate. The mevalonate pathway enzymes required for production of IPP vary, depending on the culture conditions.

In some embodiments, a parent host cell is one that has been genetically modified with one or more heterologous nucleic acids comprising nucleotide sequences encoding acetoacetyl-CoA thiolase, HMGS, and HMGR, and the parent host cell is one that produces mevalonate. An non-limiting example of a parent host cell is an *E. coli* cell that has been genetically modified with a construct comprising a nucleotide sequence as set forth in SEQ ID NO:1 of U.S. Pat. No. 7,183,089 (pBAD24MevT) or a nucleotide sequence encoding enzymes functionally analogous to those enzymes encoded in SEQ ID NO:1 of U.S. Pat. No. 7,183,089. A further non-limiting example of a parent host cell is an *E. coli* cell that has been genetically modified with a construct comprising a nucleotide sequence as set forth in SEQ ID NO:2 of U.S. Pat. No. 7,183,089 (pBAD33MevT) or a nucleotide sequence encoding enzymes functionally analogous to those enzymes encoded in SEQ ID NO:2 of U.S. Pat. No. 7,183,089.

In other embodiments, a parent host cell is one that has been genetically modified with one or more heterologous nucleic acids comprising nucleotide sequences encoding acetoacetyl-CoA thiolase, HMGS, HMGR, mevalonate kinase (MK), phosphomevalonate kinase (PMK), and mevalonate pyrophosphate decarboxylase (MPD) (and optionally also IPP isomerase). An example of a parent host cell is an *E. coli* cell that has been genetically modified with a construct comprising a nucleotide sequence as set forth in SEQ ID NO:2 of U.S. Pat. No. 7,183,089 (pBAD33MevT) and SEQ ID NO: 4 of U.S. Pat. No. 7,183,089 (pMBIS). A further example of a parent host cell is an *E. coli* cell that has been genetically modified with a construct comprising a nucleotide sequence as set forth in SEQ ID NO:3 of U.S. Pat. No. 7,183,089 (pMevT) and SEQ ID NO: 4 of U.S. Pat. No. 7,183,089 (pMBIS).

In some embodiments, a parent host cell is one that has been genetically modified with one or more heterologous nucleic acids comprising nucleotide sequences encoding mevalonate kinase (MK), phosphomevalonate kinase (PMK), and mevalonate pyrophosphate decarboxylase (MPD) (and optionally also isopentenyl pyrophosphate isomerase); and the parent host cell is cultured in medium that includes mevalonate.

In other embodiments, a parent host cell is one that has been genetically modified with one or more heterologous nucleic acids comprising nucleotide sequences encoding acetoacetyl-CoA thiolase, hydroxymethylglutaryl-CoA synthase (HMGS), hydroxymethylglutaryl-CoA reductase (HMGR), MK, PMK, and MPD (and optionally also IPP isomerase).

In other embodiments, a parent host cell is one that has been genetically modified with one or more heterologous nucleic acids comprising nucleotide sequences encoding MK, PMK, MPD, IPP isomerase, and a prenyl transferase. In other embodiments, a parent host cell is one that is genetically modified with one or more heterologous nucleic acids comprising nucleotide sequences encoding acetoacetyl-CoA thiolase, HMGS, HMGR, MK, PMK, MPD, IPP isomerase, and a prenyl transferase. An example of a parent host cell is an *E. coli* cell that has been genetically modified with a construct comprising a nucleotide sequence as set forth in SEQ ID NO:2 of U.S. Pat. No. 7,183,089 (pBAD33MevT), SEQ ID NO: 4 of U.S. Pat. No. 7,183,089 (pBMIS) and SEQ ID NO: 5 of U.S. Pat. No. 7,183,089 (pADS). A further example is an *E. coli* cell that has been genetically modified with a construct comprising a nucleotide sequence as set forth in SEQ ID NO: 1 of U.S. Pat. No. 7,183,089 (pBAD24MevT) and SEQ ID NO: 4 of U.S. Pat. No. 7,183,089 (pBMIS) and SEQ ID NO: 5 of U.S. Pat. No. 7,183,089 (pADS).

Suitable host cells (including parent host cells and genetically modified host cells) are in many embodiments unicellular organisms, or are grown in culture as single cells. In some embodiments, the host cell is a eukaryotic cell. Suitable eukaryotic host cells include, but are not limited to, yeast cells, insect cells, plant cells, fungal cells, and algal cells. Suitable eukaryotic host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like. In some embodiments, the host cell is a eukaryotic cell other than a plant cell.

In other embodiments, the host cell is a prokaryotic cell. Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol* 148:1176-1181; U.S. Pat. No. 6,447,784; and Sizemore et al. (1995) *Science* 270: 299-302. Examples of *Salmonella* strains which can be employed in the present invention include, but are not limited to, *Salmonella typhi* and *S. typhimurium*. Suitable *Shigella* strains include, but are not limited to, *Shigella flexneri*, *Shigella sonnei*, and *Shigella disenteriae*. Typically, the laboratory strain is one that is non-pathogenic. Non-limiting examples of other suitable bacteria include, but are not limited to, *Bacillus subtilis*, *Pseudomonas pudita*, *Pseudomonas aeruginosa*, *Pseudomonas mevalonii*, *Rhodobacter sphaeroides*, *Rhodobacter capsulatus*, *Rhodospirillum rubrum*, *Rhodococcus* sp., and the like. In some embodiments, the host cell is *Escherichia coli*.

As noted above, in some embodiments, a parent host cell is one that has been genetically modified with one or more heterologous nucleic acids comprising nucleotide sequences encoding mevalonate pathway enzyme(s). To genetically modify a parent host cell such that it produces IPP via a mevalonate pathway and/or that produces mevalonate via a mevalonate pathway, one or more nucleic acids comprising nucleotide sequences encoding one or more mevalonate pathway enzymes is introduced stably or transiently into a host cell, using established techniques, including, but not limited to, electroporation, calcium phosphate precipitation, DEAE-dextran mediated transfection, liposome-mediated transfection, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like.

In many embodiments, the nucleic acid with which the host cell is genetically modified such that it produces IPP and/or mevalonate via a mevalonate pathway is an expression vector that includes a nucleic acid comprising a nucleotide sequence that encodes a mevalonate pathway enzyme(s). Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as *E. coli* and yeast). Thus, for example, a nucleic acid encoding a mevalonate pathway gene product(s) is included in any one of a variety of expression vectors for expressing the mevalonate pathway gene product(s). Such vectors include chromosomal, nonchromosomal and synthetic DNA sequences.

Numerous suitable expression vectors are known to those of skill in the art, and many are commercially available. The following vectors are provided by way of example; for bacterial host cells: pQE vectors (Qiagen), pBluescript plasmids, pNH vectors, lambda-ZAP vectors (Stratagene); pTrc99a, pKK223-3, pDR540, and pRIT2T (Pharmacia); for eukaryotic host cells: pXT1, pSG5 (Stratagene), pSVK3, pBPV, pMSG, and pSVLSV40 (Pharmacia). However, any other plasmid or other vector may be used so long as it is compatible with the host cell.

For generating a parent host cell comprising one or more heterologous nucleic acids comprising nucleotide sequences encoding mevalonate pathway enzymes, a mevalonate pathway enzyme-encoding nucleotide sequence is inserted into an expression vector. The mevalonate pathway enzyme-encoding nucleotide sequence in the expression vector is operably linked to an appropriate expression control sequence(s) (e.g., a promoter) to direct synthesis of the encoded gene product. Similarly, for generating a genetically modified host cell from a parent host cell, an expression vector comprising nucleotide sequences encoding a fatty acid biosynthetic pathway enzyme will be used. The fatty acid biosynthetic pathway enzyme coding sequences are operably linked to appropriate expression control sequence(s) to direct synthesis of the encoded gene product. Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; a salicylate promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367-378); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035-7056); and the like.

Non-limiting examples of suitable eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

In addition, the expression vectors will in many embodiments contain one or more selectable marker genes to provide a phenotypic trait for selection of transformed host cells such as dihydrofolate reductase or neomycin resistance for eukaryotic cell culture, or such as tetracycline or ampicillin resistance in prokaryotic host cells such as *E. coli*.

Generally, recombinant expression vectors will include origins of replication and selectable markers permitting transformation of the host cell, e.g., the ampicillin resistance gene of *E. coli*, the *S. cerevisiae* TRP1 gene, etc.; and a promoter derived from a highly-expressed gene to direct transcription of the coding sequence. Such promoters can be derived from operons encoding glycolytic enzymes such as 3-phosphoglycerate kinase (PGK), α-factor, acid phosphatase, or heat shock proteins, among others.

In many embodiments, a parent host cell comprises a mevalonate pathway enzyme-encoding nucleotide sequence operably linked to an inducible promoter. Similarly, in many embodiments, a genetically modified host cell will comprise a fatty acid biosynthetic pathway enzyme-encoding nucleotide sequence operably linked to an inducible promoter. Inducible promoters are well known in the art. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (see, e.g., Guzman et al. (1995) *J. Bacteriol.* 177:4121-4130); a xylose-inducible promoter, e.g., Pxyl (see, e.g., Kim et al. (1996) *Gene* 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda $P_L$ promoter, a promoter controlled by a heat-sensitive repressor (e.g., CI857-repressed lambda-based expression vectors; see, e.g., Hoffmann et al. (1999) *FEMS Microbiol Lett.* 177(2):327-34); and the like.

In many embodiments, a parent host cell is generated by genetically modifying a host cell with a nucleic acid that includes a nucleotide sequence encoding a mevalonate pathway gene product, where the nucleotide sequence encoding a mevalonate pathway gene product is operably linked to a constitutive promoter. Similarly, in some embodiments, a fatty acid biosynthetic pathway enzyme coding sequence is operably linked to a constitutive promoter. Suitable constitutive promoters for use in prokaryotic cells are known in the art and include, but are not limited to, a sigma70 promoter, e.g., a consensus sigma70 promoter.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome.

Where a parent host cell has been genetically modified to produce two or more mevalonate pathway enzymes, nucleotide sequences encoding the two or more enzymes will in some embodiments each be contained on separate expression vectors. Where the host cell is genetically modified to express one or more mevalonate pathway enzymes, nucleotide sequences encoding the one or more mevalonate pathway enzymes will in some embodiments be contained in a single expression vector. Where nucleotide sequences encoding the one or more mevalonate pathway enzymes are contained in a single expression vector, in some embodiments, the nucleotide sequences will be operably linked to a common control element (e.g., a promoter), e.g., the common control element controls expression of all of the mevalonate pathway enzyme-encoding nucleotide sequences on the single expression vector.

Where nucleotide sequences encoding the mevalonate pathway enzyme(s) are contained in a single expression vector, in some embodiments, the nucleotide sequences will be operably linked to different control elements (e.g., a promoters), e.g., the different control elements control expression of each of the mevalonate pathway enzyme-encoding nucleotide sequences separately on a single expression vector.

Nucleotide Sequences Encoding Mevalonate Pathway Enzymes

Nucleotide sequences encoding MEV pathway gene products are known in the art, and any known MEV pathway gene product-encoding nucleotide sequence can used to generate a subject genetically modified host cell. For example, nucleotide sequences encoding acetoacetyl-CoA thiolase, HMGS, HMGR, MK, PMK, MPD, and IDI are known in the art. The following are non-limiting examples of known nucleotide sequences encoding MEV pathway gene products, with GenBank Accession numbers and organism following each MEV pathway enzyme, in parentheses: acetoacetyl-CoA thiolase: (NC_000913 REGION: 2324131.2325315; *E. coli*), (D49362; *Paracoccus denitrificans*), and (L20428; *Saccharomyces cerevisiae*); HMGS: NC_001145. complement 19061 . . . 20536; *Saccharomyces cerevisiae*), (X96617; *Saccharomyces cerevisiae*), (X83882; *Arabidopsis thaliana*), (AB037907; *Kitasatospora griseola*), and (BT007302; *Homo sapiens*); HMGR: (NM_206548; *Drosophila melanogaster*), (NM_204485; *Gallus gallus*), (AB015627; *Streptomyces sp.* KO-3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734 . . . 118898; *Saccharomyces cerevisiae*)); MK: (L77688; *Arabidopsis thaliana*), and (X55875; *Saccharomyces cerevisiae*); PMK: (AF429385; *Hevea brasiliensis*), (NM_006556; *Homo sapiens*), (NC_001145. complement 712315 . . . 713670; *Saccharomyces cerevisiae*); MPD: (X97557; *Saccharomyces cerevisiae*), (AF290095; *Enterococcus faecium*), and (U49260; *Homo sapiens*); and IDI: (NC_000913, 3031087 . . . 3031635; *E. coli*), and (AF082326; *Haematococcus pluvialis*).

Also suitable for use are mevalonate pathway enzymes of gram positive bacteria, e.g., as described in Wilding et al. (2000) *J. Bacteriol.* 182:4319-4327. Various mevalonate pathway enzyme-encoding nucleotide sequences are known in the art; and any known mevalonate pathway enzyme-encoding nucleotide sequence, or a functional variant thereof, can be used. See, e.g., *Streptococcus pneumoniae* MK, MPD, and PMK, GenBank Accession No. AF290099; *Streptococcus pneumoniae* HMGS and HMGR, GenBank Accession No. AF290098; *Enterococcus faecium* MK, PMK, and MPD, GenBank Accession No. AF290095; *Enterococcus faecium* HMGS, acetyl-CoA acetyltransferases, and HMGR, GenBank Accession No. AF290094; *Enterococcus faecalis* MK, MPD, and PMK, GenBank Accession No. AF290093; *Enterococcus faecalis* HMGS, acetyl-CoA acetyltransferases, and HMGR, GenBank Accession No. AF290092; *Staphylococcus aureus* MK, MPD, and PMK, GenBank Accession No. AF290087; *Staphylococcus aureus* HMGS and HMGR, GenBank Accession No. AF290086; *Streptococcus pyogenes* MK, MPD, and PMK, GenBank Accession No. AF290097; and *Streptococcus pyogenes* HMGS and HMGR, GenBank Accession No. AF290096.

In some embodiments, the HMGR coding region is set forth in SEQ ID NO: 13 of U.S. Pat. No. 7,183,089, which encodes a truncated form of HMGR ("tHMGR") that lacks the transmembrane domain of wild-type HMGR. The transmembrane domain of HMGR contains the regulatory portions of the enzyme and has no catalytic activity.

The coding sequence of any known MEV pathway enzyme may be altered in various ways known in the art to generate targeted changes in the amino acid sequence of the encoded enzyme. The amino acid of a variant MEV pathway enzyme will usually be substantially similar to the amino acid sequence of any known MEV pathway enzyme, i.e. will differ by at least one amino acid, and may differ by at least two, at least 5, at least 10, or at least 20 amino acids, but typically not more than about fifty amino acids. The sequence changes may be substitutions, insertions or deletions. For example, as described below, the nucleotide sequence can be altered for the codon bias of a particular host cell.

Fatty Acid Biosynthetic Pathway Enzymes

Type II fatty acid biosynthetic pathway enzymes include, but are not limited to, malonyl-CoA:ACP transacylase, β-ketoacyl-ACP synthase I, β-ketoacyl-ACP synthase II, β-ketoacyl-ACP synthase III, malonyl-ACP decarboxylase, β-ketoacyl-ACP reductase, β-hydroxyacyl-ACP dehydratase, and enoyl-ACP reductase. "ACP" is "acyl carrier protein." The source of the type II fatty acid biosynthetic pathway enzyme-encoding nucleotide sequence will in some embodiments be a naturally-occurring source. In other embodiments, the type II fatty acid biosynthetic pathway enzyme-encoding nucleotide sequence is synthetic.

In some embodiments, a type II fatty acid biosynthetic pathway enzyme-encoding nucleotide sequence has at least about 50%, at least about 60%, at least about 70%, at least about 75%, at least about 80%, at least about 85%, at least about 90%, at least about 95%, at least about 98%, or more, nucleotide sequence identity to the nucleotide sequence of a naturally-occurring type II fatty acid biosynthetic pathway enzyme-encoding nucleotide sequence.

For example, in some embodiments, a type II fatty acid biosynthetic pathway enzyme-encoding nucleotide sequence encodes a malonyl-CoA:ACP transacylase, and has at least about 50%, at least about 60%, at least about 70%, at least about 75%, at least about 80%, at least about 85%, at least about 90%, at least about 95%, at least about 98%, or more (e.g., 99%, 100%), nucleotide sequence identity to any one of the following sequences: 1) the nucleotide sequence of E. coli malonyl-CoA:ACP transacylase as depicted in FIG. 4A and set forth in GenBank Accession No. AE014075 (gene=FabD; locus tag c1361); 2) the nucleotide sequence of E. coli malonyl-CoA:ACP transacylase as set forth in nucleotides 532-1461 of the nucleotide sequence set forth in GenBank Accession No. M870040; 3) the nucleotide sequence of a Pseudomonas malonyl-CoA:ACP transacylase as set forth in GenBank Accession number AB025101; 4) the nucleotide sequence of a Streptomyces avermitilis MA-4680 malonyl-CoA:ACP transacylase as set forth in GenBank Accession No. NC_00315 (locus tag SAV5788; gene ID 1211344); 5) the nucleotide sequence of a Rhodobacter sphaeroides malonyl-CoA:ACP transacylase as set forth in GenBank Accession No. NC_007493 (locus tag RSP_2682; gene ID 3720373); 6) the nucleotide sequence of a Streptomyces coelicolor malonyl-CoA:ACP transacylase as set forth in GenBank Accession No. NC_003888 (locus tag SCO2387; gene ID 1097821); and 7) the nucleotide sequence of an Arabidopsis thaliana malonyl-CoA:ACP transacylase as set forth in GenBank Accession No. NC_003071 (locus tag AT2G30200; gene ID 817570).

In other embodiments, a type II fatty acid biosynthetic pathway enzyme-encoding nucleotide sequence encodes a β-ketoacyl-ACP synthase I, and has at least about 50%, at least about 60%, at least about 70%, at least about 75%, at least about 80%, at least about 85%, at least about 90%, at least about 95%, at least about 98%, or more (e.g., 99%, 100%), nucleotide sequence identity to any one of the following sequences: 1) the nucleotide sequence of E. coli β-ketoacyl-ACP synthase I as set forth in GenBank Accession No. M24427 (SEQ ID NO:3; or nucleotides 237-1457 of the sequence set forth in SEQ ID NO:3); 2) the nucleotide sequence of Pseudomonas putida β-ketoacyl-ACP synthase I as set forth in GenBank Accession No. NC_002947 (locus tag PP4175; gene ID 1042370); and 3) the nucleotide sequence of Rhodobacter sphaeroides β-ketoacyl-ACP synthase I as set forth in GenBank Accession No. NC_007493 (locus tag RSP_2777; gene ID 3720510).

In some embodiments, a type II fatty acid biosynthetic pathway enzyme-encoding nucleotide sequence encodes a type II fatty acid biosynthetic pathway enzyme having at least about 50%, at least about 60%, at least about 70%, at least about 75%, at least about 80%, at least about 85%, at least about 90%, at least about 95%, at least about 98%, or more (e.g., 99%, 100%), amino acid sequence identity to the amino acid sequence of a naturally-occurring type II fatty acid biosynthetic pathway enzyme.

For example, in some embodiments, a type II fatty acid biosynthetic pathway enzyme-encoding nucleotide sequence encodes a malonyl-CoA:ACP transacylase that has at least about 50%, at least about 60%, at least about 70%, at least about 75%, at least about 80%, at least about 85%, at least about 90%, at least about 95%, at least about 98%, or more (e.g., 99%, 100%), amino acid sequence identity to any one of the following amino acid sequences: 1) the amino acid sequence of E. coli malonyl-CoA:ACP transacylase as depicted in FIG. 4B and set forth in GenBank Accession No. AAN79832.1; 2) the amino acid sequence of E. coli malonyl-CoA-ACP transacylase as set forth in GenBank Accession No. CAA77658; 3) the amino acid sequence of Bacteroides fragilis malonyl-CoA:ACP transacylase as set forth in GenBank Accession No. CAH08050; 4) the amino acid sequence of Mycobacterium bovis malonyl-CoA:ACP transacylase as set forth in GenBank Accession No. NP_855916; 5) the amino acid sequence of Erwinia carotovora malonyl-CoA:ACP transacylase as set forth in GenBank Accession No. YP_049896; and 6) the amino acid sequence of a Pseudomonas malonyl-CoA:ACP transacylase as set forth in GenBank Accession No. BAA76353.

In other embodiments, a type II fatty acid biosynthetic pathway enzyme-encoding nucleotide sequence encodes a β-ketoacyl-ACP synthase I that has at least about 50%, at least about 60%, at least about 70%, at least about 75%, at least about 80%, at least about 85%, at least about 90%, at least about 95%, at least about 98%, or more (e.g., 99%, 100%), amino acid sequence identity to any one of the following amino acid sequences: 1) the amino acid sequence of E. coli β-ketoacyl-ACP synthase I as set forth in GenBank Accession No. AAC67304 (SEQ ID NO:4); 2) the amino acid sequence of Yersinia pestis β-ketoacyl-ACP synthase I as set forth in GenBank Accession No. CAC92996; and 3) the amino acid sequence of Erwinia carotovora β-ketoacyl-ACP synthase I as set forth in GenBank Accession No. CAG75962.

In some embodiments, a type II fatty acid biosynthetic pathway enzyme-encoding nucleotide sequence encodes a type II fatty acid biosynthetic pathway enzyme having at least about 50%, at least about 60%, at least about 70%, at least about 75%, at least about 80%, at least about 85%, at least about 90%, at least about 95%, at least about 98%, or more, amino acid sequence identity to the amino acid sequence of a naturally-occurring type II fatty acid biosynthetic pathway enzyme. For example, in some embodiments, a type II fatty acid biosynthetic pathway enzyme-encoding nucleotide sequence encodes a malonyl-CoA:ACP transacylase that has at least about 50%, at least about 60%, at least about 70%, at least about 75%, at least about 80%, at least about 85%, at least about 90%, at least about 95%, at least about 98%, or more, amino acid sequence identity to the amino acid sequence of E. coli malonyl-CoA:ACP transacylase as depicted in FIG. 4B, (SEQ ID NO:2) and set forth in GenBank Accession No. AAN79832.1.

In some embodiments, a host cell is genetically modifying a host cell with a nucleic acid comprising a nucleotide sequence encoding a fatty acid biosynthetic pathway enzyme, where the nucleic acid is in an expression vector. In some embodiments, the nucleic acid with which a parent host cell is genetically modified, such that HMG-CoA accumulation-induced toxicity and/or cell growth inhibition is reduced, is an expression vector that includes a nucleic acid comprising a nucleotide sequence that encodes one or more fatty acid biosynthetic pathway enzymes that provide for relief of HMG-CoA accumulation-induced toxicity and/or cell growth inhibition. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as E. coli and yeast). Thus, for example, a nucleic acid encoding a mevalonate pathway gene product(s) is included in any one of a variety of expression vectors for expressing the mevalonate pathway gene product(s). Such vectors include chromosomal, nonchromosomal and synthetic DNA sequences.

Numerous suitable expression vectors are known to those of skill in the art, and many are commercially available. The following vectors are provided by way of example; for bacterial host cells: pQE vectors (Qiagen), pBluescript plasmids, pNH vectors, lambda-ZAP vectors (Stratagene); pTrc99a, pKK223-3, pDR540, and pRIT2T (Pharmacia); for eukaryotic host cells: pXT1, pSG5 (Stratagene), pSVK3, pBPV, pMSG, and pSVLSV40 (Pharmacia). However, any other plasmid or other vector may be used so long as it is compatible with the host cell.

For generating a parent host cell comprising one or more heterologous nucleic acids comprising nucleotide sequences encoding a fatty acid biosynthetic pathway enzyme, a fatty acid biosynthetic pathway enzyme enzyme-encoding nucleotide sequence is inserted into an expression vector. The fatty acid biosynthetic pathway enzyme-encoding nucleotide sequence in the expression vector is operably linked to an appropriate expression control sequence(s) (e.g., a promoter) to direct synthesis of the encoded gene product. The fatty acid biosynthetic pathway enzyme coding sequences are operably linked to appropriate expression control sequence(s) to direct synthesis of the encoded gene product. Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544).

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol., 1991: 173(1): 86-93; Alpuche-Aranda et al., PNAS, 1992; 89(21): 10079-83), a nirB promoter (Harborne et al. (1992) Mol. Micro. 6:2805-2813), and the like (see, e.g., Dunstan et al. (1999) Infect. Immun. 67:5133-5141; McKelvie et al. (2004) Vaccine 22:3243-3255; and Chatfield et al. (1992) Biotechnol. 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) Infect. Immun. 70:1087-1096); an rpsM promoter (see, e.g., Valdivia and Falkow (1996). Mol. Microbiol. 22:367-378); a tet promoter (see, e.g., Hillen, W. and Wissmann, A. (1989) In Saenger, W. and Heinemann, U. (eds), Topics in Molecular and Structural Biology, Protein-Nucleic Acid Interaction. Macmillan, London, UK, Vol. 10, pp. 143-162); an SP6 promoter (see, e.g., Melton et al. (1984) Nucl. Acids Res., 12:7035-7056); and the like.

Non-limiting examples of suitable eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

In addition, the expression vectors will in many embodiments contain one or more selectable marker genes to provide a phenotypic trait for selection of transformed host cells such as dihydrofolate reductase or neomycin resistance for eukaryotic cell culture, or such as tetracycline or ampicillin resistance in prokaryotic host cells such as E. coli.

Generally, recombinant expression vectors will include origins of replication and selectable markers permitting transformation of the host cell, e.g., the ampicillin resistance gene of E. coli, the S. cerevisiae TRP1 gene, etc.; and a promoter derived from a highly-expressed gene to direct transcription of the coding sequence. Such promoters can be derived from operons encoding glycolytic enzymes such as 3-phosphoglycerate kinase (PGK), α-factor, acid phosphatase, or heat shock proteins, among others.

In some embodiments, a genetically modified host cell will comprise a fatty acid biosynthetic pathway enzyme-encoding nucleotide sequence operably linked to an inducible promoter. Inducible promoters are well known in the art. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (see, e.g., Guzman et al. (1995) J. Bacteriol. 177:4121-4130); a xylose-inducible promoter, e.g., Pxyl (see, e.g., Kim et al. (1996) Gene 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda $P_L$ promoter, a promoter controlled by a heat-sensitive repressor (e.g., CI857- repressed lambda-based expression vectors; see, e.g., Hoffmann et al. (1999) *FEMS Microbiol Lett.* 177(2):327-34); and the like.

In some embodiments, a fatty acid biosynthetic pathway enzyme coding sequence is operably linked to a constitutive promoter. Suitable constitutive promoters for use in prokaryotic cells are known in the art and include, but are not limited to, a sigma70 promoter, e.g., a consensus sigma70 promoter.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome.

Prenyl Transferases

In some embodiments, a subject genetically modified host cell is genetically modified to include one or more nucleic acids comprising a nucleotide sequence(s) encoding one or more mevalonate pathway enzymes, as described above; and a nucleic acid comprising a nucleotide sequence that encodes a prenyl transferase.

Prenyltransferases constitute a broad group of enzymes catalyzing the consecutive condensation of IPP resulting in the formation of prenyl diphosphates of various chain lengths. Suitable prenyltransferases include enzymes that catalyze the condensation of IPP with allylic primer substrates to form isoprenoid compounds with from about 2 isoprene units to about 6000 isoprene units or more, e.g., 2 isoprene units (Geranyl Pyrophosphate synthase), 3 isoprene units (Farnesyl pyrophosphate synthase), 4 isoprene units (geranylgeranyl pyrophosphate synthase), 5 isoprene units, 6 isoprene units (hexadecylpyrophosphate synthase), 7 isoprene units, 8 isoprene units (phytoene synthase, octaprenyl pyrophosphate synthase), 9 isoprene units (nonaprenyl pyrophosphate synthase, 10 isoprene units (decaprenyl pyrophosphate synthase), from about 10 isoprene units to about 15 isoprene units, from about 15 isoprene units to about 20 isoprene units, from about 20 isoprene units to about 25 isoprene units, from about 25 isoprene units to about 30 isoprene units, from about 30 isoprene units to about 40 isoprene units, from about 40 isoprene units to about 50 isoprene units, from about 50 isoprene units to about 100 isoprene units, from about 100 isoprene units to about 250 isoprene units, from about 250 isoprene units to about 500 isoprene units, from about 500 isoprene units to about 1000 isoprene units, from about 1000 isoprene units to about 2000 isoprene units, from about 2000 isoprene units to about 3000 isoprene units, from about 3000 isoprene units to about 4000 isoprene units, from about 4000 isoprene units to about 5000 isoprene units, or from about 5000 isoprene units to about 6000 isoprene units or more.

Suitable prenyltransferases include, but are not limited to, an E-isoprenyl diphosphate synthase, including, but not limited to, geranyl diphosphate (GPP) synthase, farnesyl diphosphate (FPP) synthase, geranylgeranyl diphosphate (GGPP) synthase, hexaprenyl diphosphate (HexPP) synthase, heptaprenyl diphosphate (HepPP) synthase, octaprenyl (OPP) diphosphate synthase, solanesyl diphosphate (SPP) synthase, decaprenyl diphosphate (DPP) synthase, chicle synthase, and gutta-percha synthase; and a Z-isoprenyl diphosphate synthase, including, but not limited to, nonaprenyl diphosphate (NPP) synthase, undecaprenyl diphosphate (UPP) synthase, dehydrodolichyl diphosphate synthase, eicosaprenyl diphosphate synthase, natural rubber synthase, and other Z-isoprenyl diphosphate synthases.

The nucleotide sequences of a numerous prenyl transferases from a variety of species are known, and can be used or modified for use in generating a subject genetically modified host cell. Nucleotide sequences encoding prenyl transferases are known in the art. See, e.g., Human farnesyl pyrophosphate synthetase mRNA (GenBank Accession No. J05262; *Homo sapiens*); farnesyl diphosphate synthetase (FPP) gene (GenBank Accession No. J05091; *Saccharomyces cerevisiae*); isopentenyl diphosphate:dimethylallyl diphosphate isomerase gene (J05090; *Saccharomyces cerevisiae*), Wang and Ohnuma (2000) *Biochim. Biophys. Acta* 1529:33-48; U.S. Pat. No. 6,645,747; *Arabidopsis thaliana* farnesyl pyrophosphate synthetase 2 (FPS2)/FPP synthetase 2/farnesyl diphosphate synthase 2 (At4g17190) mRNA (GenBank Accession No. NM_202836); *Ginkgo biloba* geranylgeranyl diphosphate synthase (ggpps) mRNA (GenBank Accession No. AY371321); *Arabidopsis thaliana* geranylgeranyl pyrophosphate synthase (GGPS1)/GGPP synthetase/farnesyltranstransferase (At4g36810) mRNA (GenBank Accession No. NM_119845); *Synechococcus elongatus* gene for farnesyl, geranylgeranyl, geranylfarnesyl, hexaprenyl, heptaprenyl diphosphate synthase (SelF-HepPS) (GenBank Accession No. AB016095); etc.

Codon Usage

In some embodiments, the nucleotide sequence encoding a mevalonate pathway enzyme is modified such that the nucleotide sequence reflects the codon preference for the particular host cell. In some embodiments, the nucleotide sequence encoding a fatty acid biosynthetic pathway enzyme is modified such that the nucleotide sequence reflects the codon preference for the particular host cell. For example, the nucleotide sequence will in some embodiments be modified for yeast codon preference. See, e.g., Bennetzen and Hall (1982) *J. Biol. Chem.* 257(6): 3026-3031. As another non-limiting example, the nucleotide sequence will in other embodiments be modified for *E. coli* codon preference. See, e.g., Gouy and Gautier (1982) *Nucleic Acids Res.* 10(22):7055-7074; Eyre-Walker (1996) *Mol. Biol. Evol.* 13(6); 864-872. See also Nakamura et al. (2000) *Nucleic Acids Res.* 28(1):292.

Codon usage tables for many organisms are available that summarize the percentage of time a specific organism uses a specific codon to encode for an amino acid. Certain codons are used more often than other, "rare" codons. The use of "rare" codons in a sequence generally decreases its rate of translation. Thus, e.g., the coding sequence is modified by introducing one or more rare codons, which affect the rate of translation, but not the amino acid sequence of the enzyme translated. For example, there are 6 codons that encode for arginine: CGT, CGC, CGA, CGG, AGA, and AGG. In *E. coli* the codons CGT and CGC are used far more often (encoding approximately 40% of the arginines in *E. coli* each) than the codon AGG (encoding approximately 2% of the arginines in *E. coli*). Modifying a CGT codon within the sequence of a gene to an AGG codon would not change the sequence of the enzyme, but would likely decrease the gene's rate of translation.

Additional Genetic Modifications

In some embodiments, a subject genetically modified host cell is one that is genetically modified to include one or more nucleic acids comprising a nucleotide sequence(s) that encode a fatty acid biosynthetic pathway enzyme; and that is further genetically modified to achieve enhanced production of a terpene biosynthetic pathway intermediate, and/or that is further genetically modified to enhance production of an isoprenoid or isoprenoid precursor, and/or that is further genetically modified such that an endogenous terpene biosynthetic pathway gene is functionally disabled. The term "functionally disabled," as used herein, refers to a genetic modification of a nucleic acid, which modification results in production of a gene product encoded by the nucleic acid that is produced at below normal levels, and/or is non-functional. Such genetic modification(s) may decrease the specific IPP or mevalonate productivity of a strain (production per cell) as compared to a parent strain, but the relief in HMG-CoA induced toxicity would increase the cell density such that the total productivity of the culture (specific productivity multiplied by the cell density of the culture) would increase.

Genetic modifications that enhance production of an endogenous terpene biosynthetic pathway intermediate include, but are not limited to, genetic modifications that result in a reduced level and/or activity of a phosphotransacetylase in the host cell. The intracellular concentration of an isoprenoid biosynthetic pathway intermediate is enhanced by increasing the intracellular concentration of acetyl-CoA. *E. coli* secretes a significant fraction of intracellular acetyl-CoA in the form of acetate into the medium. Deleting the gene encoding phosphotransacetylase, pta, the first enzyme responsible for transforming acetyl-CoA into acetate, reduces acetate secretion. Genetic modifications that reduce the level and/or activity of phosphotransacetylase in a prokaryotic host cell are particularly useful where the parent host cell is one that is genetically modified with a nucleic acid comprising nucleotide sequences encoding one or more MEV pathway gene products.

Since acetyl-CoA is a reactant used by both acetoacetyl-CoA thiolase and HMGS in the synthesis of HMG-CoA, and in some host cells, increases in the intracellular pool of acetyl-CoA could lead to increases in the intracellular pool of HMG-CoA, which in turn could lead to a toxicity effect. Therefore, genetic modifications that reduce the total activity of phosphotransacetylase could lead to a reduction in growth rate or final cell density due to the accumulation of HMG-CoA, generating a parent strain that could be modified using the method of the invention. Alternatively, genetic modifications that increase the total activity of phosphotransacetylase could be used to overcome a toxicity effect caused by the accumulation of HMG-CoA.

In some embodiments, a genetic modification that results in a reduced level of phosphotransacetylase in a prokaryotic host cell is a genetic mutation that functionally disables the prokaryotic host cell's endogenous pta gene encoding the phosphotransacetylase. The pta gene can be functionally disabled in any of a variety of ways, including insertion of a mobile genetic element (e.g., a transposon, etc.); deletion of all or part of the gene, such that the gene product is not made, or is truncated and is non-functional in converting acetyl-CoA to acetate; mutation of the gene such that the gene product is not made, or is truncated and is non-functional in converting acetyl-CoA to acetate; deletion or mutation of one or more control elements that control expression of the pta gene such that the gene product is not made; and the like.

In some embodiments, the endogenous pta gene of a genetically modified host cell is deleted. Any method for deleting a gene can be used. One non-limiting example of a method for deleting a pta gene is by use of the λRed recombination system. Datsenko and Wanner (2000) *Proc Natl Acad Sci U S A* 97(12): p. 6640-5. The pta gene will in some embodiments be deleted from a host cell (e.g., *E. coli*) that is genetically modified with a nucleic acid comprising nucleotide sequences encoding MK, PMK, MPD, and IDI. The pta gene will in some embodiments be deleted from a host cell (e.g., *E. coli*) that is genetically modified with a nucleic acid comprising nucleotide sequences encoding MK, PMK, MPD, and IPP. The pta gene will in some embodiments be deleted from a host cell (e.g., *E. coli*) that is genetically modified with a nucleic acid comprising nucleotide sequences encoding MK, PMK, MPD, IPP, and a prenyl transferase.

Other modifications that would increase the levels of intracellular acetyl-CoA include, but are not limited to, modifications that would decrease the total activity of lactate dehydrogenase within the cell, modifications that would decrease the total activity of acetate kinase within the cell, modifications that would decrease the total activity of alcohol dehydrogenase within the cell, modifications that would interrupt the tricarboxylic acid cycle, such as those that would decrease the total activity of 2-ketoglutarate dehydrogenase, or modifications that would interrupt oxidative phosphorylation, such as those that would decrease the total activity of the (F1F0)H+-ATP synthase, or combinations thereof.

Other modifications that would decrease the levels of intracellular acetyl-CoA include, but are not limited to, modifications that would increase the total activity of lactate dehydrogenase within the cell, modifications that would increase the total activity of acetate kinase within the cell, and modifications that would increase the total activity of alcohol dehydrogenase within the cell, or combinations thereof.

In some embodiments, a parent host cell is one that is genetically modified, as described above to increase levels of HMG-CoA; and is further genetically modified such that an endogenous DXP biosynthetic pathway gene is functionally disabled.

In other embodiments, a subject genetically modified host cell is one that is genetically modified to include one or more nucleic acids comprising a nucleotide sequence(s) that encode DXP biosynthetic pathway gene product(s); and that is further genetically modified such that an endogenous MEV biosynthetic pathway gene is functionally disabled.

In some embodiments, where subject genetically modified host cell is a prokaryotic host cell that has been genetically modified with nucleic acid(s) comprising nucleotide sequences encoding one or more MEV pathway gene products, the host cell will be further genetically modified such that one or more endogenous DXP pathway genes is functionally disabled. DXP pathway genes that can be functionally disabled include one or more of the genes encoding any of the following DXP gene products: 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, and 1-hydroxy-2-methyl-2-(E)-butenyl 4-diphosphate synthase.

An endogenous DXP pathway gene can be functionally disabled in any of a variety of ways, including insertion of a mobile genetic element (e.g., a transposon, etc.); deletion of all or part of the gene, such that the gene product is not made, or is truncated and is enzymatically inactive; mutation of the gene such that the gene product is not made, or is truncated and is enzymatically non-functional; deletion or mutation of one or more control elements that control expression of the gene such that the gene product is not made; and the like.

Compositions Comprising a Subject Genetically Modified Host Cell

The present invention further provides compositions comprising a subject genetically modified host cell. A subject composition comprises a subject genetically modified host cell; and will in some embodiments comprise one or more further components, which components are selected based in part on the intended use of the genetically modified host cell. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell; and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Enhancing Isoprenoid Production by Modulating Fatty Acid Levels

TABLE 1

Strains and plasmids used in this study.

| Strain/Plasmid | Genotype/Description |
|---|---|
| DH10B | F-, mcrA, Δ(mrr-hsdRMS-mcrBC), F80lacZΔM15, ΔlacX74, recA1, endA1, araD139, Δ (ara, leu)7697, galU, galK, λ-, rpsL (StrR), nupG |
| DP10 | DH10B, Δ(araFGH) φ(ΔaraEp $P_{cp8}$-araE) |
| TOP10 | F-, mcrA, Δ(mrr-hsdRMS-mcrBC), F80lacZΔM15, ΔlacX74, recA1, endA1, araD139, Δ (ara, leu)7697, galU, galK, λ-, rpsL (StrR), nupG |
| pADS | pTrc99A containing synthetic ADS; $Ap^r$ |
| pAtoB | pBad33 containing atoB under control of $P_{BAD}$ promoter; $Cm^r$ |
| pBad18 | Cloning vector containing $Ap^r$, modified pBR322 origin with truncation of rop gene, araC, and $P_{BAD}$ promoter |
| pBad18HMGR | pBad18 containing tHMGR under control of $P_{BAD}$ promoter; $Ap^r$ |
| pBad24 | Cloning vector containing $Ap^r$, modified pBR322 origin with truncation of rop gene, araC, and $P_{BAD}$ promoter |
| pBad24MevT | pBad24 containing atoB, HMGS, tHMGR under control of $P_{BAD}$ promoter; $Ap^r$ |
| pBad33 | Cloning vector containing $Cm^r$, pACYC184 origin, araC, and $P_{BAD}$ promoter |
| pBad33MevT | pBad33 containing atoB, HMGS, tHMGR under control of $P_{BAD}$ promoter; $Cm^r$ |

TABLE 1-continued

Strains and plasmids used in this study.

| Strain/Plasmid | Genotype/Description |
|---|---|
| pCP20 | Temperature sensitive vector carrying flippase (FLP) recombinase |
| pHMGR | pBad33 containing tHMGR under control of $P_{BAD}$ promoter; $Cm^r$ |
| pHMGS | pBad33 containing HMGS under control of $P_{BAD}$ promoter; $Cm^r$ |
| pHMGS(C159A) | pHMGS derivative containing HMGS(C159A), under control of $P_{BAD}$ promoter; $Cm^r$ |
| pHMGSR | pBad33 containing HMGS and tHMGR under control of $P_{BAD}$ promoter; $Cm^r$ |
| pKD13 | Gene deletion vector containing FRT - $Km^R$ - FRT fragment, R6K origin, $Ap^R$ |
| pKD46 | Temperature sensitive vector carrying the λ Red recombinase |
| pKD85 | Integration vector containing FRT - $Km^R$ - FRT fragment linked to $P_{CP8}$-araE', R6K origin, $Ap^R$ |
| pLac33 | pBad33 derivative containing $Cm^r$, pACYC184 origin, $P_{LAC}$ |
| pMBIS | pBBR1MCS-3 containing MK, PMK, MPD, idi, ispA under $P_{LAC}$; $Tc^R$ |
| pMevT | pBad33 derivative containing the atoB, HMGS and tHMGR genes under control of $P_{LAC}$; $Cm^r$ |
| pMevT(C159A) | pBad33MevT derivative containing HMGS(C159A) |
| pTrc99A | Expression vector containing, $Ap^R$, pBR322 origin, $lacI^Q$, and $P_{TRC}$ promoter |

Material and Methods
General

Media components and chemicals were purchased from Sigma-Aldrich (St. Louis, Mo.) and Fisher Scientific (Pittsburgh, Pa.). For cloning and propagation of E. coli strains harboring the various recombinant pathways, Luria broth with Miller's modification (Sigma) was used with appropriate antibiotics for plasmid selection and 0.06% glucose for the repression of $P_{BAD}$ and $P_{LAC}$ promoter systems. DL-mevalonate used for media supplementation was prepared by mixing 1 volume of 2 M DL-mevalonic acid lactone (Sigma-Aldrich) with 1.02 volumes of 2 M KOH and incubating at 37° C. for 30 min. Campos et al. (2001) Biochem J 353, 59-67. Fatty acids for media supplementation were purchased from Sigma and employed in defined media at a concentration of 100 μg/ml in the presence of 400 μg/ml Brij (Sigma). Enzymes for molecular biology were purchased from New England Biolabs (Beverly, Mass.) and Invitrogen. E. coli strains TOP 10 and DH10B, both from Invitrogen, were used for cloning and plasmid construction.

Operon and Plasmid Construction

Construction of plasmids pMevT, pMBIS, pADS, pBad33MevT and pLac33 is described in, e.g., U.S. Pat. No. 7,183,089; U.S. Pat. No. 7,172,886; U.S. Pat. No. 7,192,751; U.S. Patent Publication Nos. 2006/007946, 2003/0148479, and 2004/0005678; and Martin et al. (2003) Nat. Biotech. 21:796-802. Construction of plasmids pBAD24MevT, pBAD33MevT, pMevT, pMBIS, pADS, pAtoB, pHMGS, pHMGR, pBAD18HMGR, pHMGSR, pMevT(C159A) [also referred to as pBAD33MevT(C159A)], and pHMGS (C159A) is described in, e.g., U.S. Pat. No. 7,183,089; U.S. Provisional Patent Application No. 60/802,266; Pitera et al. (2007) Metab Eng 9(2): 193-207, and in the following example. Nucleotide sequences of the plasmids are provided in U.S. Provisional Patent Application No. 60/802,266 and in U.S. Pat. No. 7,183,089: pBAD24MevT (SEQ ID NO:1); pBAD33MevT (SEQ ID NO:2); pMevT (SEQ ID NO:3); pMBIS (SEQ ID NO:4); pADS (SEQ ID NO:5); pAtoB (SEQ ID NO:6); pHMGS (SEQ ID NO:7); pHMGR (SEQ ID NO:8; pBAD18HMGR (SEQ ID NO:9); pHMGSR (SEQ ID NO: 10); pMevT(C159A), also referred to as pBAD33MevT (C159A) (SEQ ID NO:11); pHMGS(C159A) (SEQ ID NO:12); and tHMGR (SEQ ID NO: 13). See also, U.S. Pat. No. 7,183,089; U.S. Pat. No. 7,172,886; U.S. Patent Publication Nos. 2006/007946, 2003/0148479, and 2004/0005678; Martin et al. (2003) Nat. Biotech. 21:796-802; and Pitera et al. (2007) Metab Eng 9(2): 193-207.

As expression of biochemical pathways is often optimal at a specific expression level, the MevT operon was cloned in a variety of expression vectors to determine the effect of plasmid copy number and promoter strength on expression of the cloned pathway. The MevT operon was cloned into the SalI site of pBAD24 (Guzman et al. (1995) J. Bacteriology 177: 4121-4130), M. Ehrmann et al., (1997) Proc. Natl. Acad. Sci. USA 94: 13111-13115), medium copy number, arabinose inducible plasmid, by digesting both the empty vector and the MevT operon in pCR4 TOPO with SalI restriction enzyme and ligating with T4 DNA ligase. The resulting plasmid was named pBAD24MevT (SEQ ID NO:1, U.S. Pat. No. 7,183, 089).

The MevT operon was also cloned into the XmaI-PstI sites of pBAD33 (Guzman et al. (1995) J. Bacteriology 177:4121-4130); Hiszczynska-Sawicka. (1997) Plasmid 38: 174-179), low copy, arabinose inducible plasmid, by digesting both the empty vector and the MevT operon in pCR4 TOPO with XmaI and PstI restriction enzymes and ligating with T4 DNA ligase. The resulting plasmid, was named pBAD33MevT (SEQ ID NO:2, U.S. Pat. No. 7,183,089), see Martin et al. (2003) supra.

To place the MevT operon under the control of a modified $P_{LAC}$ promoter (weaker promoter), the araC-$P_{BAD}$ NsiI-XmaI fragment of pBAD33MevT was replaced with the NsiI-XmaI fragment of pBBR1MCS (Kovach et al. (1995) Gene 166: 175-176) containing the modified $P_{LAC}$ promoter. Digestion of both pBAD33MevT and pBBR1MCS was conducted using NsiI and XmaI restriction enzymes and ligated using T4 DNA ligase. The resulting plasmid was named pMevT (SEQ ID NO:3, U.S. Pat. No. 7,183,089), see US Patent Application publication number 20040005678 and Martin et al. (2003) supra.

To generate the empty plasmid control for pMevT, the MevT operon was excised from pMevT using SalI restriction enzyme. The resulting plasmid containing only the $P_{LAC}$ promoter was called pLac33 (Martin et al. (2003) supra).

Figure 5A:
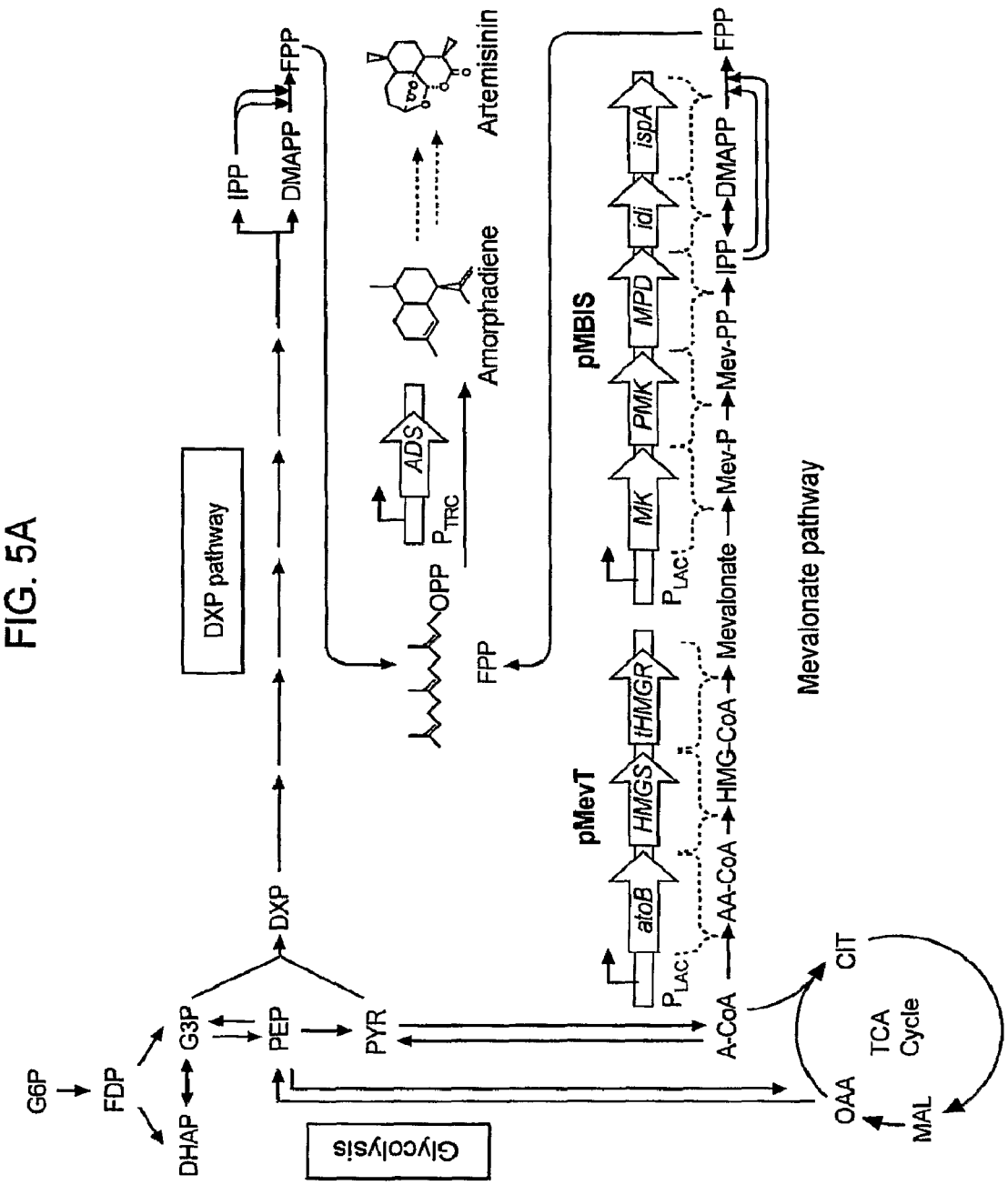
FIG. 5A provides a schematic depiction of a mevalonate pathway, a DXP pathway, and the tricarboxylic acid (TCA) cycle.

To produce FPP, IPP, and DMAPP from mevalonate, the operon called MBIS was constructed as described in U.S. Pat. No. 7,172,886; U.S. Pat. No. 7,192,751; US Patent Application publication numbers 20030148479, 20040005678; and Martin et al. (2003) supra. MBIS contains the genes MK, PMK and MPD from S. cerevisiea and idi, and ispA from E. coli (FIG. 5A). As described, the MBIS operon was assembled in the plasmid pBBR1MCS-3 (Kovach et al. (1995) supra) under the control of a modified $P_{LAC}$ promoter. The IPTG inducible plasmid was named pMBIS (SEQ ID NO 4, U.S. Pat. No. 7,183,089).

To produce amorpha-4,11-diene from FPP, a synthetic amorphadine synthase gene was created as described in U.S. Pat. No. 7,192,751, US Patent Application publication number 20040005678 and Martin et al. (2003) supra. The synthetic gene was cloned into the vector pTrc99A (Amann et al. (1988) Gene 69:301-315), as described, and the IPTG inducible plasmid was named pADS (SEQ ID NO:5, U.S. Pat. No. 7,183,089).

In order to determine the source of toxicity caused by the increased expression of the MevT operon, the individual genes of the MevT operon and combinations thereof were amplified and cloned into expression vectors.

AtoB was amplified from pBAD24MevT using standard PCR protocols and primers complementary to the 5' and 3' ends of the gene. AtoB was cloned into the XmaI-SalI sites of pBAD33, low copy, arabinose inducible plasmid, by digesting both the empty vector and PCR product with XmaI and SalI restriction enzymes and ligating with T4 DNA ligase. The resulting plasmid was named pAtoB (SEQ ID NO 6, U.S. Pat. No. 7,183,089).

HMGS was amplified from pBAD24MevT using standard PCR protocols and primers complementary to the 5' and 3' ends of the gene. HMGS was cloned into the XmaI-SalI sites of pBAD33, low copy, arabinose inducible plasmid, by digesting both the empty vector and PCR product with XmaI and SalI restriction enzymes and ligating with T4 DNA ligase. The resulting plasmid was named pHMGS (SEQ ID NO 7, U.S. Pat. No. 7,183,089).

The truncated HMGR was amplified from pBAD24MevT using standard polymerase chain reaction (PCR) protocols and primers complementary to the 5' and 3' ends of the gene. The truncated HMGR (tHMGR) was cloned into the XmaI-SalI sites of pBAD33, low copy, arabinose inducible plasmid, and pBAD18 (Guzman et al. (1995) J. Bacteriology 177: 4121-4130), medium copy, arabinose inducible plasmid, by digesting both the empty vectors and PCR product with XmaI and SalI restriction enzymes and ligating with T4 DNA ligase. The resulting low copy number plasmid was named pHMGR (SEQ D: NO:8, U.S. Pat. No. 7,183,089), and the resulting medium copy number plasmid was named pBAD18HMGR (SEQ ID NO:9, U.S. Pat. No. 7,183,089).

An operon containing only HMGS and the truncated HMGR was created by amplifying the two gene segment from pBAD24MevT using standard PCR protocols and primers complementary to the 5' end of HMGS and the 3' end of HMGR. The HMGS and HMGR fragment was cloned into the SalI site of pBAD33, low copy, arabinose inducible plasmid, by digesting both the empty vector and PCR product with SalI restriction enzyme and ligating with T4 DNA ligase. The resulting plasmid was named pHMGSR (SEQ ID NO: 10, U.S. Pat. No. 7,183,089).

Strain Construction

Construction of E. coli DP10 is described in U.S. Provisional Patent Application No. 60/802,266, Pitera et al. (2007) Metab Eng 9(2): 193-207, and as follows.

In E. coli DH10B, the $P_{BAD}$ promoter system suffers from all or none induction, in which sub-saturating concentrations of arabinose give rise to subpopulations of cells that are fully induced and uninduced. To alleviate this problem, a DH10B host with regulatable control of $P_{BAD}$ in a homogeneous population of cells was constructed. The chromosomal araE gene, encoding the low-affinity, high-capacity arabinose transport protein, was placed under constitutive control and combined with a deletion of the genes encoding the secondary arabinose transporter, araFGH, following the method of Khlebnikov et al. (2000) J Bacteriol 182:7029-7034.

To disrupt the secondary arabinose transporter in DH10B, the araFGH operon was deleted using λ Red recombinase system described by Datsenko and Wanner (Proc Natl Acad Sci USA 97, 6640-6645 (2000)). The PCR product for gene inactivation was amplified from pKD13 using primers araFGH-for and araFGH-rev, purified and transformed into DH10B expressing the three λ Red genes (γ, β, and exo) from the helper plasmid, pKD46. The resulting mutants were selected for and propagated in medium containing 25 μg/mL Kanamycin until the resistance marker was excised using FLP recombinase from pCP20. Deletion of the operon was confirmed by PCR.

The constitutive promoter, $P_{CPS}$, and the 5' portion of araE were amplified from pKD85 using primers pKDaraE-for and pKDaraE-rev, purified and transformed into DH10B ΔaraFGH harboring the λ Red helper plasmid. After selection with 25 µg/mL Kanamycin, the resistance marker was excised as above and the promoter insertion was confirmed by PCR and DNA sequencing of PCR product that amplified the insertion region. The resulting strain, which had a linear response in gene expression as a function of the arabinose concentration across the population, was named DP10.

Site-Directed Mutagenesis of HMGS

Construction of plasmids encoding a full length, catalytically inactive *S. cerevisiae* HMGS is described in U.S. Pat. No. 7,183,089, U.S. Provisional Patent Application No. 60/802,266, Pitera et al. (2007) *Metab Eng* 9(2): 193-207, and as follows.

To determine if the toxicity caused by the high expression of HMGS alone in *E. coli* is due to the high level production of a heterologous protein or to enzyme activity, a full length, catalytically inactive HMGS was created. Following the work of Rokosz et al. (*Arch Biochem Biophys* 312, 1-13 (1994)), the catalytic cysteine of the *S. cerevisiae* HMGS active site in pBAD33MevT was replaced with an alanine by site-directed mutagenesis (QuickChange Site-directed mutagenesis kit, Stratagene). The cysteine at amino acid position 159 to alanine mutant of the yeast HMGS, named HMGS(C159A), was verified by DNA sequence of the entire operon. The plasmid pBad33MevT containing the HMGS(C159A) mutant was named pMevT(C159A), also referred to as pBad33MevT (C159A), (SEQ ID NO:11, U.S. Pat. No. 7,183,089).

In order to construct a plasmid that expressed mutant HMG-CoA synthase alone, HMGS(C159A) was amplified from pMevT(C159A) using primers HMGS-XF and HMGS-SR cloned into the XmaI-SalI sites of pBAD33. The resulting plasmid was named pHMGS(C159A) (SEQ ID NO 12, U.S. Pat. No. 7,183,089).

Amorpha-4,11-diene Production Assays

Amorpha-4,11-diene production from *E. coli* strains expressing the full heterologous mevalonate pathway and amorphadiene synthase with or with mevalonate supplementation was assayed. *E. coli* DH10B containing plasmids pMevT, pMBIS, and pADS (FIGS. 5A and 5B) were grown in C medium containing 3.4% glycerol, 1% Casamino acids (BD, Franklin Lakes, N.J.), micronutrients, 50 µg/ml carbenicillin, 5 µg/ml tetracycline, and 25 µg/ml chloramphenicol with varying concentrations of exogenous mevalonate. The amorphadiene-producing cells were inoculated from overnight cultures into C medium to an optical density ($OD_{600}$) of 0.05, incubated at 37° C. with continuous shaking and induced at an $OD_{600}$ of approximately 0.25 with the simultaneous addition of 0.5 mM Isopropyl β-D-1-thiogalactopyranoside (IPTG) and varying concentrations of mevalonate. Prior to inoculation, an overlay of 20% (v/v) dodecane (Sigma) was added to each culture flask to trap the volatile sesquiterpene product. The amorphadiene concentration in the organic layer was assayed at multiple time points by diluting 10 µL of the dodecane overlay into 990 µL of ethyl acetate spiked with 5 µg/mL trans-caryophyllene (both Sigma) as an internal standard.

Dodecane/ethyl acetate extracts were analyzed on a Hewlett-Packard 6890 gas chromatograph-mass spectrometer (GC/MS). A 1 µL sample was separated on the GC using a DB-5 column (Agilent Technologies, Inc., Palo Alto, Calif.) and helium carrier gas at 1 L/min. The oven cycle for each sample was 80° C. for two minutes, increasing temperature at 30° C./min to a temperature of 160° C., increasing temperature at 3° C./min to 170° C., increasing temperature at 50° C./min to 300° C., and a hold at 300° C. for two minutes. The resolved samples were analyzed by a Hewlett-Packard model 5973 mass selective detector that monitored ions 189 and 204 m/z. Previous mass spectra and NMR demonstrated that the amorpha-4,11-diene synthase product was amorphadiene and verified the retention time. Since pure standards of amorpha-4,11-diene are not currently available, the concentrations were quantified in terms of caryophyllene equivalents. A standard curve for caryophyllene was determined, based on a pure standard. The amorpha-4,11-diene concentration is based on the relative abundance of 189 and 204 m/z ions to the abundance of the total ions in the mass spectra of the two compounds.

Figure 5B:
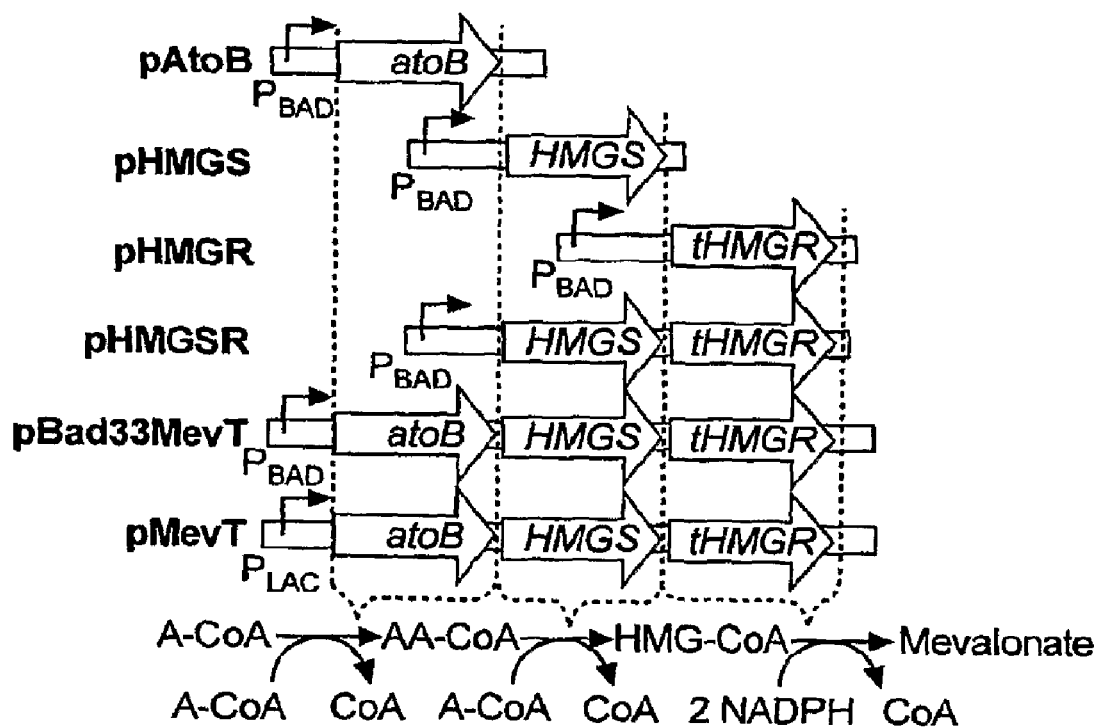
FIG. 5B schematically depicts various mevalonate pathway operons and constructs.

FIGS. 5A and 5B. (A) Heterologous mevalonate pathway and native DXP (non-mevalonate) pathway for the production of amorphadiene. (B) Mevalonate producing operons and gene constructs. The abbreviations of the gene and pathway intermediates are as follows: atoB, acetoacetyl-CoA thiolase; HMGS, HMG-CoA synthase; tHMGR, truncated HMG-CoA reductase; MK, mevalonate kinase; PMK, phosphomevalonate kinase; MPD, mevalonate pyrophosphate decarboxylase; idi, IPP isomerase from *E. coli*; ispA, FPP synthase; ADS, amorphadiene synthase; G6P, glucose-6-phosphate; FDP, fructose-1,6-bisphosphate; G3P, glyceraldehydes-3-phosphate; DHAP, dihydroxyacetone-phosphate; PEP, phosphoenolpyruvate; CIT, citrate; MAL, malate; OAA, oxaloacetate DXP, 1-deoxy-D-xylulose-5-phosphate; IPP, isopentenyl pyrophosphate; DMAPP, dimethylallyl pyrophosphate; FPP, farnesyl pyrophosphate; A-CoA, acetyl-CoA; AA-CoA acetoacetyl-CoA; HMG-CoA, hydroxymethylglutaryl-CoA; Mev-P, mevalonate-5-phosphate; Mev-PP, mevalonate pyrophosphate.

Growth and Metabolite Analysis of Engineered Cells

The growth, production and metabolite levels of *E. coli* DP10 expressing genes encoding the early steps of the mevalonate pathway and combinations thereof were assayed. To accurately characterize the cell physiology and metabolite levels of the engineered strains, studies were preformed using fully defined C medium unless otherwise specified. C medium was supplemented with 3.4% glycerol, all individual amino acids as per Neidhardt et al (*J Bacteriol* 119, 736-747 (1974)), 4.5 µg/ml thiamine-HCl, micronutrients and appropriate antibiotics. In one or two plasmid systems chloramphenicol and carbenicillin were each used at 50 µg/ml. Starter cultures of DP10 harboring various genetic constructs were inoculated from single colonies and incubated overnight at 37° C. in defined C medium supplemented with 0.06% glucose (to repress the $P_{BAD}$ and $P_{LAC}$ promoters) and antibiotics. Overnight starter cultures were diluted to an $OD_{600}$ of 0.05 in fresh medium, incubated at 37° C. with continuous shaking and induced with the addition of 1.33 mM (0.02%) arabinose or 0.5 mM IPTG at an $OD_{600}$ of approximately 0.25. When assaying only cell growth, cultures were grown in 96-well microtiter plates. During experiments involving metabolite analysis, the engineered strains were incubated in 1-L baffled shake flasks. Samples were taken at multiple times points during the course of the experiment to assay for $OD_{600}$, mevalonate production, and intracellular metabolites. Experiments were repeated in duplicate to confirm trends in growth and metabolite concentrations.

The optical density of samples taken from cultures in baffled flasks was measured using a UV-Spectrophotometer (Beckman), while the $OD_{600}$ of cultures in 96-well microtiter plates was measured using a microtiter plate reader (SpectraMax, Molecular Devices).

GC-MS Quantification of Mevalonate

Mevalonate (mevalonic acid) concentration in cultures of engineered E. coli was determined by GC-MS analysis. 560 µL of E. coli culture was mixed with 140 µL of 500 mM HCl in a glass GC vial to convert mevalonate from mevalonic acid to mevalonic acid lactone. 700 µL of ethyl acetate, spiked with 500 µg/ml (−)-trans-caryophyllene as an internal standard, was added to each vial and then the samples were shaken at maximum speed on a Fisher Vortex Genie 2 mixer (Fisher Scientific) for 3-5 minutes. The ethyl acetate extract of the acidified culture was diluted 1:100 with fresh ethyl acetate in a clean GC vial before analysis.

Diluted ethyl acetate extracts were analyzed using an Agilent Technologies GC-MS (6890 gas chromatograph and 5973 mass selective detector) operating in electron impact mode. The GC column used was an Agilent Technologies Cyclosyl-B Chiral column (30 m×250 µm×0.25 µm). Helium was used as the carrier gas at a constant flow of 1 mL/min and 1 µL splitless injections were performed. The injection port was maintained at 250° C., the MS source temperature was maintained at 230° C., and the MS quad temperature was held constant at 150° C. The column temperature profile was 90° C. for 1 min; 30° C./min to 250° C.; and held at 250° C. for 2 min. The selected ions monitored were m/z 71 and 58 for mevalonic acid lactone, and m/z 189 and 204 for (−)-trans-caryophyllene. Retention time, mass spectrum and concentration of extracted mevalonic acid lactone were confirmed using commercial DL-mevalonic acid lactone (Sigma).

Intracellular Metabolite Extraction and Analysis

The concentrations of intracellular acyl-CoAs and adenylate pool were determined by LC-MS analysis of trichloroacetic acid (TCA) culture extracts taken during the exponential phase of growth as described in U.S. Pat. No. 7,183,089, U.S. Provisional Patent Application No. 60/802,266, and Pitera et al. (2007) Metab Eng 9(2): 193-207. To simultaneously and rapidly quench cellular metabolism, isolate E. coli cells from growth medium and extract metabolites, cells were centrifuged through a layer of silicone oil into a denser solution of TCA by method similar to that of M. Shimazu et al. (Anal Biochem 328, 51-59 (2004)). Using 15-ml Falcon tubes (Fischer Scientific), 2 ml of silicone oil (AR200 from Fluka) was layered over 0.5 ml of 10% trichloroacetic acid (Fluka) in Deuterium Oxide (Sigma). The TCA layer was spiked with 5 µM crotonyl-CoA as an internal standard. Tubes were stored on ice until time of sampling. To each tube, 10 mL of cell culture was carefully added above the silicone oil layer. Tubes were then quickly centrifuged at 4° C. for 3 min at 10,000×g. By centrifugation, the cells traverse the silicone layer, lyse in the TCA layer and quench metabolism. The spent medium was carefully removed by aspiration and the TCA extract layer was transferred to a 2 mL centrifuge tube using a small gauge needle and syringe. To neutralize the TCA, 1 mL of ice cold 0.5 M Tri-n-octylamine in 1,1,2-Trichloro-1,2,2-trifluoroethane (both Sigma) was added, tubes were vortexed for 1 minute and then centrifuged at max speed for 2 minutes to separate the layers. The aqueous layer was removed for analysis by LC-MS.

The neutralized TCA extract was analyzed using a Hewlett-Packard 1100 series LC-MS using electrospray ionization. A 50 µL sample was separated on a C-18 reverse phase HPLC column (250×2.1 mm Inertsil 3 um ODS-3 by Varian) using a two solvent gradient system adapted from Dallugue et al (2002) Anal Bioanal Chem 374, 835-840. Solvent A was 100 mM ammonium acetate buffer at pH 6 and Solvent B was 70% Solvent A and 30% acetonitrile. The HPLC column was equilibrated each run with 8% Solvent B (92% Solvent A) for 12 min. Using a 0.25 mL/min flow rate and linear gradients as indicated, the elution program was the following: 8% Solvent B at 0 min to 50% Solvent B at 5 min, gradient increase to 100% Solvent B at 13 min, isocratic at 100% Solvent B until 19 min, gradient returning to 8% Solvent B at 26 min. The resolved metabolite samples were analyzed by an electrospray ionization mass selective detector (ESI-MS) operated in positive mode. The following ESI-MS parameters were used: drying gas, 12 L/min; nebulizer pressure, 60 psig; drying gas temperature, 300° C.; capillary voltage, 2500 V. Selected ions corresponding to the protonated molecular ion of each metabolite were monitored: adenosine 5'-triphosphate (ATP)—m/z 508, adenosine 5'-diphosphate (ADP)—m/z 428, adenosine 5'-monophosphate (AMP)—m/z 348, coenzyme A—m/z 768, acetyl-CoA—m/z 810, propionyl-CoA—m/z 824, crotonyl-CoA—m/z 836, acetoacetyl-CoA—m/z 852, malonyl-CoA—m/z 854, succinyl-CoA—m/z 868, methylmalonyl-CoA—m/z 868, 3-hydroxy-3-methyl-glutaryl-CoA (HMG-4G-CoA)—m/z 912. Retention times, mass spectra, and concentrations of extracted metabolites were confirmed using commercial standards (Sigma).

Adenylate energy charge of each strain was calculated from the adenylate pool measurement as defined by Atkinson (1968) Biochemistry 7, 4030-4034:

$$\text{Energy Charge} = \frac{[ATP] + \frac{1}{2}[ADP]}{[ATP] + [ADP] + [AMP]}$$

HMG-CoA Reductase Assays

Active tHMGR protein levels in E. coli DP10 lysates expressing different MevT constructs were assayed enzymatically by monitoring the disappearance of NADPH at 340 nm, as described in U.S. Provisional Patent Application No. 60/802,266, and Pitera et al. (2007) Metab Eng 9(2): 193-207. Samples of cell culture were taken at various time points after induction, centrifuged at 10,000×g for 8 minutes to pellet the cells, and the supernatant was removed. Cell pellets were frozen on dry ice until analysis. Cells were lysed using Bug Buster reagent (Novagen) supplemented with 40 µg/mL lysozyme, protease inhibitor, and benzonase, following manufacture's protocol. Total protein concentrations of the lysates were determined by using the Bradford assay employing bovine serum albumin as a standard.

HMG-CoA reductase assays were preformed in 100 µL reactions in microtiter plates at 30° C. Reaction mixtures consisted of 50 mM Tris-HCl pH 7.5, 0.2 mM NADPH, and 0.3 mM HMG-CoA. Reactions were started with the addition of diluted cell lysate. Enzymatic activity was determined by monitoring the disappearance of NADPH by measuring the absorbance at 340 nm. Background rate of NADPH consumption was determined by reaction without HMG-CoA. Enzyme activity was calculated from the difference in rate of consumption between test sample (with HMG-CoA) and negative control (without HMG-CoA).

Analysis of Cellular Fatty Acid Composition

The fatty acid composition of engineered cells was determined by fatty acid methyl ester (FAME) analysis of lyophilized cell pellets. Aliquots of cell culture sampled at various time points were centrifuged at 10,000×g for 8 min to pellet the bacteria cells. The volume of culture sampled was calculated to yield a cell pellet of at least 20 mg wet weight. The spent media was carefully decanted and the cell pellets were snap frozen in liquid nitrogen. The frozen pellets were then lyophilized for 24 hours at −80° C. under vacuum using a freeze drier. FAME analysis of lyophilized cell pellets was preformed by Microbial ID (Newark, Del.).

Transcript Analysis Sample Preparation

Biomass designated for transcript analysis was snap-frozen in liquid nitrogen immediately and stored at −80° C. until analysis. RNA was extracted from the cell samples using the RNEasy Midi kit (QIAGEN). Using 40 µg aliquots of extracted RNA from each sample point, pre-labeled cDNA was synthesized using random-primed reverse transcription reactions in a 40-µl volume containing 12.5 µg primers (Invitrogen, Carlsbad, Calif.), 1×RT buffer (Invitrogen, Carlsbad, Calif.), 0.01 mM DTT (Invitrogen, Carlsbad, Calif.), 1 unit/µl Superase-In (Ambion, Austin, Tex.), 0.5 mM dATP/dCTP/dGTP (Invitrogen, Carlsbad, Calif.), 0.1 mM dTTP (Invitrogen, Carlsbad, Calif.), 0.4 mM amino-allyl-dUTP (Ambion, Austin, Tex.) and 10 units/µl Superscript II (Invitrogen, Carlsbad, Calif.) following the enzyme manufacturer's instructions. The cDNA was base hydrolyzed in 100 mM NaOH/10 mM EDTA at 65° C. for ten minutes and then neutralized in 7.0 pH HEPES at a final concentration of 500 mM. The Tris remaining in the cDNA suspension was removed by three buffer exchange spins using Micron YM-30 columns (Millipore) and eluted in a final volume of 15 µl water. The cDNA was then labeled using either Alexa 555 or Alexa 647 (Invitrogen, Carlsbad, Calif.) following the manufacturers protocol.

Microarray Hybridization

Glass microarrays printed with full-length dsDNA prepared by PCR or 70-mer oligonucleotides (Operon) designed to probe every open reading frame (ORF) of *E. coli* MG1655 were hybridized in a TECAN hybridization station with ~6-10 µg of labeled cDNA per channel of detection. The hybridization program included a pre-hybridization (5×SSC/0.2% SDS/1% BSA, 42° C., 60 minutes), a 15-hour hybridization (Ambion Hyb Solution #3, 40° C., medium agitation), two low stringency washes (1×SSC/0.2% SDS, 42° C., 2 minutes each), two high stringency washes (0.1×SSC/0.2% SDS, 25° C., 2 minutes each), and two final washes (0.1×SSC, 25° C., 2 minutes each). Following hybridization the slides were scanned with an Axon 4500.

Transcriptional Profile Data Analysis

The raw scans were globally normalized using Genepix software and then exported to SNOMAD (Colantuoni et al. *Bioinformatics*, 18(11): p. 1540-1541. (2002)) for loess normalization to correct for any hybridization artifacts. The local Z-score generated by SNOMAD as well as the serial analysis for microarray (SAM) (Tusher et al. *Proc Natl Acad Sci USA*. 98(9), 5116-5121 (2001)) software were used as guides to determine biologically significant gene expression changes among the replicate hybridization data sets. This list of significant genes was then mined using hierarchal clustering (Cluster 3.0) (Eisen et al., *Proc Natl Acad Sci USA*. 95(25), 14863-14868. (1998)) to determine a base set of clusters in each data set. Once a base set of clusters was chosen, k-means clustering was also used to search the data set for temporal patterns in gene expression (Cluster 3.0).

Results

Initial Steps of Heterologous Pathway Limits Carbon Flux to Amorphadiene

To begin improving terpenoid production from engineered *E. coli*, limiting steps in the engineered pathway to amorphadiene were determined, as described in U.S. Pat. No. 7,183,089, U.S. Provisional Patent Application No. 60/802,266, Pitera et al. *Metab Eng* 9(2): 193-207 (2007), and as follows. In two-phase cultures, *E. coli* DH10B expressing the full pathway to amorphadiene (harboring plasmids pMevT, pMBIS, and pADS—FIG. 5A) was grown in C media, containing Casamino acids (as described above), supplemented with increasing concentrations of exogenesis mevalonate. An organic overlay of dodecane was employed to trap the volatile amorphadiene and allow accurate quantification. GC-MS analysis of the dodecane overlays from these cultures revealed that the addition of exogenous mevalonate to the system increased the production of amorphadiene over time, above that produced with no supplementation of the cultures. Co-expression of both operons and ADS allows the production of amorphadiene from *E. coli*'s supply of acetyl-CoA. The supplementary mevalonate feeds into the mevalonate pathway prior to the pMBIS enzymes and is converted to additional amorphadiene, as tested up to the addition of 20 mM D,L-mevalonate. This increase in production demonstrates that the in vivo supply of the mevalonate intermediate is limiting carbon flux to the isoprenoid end products.

Multiple studies on poly(3-hydroxybutyrate) (PHB) production by recombinant *E. coli* demonstrate the bacterium's ability to supply high levels of acetyl-CoA, which is also used for the synthesis of PHB. Using an operon composed of polyhydroxyalkanoate biosynthesis genes from *Alcaligenes latus*, Choi et al. (*Appl Environ Microbiol* 64, 4897-4903 (1998)) were able to produce 194.1 g/L of PHB at a rate of 4.63 g/L/hr from *E. coli's* pool of acetyl-CoA. Based on these findings, it does not appear that the supply of acetyl-CoA to the heterologous mevalonate pathway should limit mevalonate production in the present system. Rather, the ability of the first three genes of the mevalonate pathway (*E. coli's* atoB encoding acetoacetyl-CoA thiolase, *S. cerevisiae's* HMGS encoding HMG-CoA synthase and tHMGR encoding a truncated HMG-CoA reductase) to rapidly convert acetyl-CoA to mevalonate appears to be limiting. Together, these findings demonstrate that the in vivo production of mevalonate by the MevT operon limits the production of the sesquiterpene amorphadiene.

Increased Expression of the MevT Operon Inhibits Cell Growth

To increase the in vivo production of mevalonate by the first three genes of the mevalonate pathway, the expression of the MevT operon was increased by changing promoters and increasing plasmid copy number (see operon and plasmid construction above). The low copy pMevT expresses the MevT operon from the native Lac promoter of *E. coli*, a non-consensus $P_{LAC}$. To increase promoter strength, the MevT operon was cloned into the low copy plasmid pBad33 (Guzman et al. *J Bacteriol* 177, 4121-4130. (1995)) under the control of the arabinose inducible promoter $P_{BAD}$, to create pBad33MevT. pMevT and pBad33MevT both have the pACYC origin of replication and share an identical plasmid sequence except for the promoter region. To further increase expression, the MevT operon was cloned into the medium-high copy plasmid pBad24 (Guzman et al. (1995) supra), also under arabinose control to create pBad24MevT.

Increasing the expression of the MevT operon, by increasing promoter strength and plasmid copy number, resulted in the inhibition of cell growth, as described in U.S. Pat. No. 7,183,089, and Pitera et al. *Metab Eng* 9(2): 193-207 (2007). *E. coli* DP10 (DH10B engineered for linear arabinose response in a homogeneous population) harboring each of the individual plasmids or their empty vector controls, was grown in fully defined C medium (see above) and cell growth was monitored before and after induction. As the growth profile showed (Pitera et al. *Metab Eng* 9(2): 193-207 (2007)), induction of MevT from the non-consensus $P_{LAC}$, contained in pMevT, caused no substantial change in cell growth in comparison to the empty plasmid controls. However, the increased expression of the MevT operon from the araC-$P_{BAD}$ promoter system of pBAD33MevT caused growth inhibition. Retaining the araC-$P_{BAD}$ promoter system but increasing the plasmid copy number, thereby further increasing the total expression of MevT, as occurs in pBAD24MevT, resulted in more severe growth inhibition. The growth inhibition may be due to toxicity from the high expression of heterologous protein, called metabolic burden or load, or may be caused by an alteration in cell metabolism. As these data demonstrate, increasing the expression of the MevT operon increased toxicity to the engineered strains.

HMGS Activity is Toxic While Co-Expression of tHMGR Relieves Growth Inhibition

To determine the cause of growth inhibition associated with increased expression of the MevT operon, the operon was broken down into its individual gene components and combination thereof as described in U.S. Pat. No. 7,183,089, and Pitera et al. *Metab Eng* 9(2): 193-207 (2007). The plasmids pAtoB, pHMGS, and pHMGR, each expressing one of the individual genes, and pBAD33 (empty vector control) were transformed into *E. coli* DP10, and the resulting cells were incubated in a 96-well microtiter plate reader, in fully defined C medium (as described above). Cell growth was monitored continuously after inducing with 0.02% arabinose. In comparison to the empty vector control (DP10 containing pBAD33), the expression of atoB and HMGR in *E. coli* (in strains harboring plasmids pAtoB and pHMGR, respectively) had no significant effect on cell growth. However, the expression of HMGS alone (in strain harboring pHMGS) caused severe growth inhibition. Under conditions that repress expression of HMGS from $P_{BAD}$) (addition of 0.06% glucose to the media) plasmid pHMGS had little effect on growth.

The growth inhibition caused by expression of *S. cerevisiae* HMGS alone in *E. coli* may be due to the general burden caused by the high level production of a heterologous protein, to a metabolic load placed upon the cell by expressing a primary sequence containing rare amino acids, or the toxicity may be due to the metabolic activity of HMGS. To differentiate between the possibilities, a fall length but catalytically inactive HMGS was created as described in U.S. Pat. No. 7,183,089, and Pitera et al. *Metab Eng* 9(2): 193-207 (2007). The active site of the wild-type *S. cerevisiae* HMGS was determined by comparing the protein sequence of the yeast HMG-CoA synthase to the active site sequences of several mammalian synthases (Rokosz et al. *Arch Biochem Biophys* 312, 1-13 (1994) The active site residues of *S. cerevisiae* HMGS were identical to the active site amino acid residues of the mammalian HMG-CoA synthases. Following the method of Rokosz et al ((1994), supra), the catalytic cysteine of the *S. cerevisiae* HMGS active site was replaced with an alanine, creating a full length HMG-CoA synthase protein that was catalytically inactive. The plasmid containing this inactive synthase alone was named pHMGS(C159A).

The metabolic activity of HMGS in *E. coli* may cause growth inhibition by the accumulation of the enzyme product, 3-hydroxy-3-methylglutaryl-CoA (HMG-CoA), or by the depletion of *E. coli's* supply of acetoacetyl-CoA. To determine if either phenomenon was feasible, tHMGR was co-expressed with HMGS from the same plasmid, pHMGSR (see above).

Figure 5C:
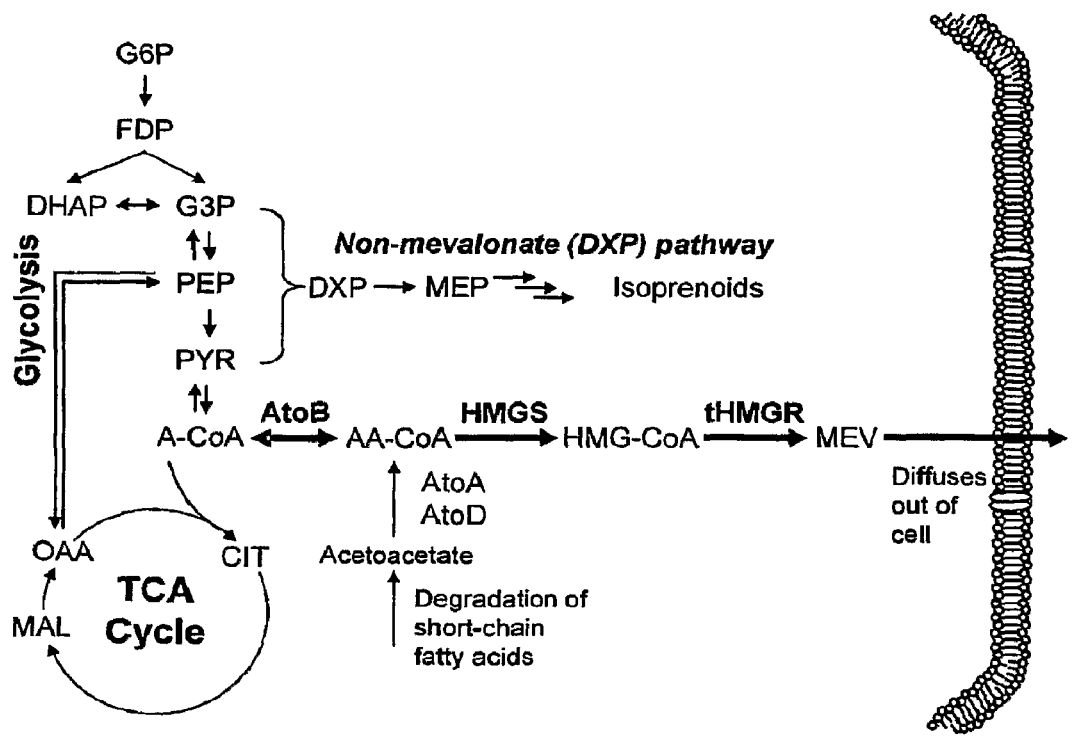
FIG. 5C is a schematic depiction of mevalonate production in engineered *E. coli*.

The growth of *E. coli* DP10 expressing the modified HMGS constructs was monitored as above. In comparison to the empty vector control (DP10 containing pBad33), the growth of cells expressing HMGS alone was inhibited. However, strains harboring pHMGS(C159A) grew only slightly slower than the control cells, indicating that high heterologous protein expression alone was not the cause of toxicity. When co-expressing both HMGS and HMGR (as in strain harboring pHMGSR), cell growth was almost restored to that of the empty vector control. By co-expressing tHMGR and HMGS, *E. coli's* native supply of acetoacetyl-CoA was still being consumed, implying that the toxicity caused by HMGS expression is due to the accumulation of HMG-CoA and not the depletion of acetoacetyl-CoA. However, by expressing both genes, the HMG-CoA that is produced by HMGS is converted into mevalonate which then crosses the cell membrane to the medium with no observable growth inhibition (FIG. 5C). High extra-cellular concentrations of mevalonate had no significant effect on the growth of *E. coli*.

FIG. 5C. Mevalonate is produced from acetyl-coA (A-CoA), derived from glycolysis, by the action of *E. coli* acetoacetyl-CoA thiolase (AtoB), yeast HMG-CoA synthase (HMGS) and truncated yeast HMG-CoA reductase (tHMGR). Acetoacetyl-CoA (AA-CoA) is naturally present in *E. coli* from the native expression of atoB and by the activity of remaining genes of the Ato operon in the presence of short chain fatty acids. Glucose-6-phosphate, G6P; fructose-1,6-bisphosphate, FDP; dihydroxy-acetone-phosphate, DHAP; glyceraldehydes-3-phosphate, G3P; phosphoenolpyruvate, PEP; pyruvate, PYR; citrate, CIT, malate, MAL; oxaloacetate, OAA; 3-hydroxy-3-methylglutaryl-CoA, HMG-CoA; mevalonate, MEV; 1-deoxy-D-xylulose-5-phosphate, DXP; 2-C-methyl-D-erythritol-4-phosphate, MEP.

Malonyl Co-A Accumulates in *E. coli* Cells Inhibited by High Levels of HMG-CoA

U.S. Pat. No. 7,183,089, and Pitera et al. (2007) *Metab Eng* 9(2): 193-207, demonstrate that the cause of growth inhibition in strains expressing the MevT operon and HMGS alone is the accumulation of the mevalonate pathway intermediate, HMG-CoA. The following studies demonstrate that *E. coli* strains that are inhibited by high levels of HMG-CoA accumulate the fatty acid precursor Malonyl-CoA. Malonyl-CoA accumulation is the classic indicator of inhibition of fatty acid biosynthesis in *E. coli*.

The metabolite profiles of the engineered *E. coli* strains expressing the various mevalonate pathway constructs, described above, were obtained. Cell growth and mevalonate concentrations were assayed from cultures of *E. coli* DP10 containing the various MevT gene constructs and control plasmids. Intracellular acyl-CoAs and adenylates were extracted from engineered strains at multiple time points beginning immediately prior to induction. As a direct control for strains harboring pBad33MevT, an inactive pathway variant containing the HMGS(C159A) mutation, named pMevT (C159A), was employed. Cells were cultured in defined C media, induced with arabinose, and sampled as described above (see Growth and Metabolite Analysis of Engineered Cells)

As described in U.S. Pat. No. 7,183,089, growth of *E. coli* expressing HMGS alone was almost completely inhibited, while co-expression of HMGS and if tHMGR alleviated the observed toxicity (FIG. 6G). With the addition of atoB and completion of the MevT operon, as in pBad33MevT, cell growth was again slowed in comparison to controls. Cells harboring either of the two inactive operons, pHMGS (C159A) and pMevT(C159A), grew only slightly slower than the empty vector control, likely due to the metabolic requirements of heterologous protein production.

As described in U.S. Pat. No. 7,183,089, the varying levels of acyl-CoAs between strains indicated that the reason for the observed growth inhibition was the accumulation of HMG-CoA (FIGS. 6A-F). Expressing HMGS alone in *E. coli*, as in pHMGS, significantly reduced levels of coenzyme-A (FIG. 6A) and acetyl-CoA (FIG. 6B) in comparison to control strains, while leading to the accumulation of HMG-CoA (FIG. 6D)—even prior to induction. In contrast, by co-expressing HMGS and tHMGR from the same transcript, as in pHMGSR, the HMG-CoA produced by HMGS was converted to mevalonate (Table 2) leading to no detectable intracellular HMG-CoA, and levels of coenzyme A and acetyl-CoA similar to cells containing the empty vector, pBad33, and inactive pathway controls, pHMGS(C159A) and pMevT (C159A).

TABLE 2

Mevalonate production from *E. coli* DP10 expressing MevT genes

| | Mevalonate concentration at 25 hr |
|---|---|
| pHMGSR | 0.12 mM |
| pBad33MevT | 15.21 mM |
| pMevT(C159A) | Not detected |

Figure 6D:
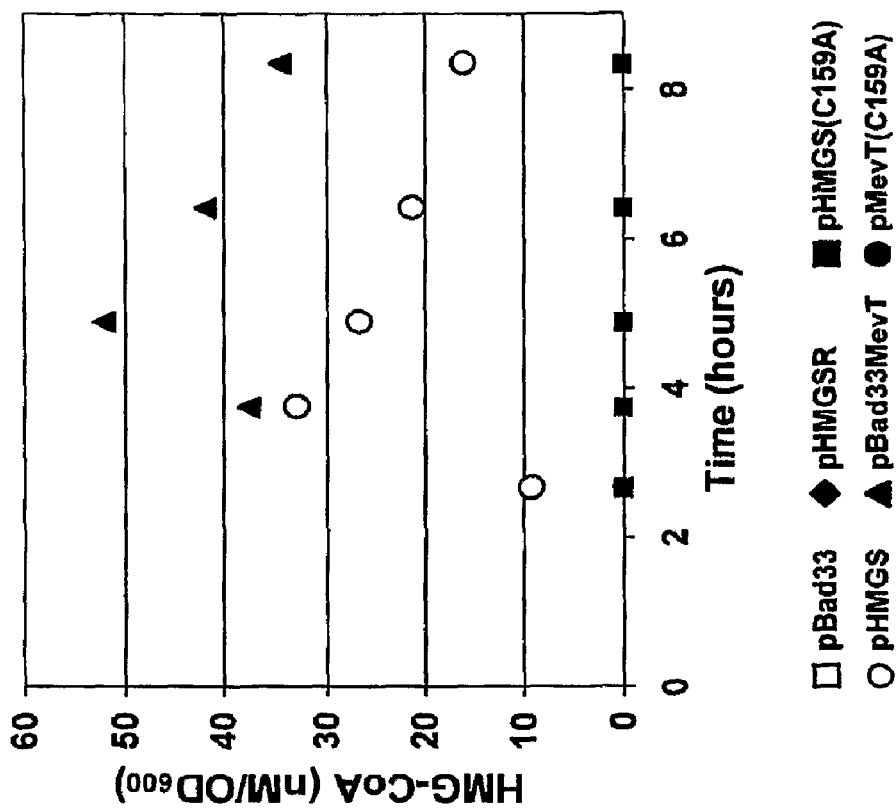
Figure 6C:
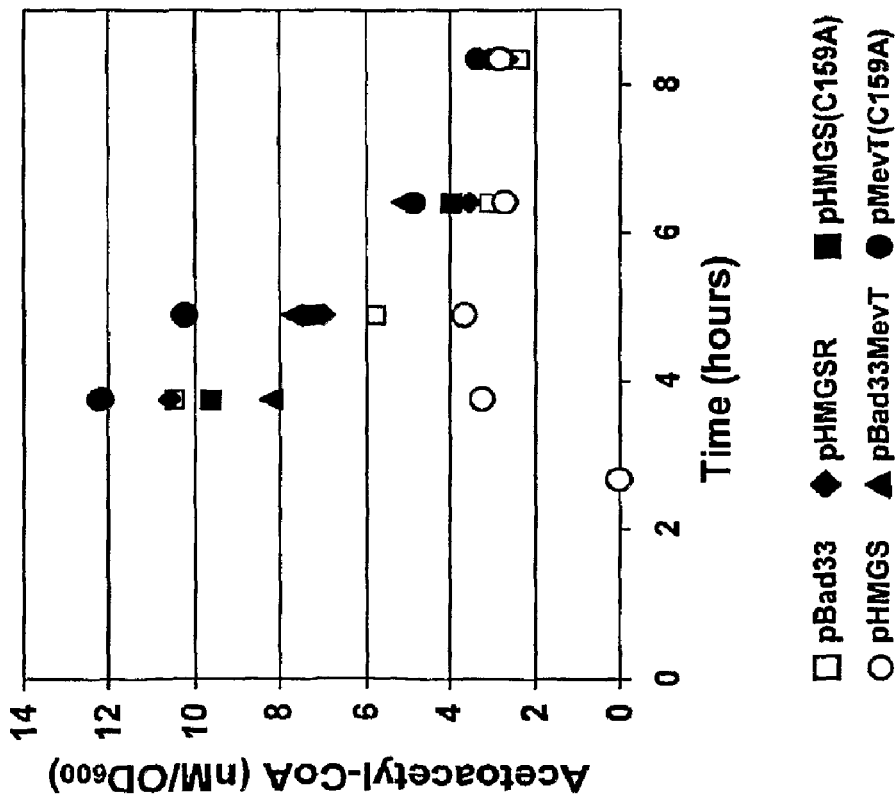
Figure 6G:
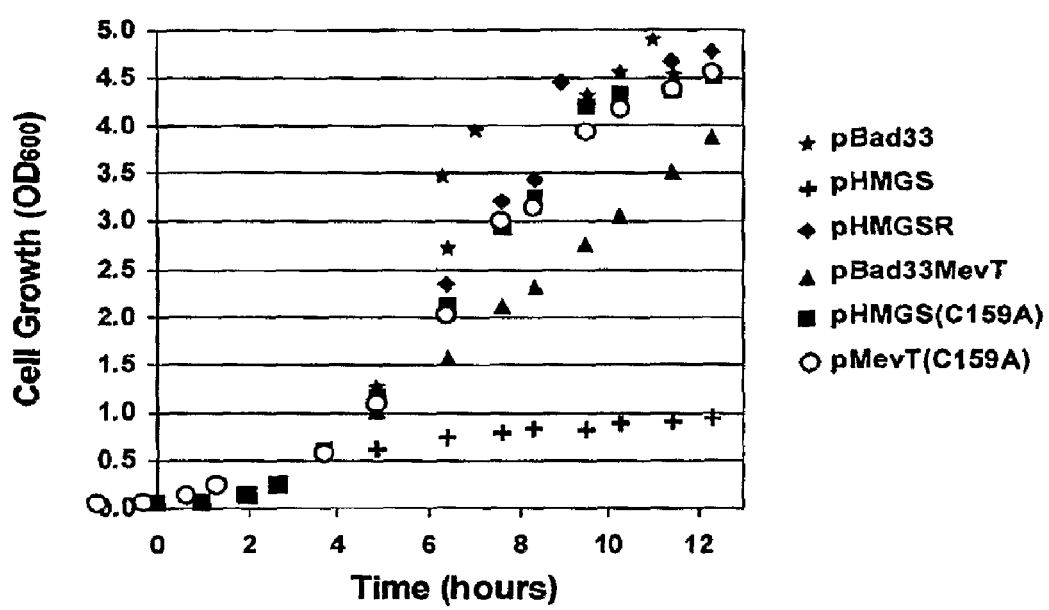

Acetoacetyl-CoA levels were also lower at early time points in cells containing pHMGS; however the intracellular concentration was already low in all strains (FIG. 6C). If growth inhibition was due to decreases in acetoacetyl-CoA, we would expect a similar phenotype in strains co-expressing HMGS and tHMGR.

It is feasible that including tHMGR in an operon with HMGS destabilized the mRNA transcript and reduced the expression of HMGS, leading to the above results. To eliminate this possibility, HMGS and tHMGR were co-expressed on separate plasmids (pHMGS and pBad18HMR) and similar results were obtained.

Expression of all three MevT genes in pBad33MevT provided additional substrate for HMGS and greatly increased carbon flux through the initial mevalonate pathway as shown by the approximately 125-fold increase in mevalonate produced after 25 hours (Table 2). However, with the additional carbon flux through the pathway, HMG-CoA began to accumulate and acetyl-CoA levels decreased at later times.

Furthermore, *E. coli* expressing the inactive MevT operon at high levels (in a strain harboring pMevT(C159A)) had the same growth profile as the control, while high expression of the functional MevT operon (in strain harboring pBAD33MevT) inhibited cell growth. As in the case of pHMGS, this result demonstrates that growth inhibition was caused by expression of all three MevT enzymes and was not due to high production of heterologous proteins.

In addition to HMG-CoA, the fatty acid precursor Malonyl-CoA also accumulated in the growth inhibited *E. coli* strains. The expression of HMGS alone caused a large increase in intracellular concentrations of malonyl-CoA after induction (FIG. 6E). Levels of malonyl-CoA were also elevated in cells harboring pBad33MevT. The high concentrations of malonyl-CoA may account for the low levels of coenzyme A and acetyl-CoA when HMGS is expressed alone.

The remaining acyl-CoAs that were tracked (propionyl-CoA, succinyl-CoA and methylmalonyl-CoA) did not vary significantly between strains.

Changes in the adenylate pool also presented interesting trends. Strains exhibiting growth inhibition had a higher energy charge at later time points than strains that experience no growth inhibition (FIG. 6F).

FIGS. 6A-G. Acyl-CoA levels and adenylate energy charge and growth of cells expressing MevT genes. Acyl-CoAs and adenosines extracted from *E. coli* DP10 containing pBad33 (control), pHMGS, pHMGR, pHMGSR, pBad33MevT, pHMGS(C159A) (inactive HMGS), or pMevT(C159A) (inactive MevT). Coenzyme A (A), acetyl-CoA (B), acetoacetyl-CoA (C), HMG-CoA (D)), malonyl-CoA (E), adenylate energy charge (F), cell growth (G). The first sample for metabolite extraction was taken immediately prior to induction.

Increasing Expression of tHMGR Reduces Toxicity of Increased MevT Expression and Reduces Accumulation of Malonyl-CoA.

To reduce the accumulation of HMG-CoA in cells expressing MevT and thereby alleviate growth inhibition, the expression of the truncated *S. cerevisiae* HMGR was increased, as described in U.S. Pat. No. 7,183,089. Using a two plasmid system in *E. coli* DP10, the MevT operon was co-expressed with an additional copy of tHMGR on a second, medium copy plasmid (pBad33MevT & pBad18HMGR). The growth, mevalonate production, and acyl-CoA levels of cells overexpressing tHMGR were compared to those of cells expressing only the MevT operon (pBad33MevT & pBad18), cells expressing MevT from the non-consensus $P_{LAC}$ (pMevT & pTrc99A), and a control strain expressing the inactive MevT operon (pMevT(C159A) & pBad18). Cells were cultured in defined C media, induced with arabinose or IPTG (for pMevT & pTrc99A), and sampled as described above (see Growth and Metabolite Analysis of Engineered Cells).

Figure 7D:
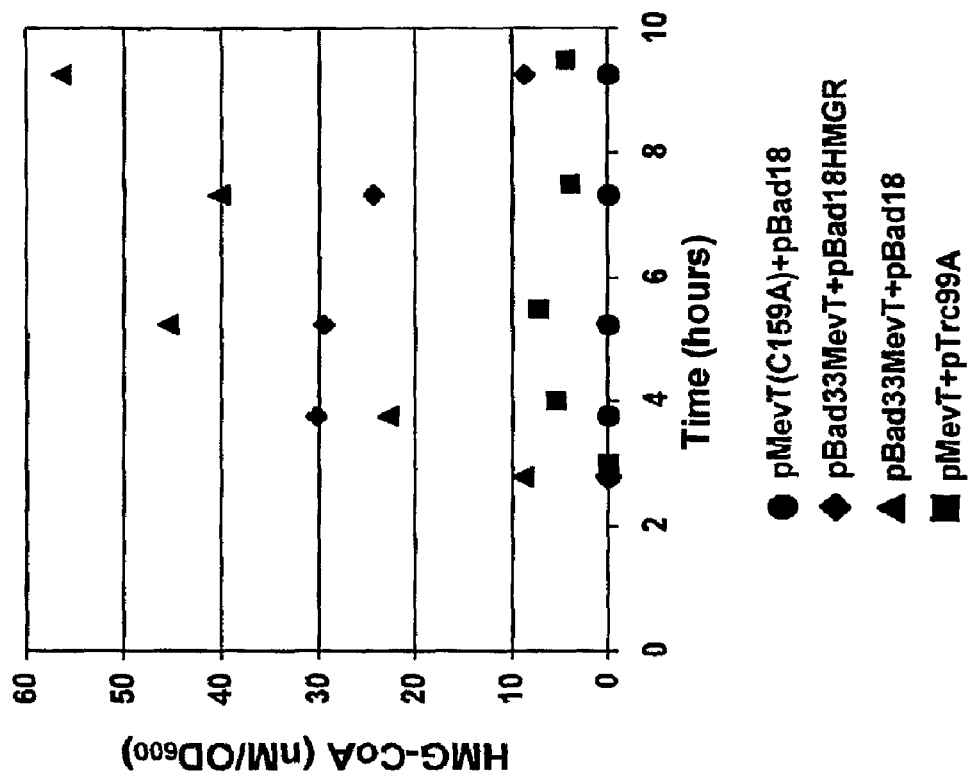
Figure 7C:
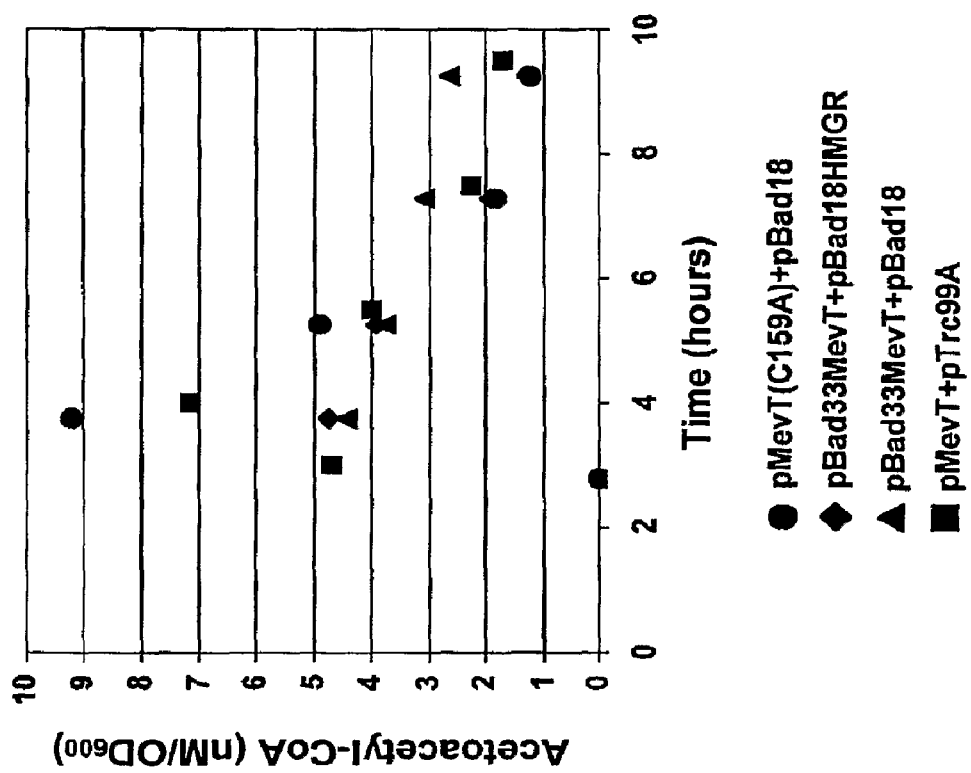
Figure 7F:
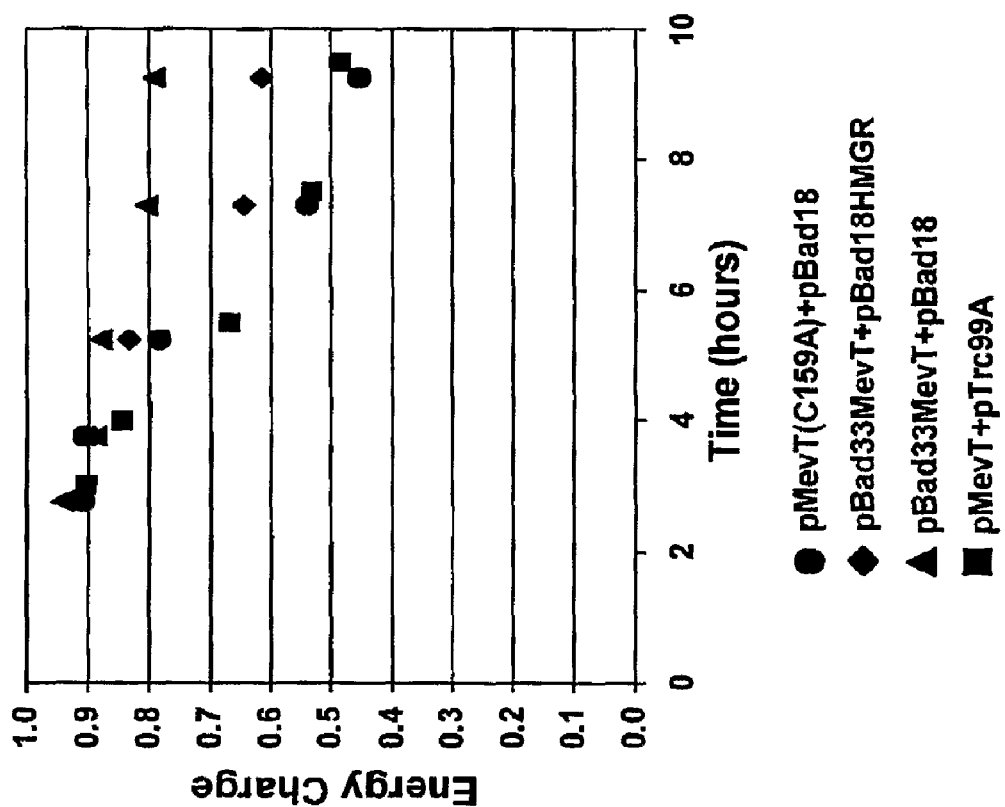
Figure 7E:
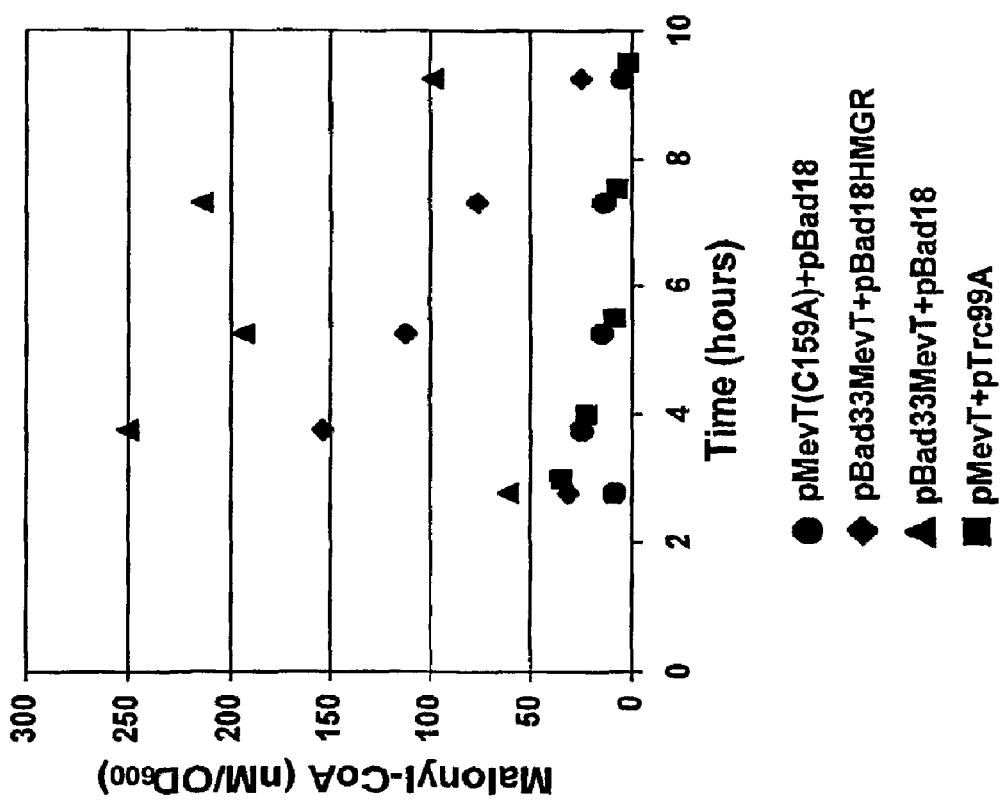
Figure 7H:
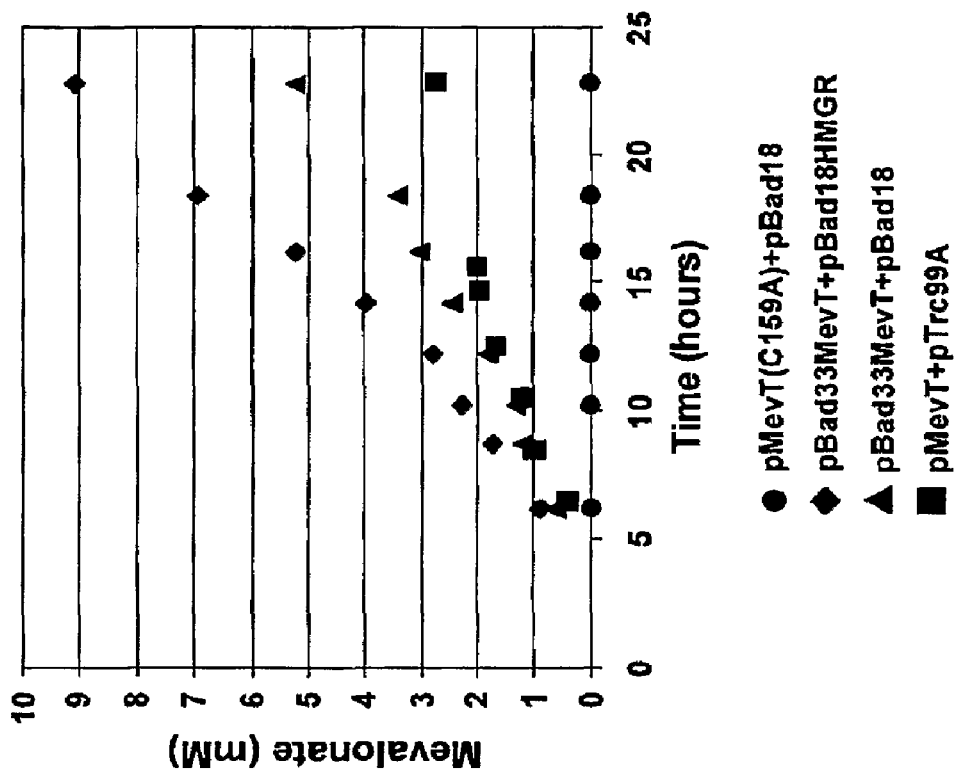
Figure 7G:
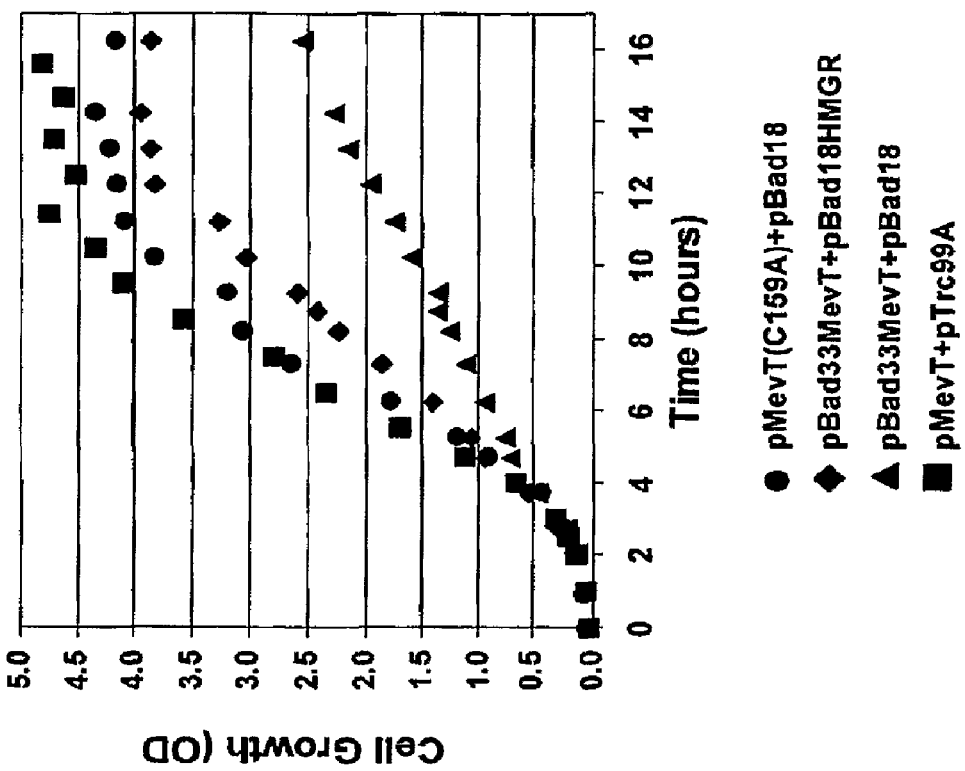

Relative to the inactive control, cells expressing the MevT operon alone from the araC-$P_{BAD}$ system (pBad33MevT & pBad18) again exhibited growth inhibition (FIG. 7G) and accumulated intracellular HMG-CoA (FIG. 7D) and Malonyl-CoA (FIG. 7E). In comparison, overexpressing tHMGR (pBad33MevT & pBad18HMGR) increased the growth rate to almost that of the inactive control, reduced the accumulation of intracellular HMG-CoA, particularly at later times, reduced the accumulation of Malonyl-CoA, and increased mevalonate production (FIG. 7H) by almost two-fold over cells harboring pBad33MevT & pBad18. The free coenzyme-A (FIG. 7A) and acetoacetyl-CoA (FIG. 7C) levels of both strains harboring pBad33MevT were nearly identical, and acetyl-CoA levels were similar (FIG. 7B). All strains with an active MevT operon had lower levels of acetyl-CoA at early time points, presumably from the conversion of *E. coli*'s pool of acetyl-CoA to mevalonate.

Cells expressing MevT from the non-consensus $P_{LAC}$ (pMevT & pTrc99A) grew rapidly after induction with IPTG to an optical density higher than that of the inactive pathway control. The cells accumulated little intracellular HMG-CoA (<10 nM/OD$_{600}$); however, they also produced less mevalonate than either of the strains containing pBad33MevT. This difference may be primarily due to lower expression of the MevT genes from the non-consensus Lac promoter.

To verify that the addition of a second copy of tHMGR increased the levels of HMG-CoA reductase, cell lysates of the above strains were assayed for increased HMG-CoA reductase activity. The increased copy number of tHMGR resulted in a peak increase in cellular HMGR activity of 2.5 fold above strains harboring pBad33MevT alone. As predicted by differences in cell growth, HMG-CoA accumulation, and mevalonate production, expression of MevT from the non-consensus $P_{LAC}$ (pMevT & pTrc99A) resulted in substantially less HMGR activity than when the operon was expressed from araC-$P_{BAD}$. Interestingly, HMGR activity of the strain with the inactive HMGS (pMevT(C159A) & pBad18) was substantially higher than the active MevT operon in pBad33MevT. Although expression of this construct produced active tHMGR, there was no metabolic flux through the pathway and also no perceived growth inhibition. The cytotoxic effect of HMG-CoA accumulation in cells harboring pBad33MevT may result in an overall decrease in active protein as well as inhibition of cell growth (see microarray analysis of HMG-CoA toxicity in E. coli, below).

All four strains contained relatively similar levels of acetoacetyl-CoA that decreased over time, regardless of growth rate, verifying that the depletion of acetoacetyl-CoA is not the cause of growth inhibition. Distinct differences were seen in the levels of coenzyme-A at later times; however, the coenzyme-A pool was lowest in strains that displayed little or no growth inhibition. This difference may be due to rapidly growing strains beginning to transition from early logarithmic growth to late-logarithmic growth or early stationary phase. This hypothesis may also explain why the energy charge was highest at later times in strains that grew the slowest (FIG. 7F).

FIGS. 7A-H. Acyl-CoA levels and adenylate energy charge, growth, and mevalonate production of cells overexpressing tHMGR and MevT operons. E. Coli DP10 harboring two plasmid systems for the production of mevalonate: inactive pathway control (pMevT(C159A)+pBad18), MevT co-expressed with additional tHMGR (pBad33MevT+pBad18HMGR), MevT operon expressed alone (pBad33MevT+pBad18), and MevT expressed from a non-consensus Lac promoter (pMevT+pTrc99A). Coenzyme A (A), acetyl-CoA (B), acetoacetyl-CoA (C), HMG-CoA (D), malonyl-CoA (E), adenylate energy charge (F), cell growth (G), and mevalonate production (H). The first sample for metabolite extraction was taken immediately prior to induction except for pMevT+pTrc99A which was taken 0.5 hr post induction.

From these data, it is clear that growth inhibition in strains highly expressing the MevT operon was caused by the accumulation of intracellular HMG-CoA and not the metabolic burden of heterologous protein expression or the depletion of acyl-CoA precursors. By overexpressing both tHMGR and the MevT operon from araC-$P_{BAD}$ systems, growth inhibition and HMG-CoA accumulation was reduced and mevalonate production increased by approximately three fold over our initial system, pMevT. Implementing a similar strategy in the context of the remaining mevalonate pathway genes and amorphadiene synthase should result in increased production of the sesquiterpene. However, increasing the total activity of tHMGR and alleviating the toxicity caused by the high expression of MevT would increase the production of any isoprenoid given that an enzymatic pathway from mevalonate to the isoprenoid of interest was also expressed.

Microarray Analysis of HMG-CoA Toxicity in E. coli: Inhibition of Fatty Acid Biosynthesis In order to identify the mode of toxicity associated with the accumulation of HMG-CoA in E. coli, transcriptomic analyses of the strains harboring the mevalonate pathway constructs were preformed. mRNA transcript levels of E. coli DP10 harboring pBad33MevT were compared to E. coli DP10 harboring pMevT(C159A), the inactive pathway control. The mRNA transcript profiles of both strains at time points after induction with arabinose were also compared to the respective transcript profiles of the strains prior to induction.

Starter cultures of DP10 harboring either pBad33MevT & pBad18 (active mevalonate pathway) or pMevT(C159A) & pBad18 (inactive mevalonate pathway control) were inoculated from single colonies and incubated overnight at 37° C. in defined C medium (see above) supplemented with 0.06% glucose (to repress the $P_{BAD}$ promoters) and 50 µg/ml chloramphenicol and carbenicillin (for plasmid selection). Overnight starter cultures were diluted to an $OD_{600}$ of approximately 0.05 in defined C medium with antibiotics, incubated at 37° C. with continuous shaking and induced with the addition of 1.33 mM (0.02%) arabinose at $OD_{600}$ of ~0.25-0.30. Samples were taken for microarray analysis prior to induction and then ~1 hour and ~3 hours post-induction from E. coli DP10 pBAD33MevT & pBad18 and E. coli DP10 pMevT(C159A) & pBad18 cultures to capture the early response dynamics of the host to the HMG-CoA toxicity. The transcriptional profile analysis of each strain's individual time course (post-induction samples vs. pre-induction) as well as cross-strain profiles (E. coli DP10 pBAD33MevT & pBad18 vs. E. coli DP10 pMevT(C159A) & pBad18) were performed in triplicate.

Accumulation of HMG-CoA Induces Membrane Stress.

Figure 8A:
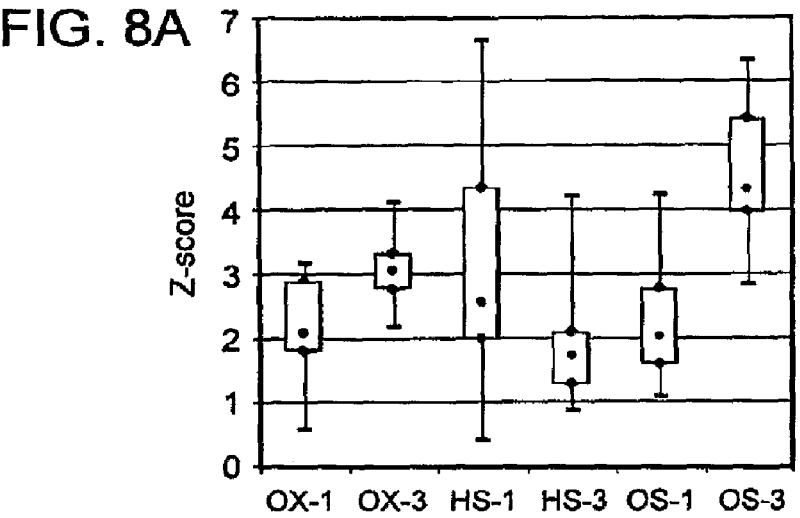
Figure 8B:
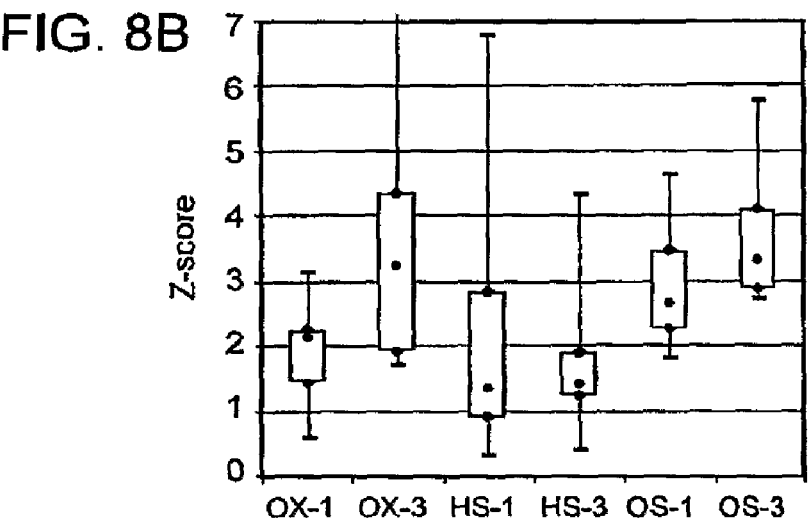
Figure 8C:
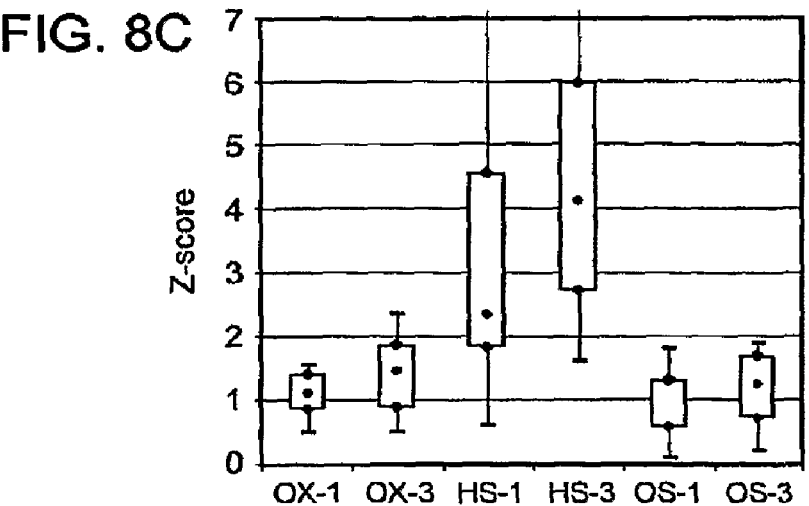

E. coli has evolved several stress response regulons that allow the organism to adapt to environmental changes. The transcriptional modulation of these regulons provided insight into the toxicity associated with HMG-CoA accumulation in the mevalonate-producing strain (FIGS. 8A-C). First, microarray analysis showed there was an up-regulation of many genes encoding osmoregulatory activities in the mevalonate-producing E. coli DP10 containing pBAD33MevT, including those encoding trehalose biosynthetic enzymes (otsAB operon), an omoprotectant/proton symporter (prop), betaine biosynthetic proteins (bet operon), and osmC, osmY, and osmE, which are osmotically-inducible genes whose products have not been fully annotated (FIGS. 8A-C; and FIG. 9). The up-regulation of these genes suggested that the host was regulating osmotic pressure as if it were exposed to an increase in medium osmolality. No similar osmotic stress response was observed in the inactive control strain (DP10 harboring pMevT(C159A)), and, indeed, when the two strain's mRNA profiles were compared directly using DNA microarrays the expression profiles of the osmo-regulatory genes were significantly higher in the mevalonate-producing strain than in the inactive control strain.

The signal that controls activation of the osmotic stress response in E. coli has traditionally been assumed to be the $K^+$ flux across the membrane as well as the turgor pressure of the cell (Csonka, L. N. and W. Epstein, Osmoregulation. In A. Böck, R. Curtiss III, J. B. Kaper, F. C. Neidhardt, T. Nyström, K. E. Rudd, and C. L. Squires (ed.), EcoSal-Escherichia coli and Salmonella: cellular and molecular biology. On the Internet at ecosal.org; 1996). Recent evidence has questioned the role of turgor pressure in osmosensing by E. coli (Culham, et al., Biochemistry 42(2): p. 410-420 (2003)); analysis of ProP, the osmosensor in E. coli, has revealed that membrane composition, specifically macromolecular crowding, is the major signal used by the cell for governing its long-term response to changes in osmolality (Tsatskis, et al., J Biol Chem 280(50): 41387-41394 (2005)). While the short term response to changes in osmotic pressure is controlled by $K^+$ flux, long term responses are governed by alterations membrane properties. Thus, the very specific up-regulation of the osmoregulatory stimulon observed in the mevalonate-producing strain suggests that HMG-CoA accumulation indirectly alters the membrane properties of the heterologous host.

The active pathway strain (DP10 harboring pBad33MevT) also exhibited a significant increase in expression of oxidative stress-associated genes (FIGS. 8A-C; and FIG. 9). The up-regulated genes included dps (encoding a DNA binding protein), the suf operon (iron-sulfur cluster repair), and ahpC (alkylhydroperoxide reductase). Additionally, when the two strains were compared directly, the peroxidase-encoding gene, katG, was also observed to be up-regulated in the mevalonate-producing strain. These genes are members of the OxyR regulon, and their up-regulation is consistent with increased hydrogen peroxide production in E. coli DP10 containing pBAD33MevT. There was no significant activation of oxidative stress genes in the inactivated-pathway control strain (DP10 harboring pMevT(C159A)); therefore, the $H_2O_2$ response appears to be specific to the accumulation of HMG-CoA.

The major source of $H_2O_2$ in the cell is the respiratory electron transport chain (Gonzalez-Flecha and Demple, *J Biol Chem* 270(23): 13681-13687 (1995)); therefore, a membrane-associated stress would be expected to increase the production of reactive oxygen species. In fact, it has been reported that hyperosmotic stress does induce excessive redox-cycling, which increases the transcription of several genes in the OxyR regulon as well as katE, which encodes hydrogen peroxidase II (Smirnova, et al., *FEMS Microbiol Lett.* 186(2): 209-213 (2000)). All these genes were up-regulated in the active pathway strain.

HMG-CoA-Mediated Growth Inhibition Slows Growth and Protein Translation.

The expression of the mevalonate pathway on pBAD33MevT in *E. coli* elicited a moderate heat shock response consistent with heterologous protein expression. As shown in the time course expression profiles of pBAD33MevT (FIGS. 8A-C; and FIG. 9), many members of the heat shock regulon were induced at 1 hour post-induction, but then expression of these genes decreased at 3 hours post induction. The heat shock regulon genes, which were most highly expressed in DP10 containing pBAD33MevT, were those encoding the chaperone ClpB, the molecular chaperone DnaK, and the small heat shock proteins IbpA and IbpB. In contrast, the expression of heat shock genes in DP10 containing pBAD33MevT(C159A) continued to increase over the entire time course.

The induction of the heat shock regulon in response to recombinant protein production has been well documented. High levels of heterologous protein production from inducible expression systems increase the transcription of genes encoding molecular chaperones and proteases and decrease the expression of ribosomal RNA's and proteins (Dong, et al., *J Bacteriol* 177(6):1497-1504 (1995)). It has been documented that ClpB, IbpA, IbpB and DnaK function together as a disaggregase to control the formation and dissolution of inclusion bodies in *E. coli* (Mogk, et al., *Curr Biol* 14(2): R78-80. (2004)). Inclusion body formation is dependent on kinetic competition between aggregation and folding rates (Rudolph, R., In: Cleland J L, Craik C S (eds) Principles and practice of protein folding. Wiley, New York. 1996.) and is influenced by growth medium (Swartz, J., *Escherichia coli* Recombinant DNA Technology. In A. Böck, R. Curtiss III, J. B. Kaper, F. C. Neidhardt, T. Nyström, K. E. Rudd, and C. L. Squires (ed.), EcoSal-*Escherichia coli* and *Salmonella*: cellular and molecular biology. [Online.], 1996), culture temperature (Neubauer, P. et al. Recombinant protein production with prokaryotic and eukaryotic cells. A comparative view on host physiology, Kluwer Academic Publishers, Dortrecht, The Netherlands, p 196, 2001), or the presence of folding-rate limiting structures such as disulfide bonds (Rinas, et al. *Biotechnology* 10(4): 435-440 (1992)). This "inclusion body stimulon" was more induced in DP10 containing pBAD33MevT during the first hour post induction but then expression declined (FIGS. 8A-C; and FIG. 9).

FIGS. 8A-C. Box plots of transcript expression ratios of stress response regulons. Box plots of transcript expression ratios of genes in the heat shock (HS), oxidative (OX) and osmotic (OS) stress regulons at one hour (HS-1, OX-1, OS-1) and three hours (HS-3, OX-3, OS-3) post-induction expressed as Z-scores from the loess analysis in the SNO-MAD software. The microarray comparisons were: (A) *E. coli* DP10 pBAD33MevT & pBad18 time course (relative to pre-induction) (B) the *E. coli* DP10 pBAD33MevT & pBad18 vs. *E. coli* DP10 pMevT(C159A) & pBad18 time course (relative to the inactive pathway control) and (C) the *E. coli* DP10 pMevT(C159A) & pBad18 time course (relative to pre-induction). A strong activation of the oxidative and osmotic stress regulons was observed in DP10 harboring pBAD33MevT but not in DP10 harboring pBAD33MevT (C159A). The heat shock regulon was activated early in DP10 containing pBAD33MevT but overall expression of the regulon lowered at the three hour time point. The heat shock regulon remained highly activated in DP10 containing pMevT(C159A) control strain.

FIG. 9: Transcript expression ratios of stress regulon genes. Transcript expression ratios of stress regulon genes in the *E. coli* DP10 pBAD33MevT & pBad18 time course (relative to pre-induction; labeled "MevT"), the *E. coli* DP10 pBAD33MevT & pBad18 vs. *E. coli* DP10 pMevT(C159A) & pBad18 time course (relative to the inactive pathway control; labeled "MevT vs. MevT-C159A") and the *E. coli* DP10 pMevT(C159A) & pBad18 time course (relative to pre-induction; labeled "MevT-C159A"). Both fold-changes and local Z-scores (in parenthesis) are shown. Stress regulon genes not shown did not change significantly in the comparison.

The down-regulation of the heat shock response in the mevalonate-producing strain is likely due to the strong down-regulation of protein synthesis observed as HMG-CoA accumulated. There was a 2-5 fold drop in expression of all ribosomal protein genes post-induction in active-pathway strain as compared to the inactive-pathway control. A strong heat shock response in *E. coli* has been documented to result in a down regulation of the ribosomal protein genes (Dong, et al, *J Bacteriol* 177(6): 1497-1504 (1995); Rinas, *Biotechnol Prog.* 12(2): 196-200 (1996)), yet the inactive pathway strain, which had a stronger heat shock response than the active pathway, did not exhibit a similar drop in expression of the ribosomal genes. The expression of the gene encoding the ribosome modulation factor, rmf, was up-regulated significantly in the HMG-CoA-stressed cells. This gene, whose product dimerizes the 70S ribosome and reduces translational capacity, is generally expressed during the transition to stationary phase or during conditions of slow growth (Izutsu, et al. *Genes Cells* 6(8): 665-676 (2001)). The apparent down-regulation of the translational machinery is likely part of a coordinated response in the HMG-CoA-stressed cells, which would have limited heterologous protein synthesis and, in turn, lead to a down-regulation of the heat shock regulon as was observed in the pBAD33MevT time course. Conversely, since DP10 harboring pBAD33MevT(C159A) was not stressed by HMG-CoA accumulation, it was able to maintain a higher rate of protein synthesis, which would increase activation of heat-shock regulon genes at later time points.

Fatty Acid Biosynthesis is Altered by HMG-CoA Accumulation.

There was a consistent up-regulation observed in the expression of the β-ketoacyl-ACP synthase I (encoded by fabB), both over the *E. coli* DP10 pBAD33MevT & pBad18 growth time course (post-induction compared to pre-induction) and in the cross strain comparison (*E. coli* DP10 pBAD33MevT & pBad18 vs. *E. coli* DP10 pBAD33MevT (C159A) & pBad18, Table 3).

TABLE 3

Changes in expression of fatty acid biosynthetic genes

|  | 1 hour | 3 hours |
|---|---|---|
| accB | 2.9 (4.3) | 3.3 (4.3) |
| cfa | 1.4 (2.2) | 3.1 (5.4) |
| bioD | 1.6 (2.2) | 3.1 (5.3) |
| accC | 2.4 (3.1) | 3.0 (4.2) |
| fabD | 1.1 (0.9) | 2.6 (4.8) |
| fabB | 2.3 (3.4) | 2.6 (4.5) |
| bioA | 1.3 (1.4) | 2.4 (3.5) |
| bioB | 1.9 (2.7) | 2.2 (4.1) |
| fabH | 1.7 (2.0) | 2.1 (3.9) |

Table 3 shows expression values and the Z-scores (in parenthesis) for fatty acid biosynthetic genes that exhibited a biologically significant up-regulation in DP10 harboring pBAD33MevT as compared to the inactive pathway control strain (DP10 harboring pMevT(C159A)) in the microarray analysis.

There was also an up-regulation in the expression of malonyl-CoA:ACP transacylase (MAT, encoded by fabD) observed in the ~3 hour post-induction sample with a smaller up-regulation of fabH, which shares a promoter with fabD (though there can be extensive post-transcriptional processing of these transcripts). FabD is the only enzyme in *E. coli* that interacts with malonyl-CoA directly, and this occurs during the transfer of the malonyl moiety from CoA to the acyl carrier protein (ACP) (Cronan, J. E. and C. O. Rock, Biosynthesis of Membrane Lipids. In A. Böck, R. Curtiss III, J. B. Kaper, F. C. Neidhardt, T Nyström, K. E. Rudd, and C. L. Squires (ed.), EcoSal-*Escherichia coli* and *Salmonella*: cellular and molecular biology. [Online.], 1996). There were genes involved in the initial steps of fatty acid biosynthesis (FAB) whose expression was up-regulated in *E. coli* DP 10 pBAD33MevT & pBad18 in comparison to *E. coli* DP10 pMevT(C159A) & pBad18. These included those encoding proteins used in biotin biosynthesis (bioA and bioB) and the acetyl-CoA carboxylase genes (ACC).

These expression changes in the fatty acid biosynthetic genes are consistently detected 1 and 3 hours post-induction in *E. coli* expressing the heterologous MevT pathway, which accumulates HMG-CoA. In *E. coli*, the only known use of malonyl-CoA is as a precursor to fatty acids and lipids in the type II fatty acid biosynthesis pathway (Rock and Jackowski. *Biochem Biophys Res Commun* 292, 1155-1166 (2002)) (FIG. 3). The accumulation of malonyl-CoA is the classic signature of inhibition of fatty acid biosynthesis (Subrahmanyam and Cronan. *J Bacteriol* 180(17): 4596-602 (1998); Heath and Rock. *J Biol Chem* 270, 15531-15538 (1995); Furukawa et al. *J Bacteriol* 175, 3723-3729 (1993); Heath et al. *Appl Microbiol Biotechnol* 58(6): 695-703 (2002)). Additionally, it has been shown in a similar organism with a Type II FAB system challenged by an antibiotic that targets β-ketoacyl-ACP synthase I and up-regulates the gene encoding that enzyme (Betts, et al. *Antimicrob Agents Chemother* 47(9): 2903-2913. (2003)). Thus, the microarray data and the metabolite data both indicate a situation in which HMG-CoA inhibits fatty acid biosynthesis, and the organism adapts to this condition partially by up-regulating genes involved in that pathway.

In *Escherichia coli* and most bacteria, malonyl-CoA is produced from acetyl-CoA by the action of acetyl-CoA carboxyltransferase/carboxylase a heterotetramer composed of three enzymes and a carrier protein encoded by accA, accB, accC, and accD. For function of the enzyme complex, the carrier protein, AccB, is first activated by the addition of a cofactor, biotin, and a carboxyl group. Once produced, the malonate moiety of malonyl-CoA is transferred from the co-enzyme A carrier to acetyl carrier protein (ACP) by the action of malonyl-CoA:ACP transacylase (FabD), forming malonyl-ACP.

There are three routes of entry into the fatty acid elongation cycle. Malonyl-ACP can condense with acetyl-ACP to form acetoacetyl-ACP by the action of β-ketoacyl-ACP synthases I and II (FabB and FabF), or malonyl-ACP undergoes a condensation reaction with acetyl-CoA catalyzed by β-ketoacyl-ACP synthases III (FabH). Additionally, FabB can convert malonyl-ACP to acetyl-ACP and then initiate the cycle. After acetoacetyl-ACP is formed it proceeds through the remainder of the fatty acid elongation cycle (FIG. 3), see Rock and Jackowski ((2002) supra) for review. In addition to initiating synthesis, malonyl-ACP is added to the elongating fatty acid molecule, again by the action of FabB and FabF.

All fatty acids are elongated by the elongation cycle until the acyl-ACP reaches 10 carbons in length. At this point, as depicted in FIG. 10, saturated and unsaturated fatty acid biosynthesis pathways split.

Figure 10:
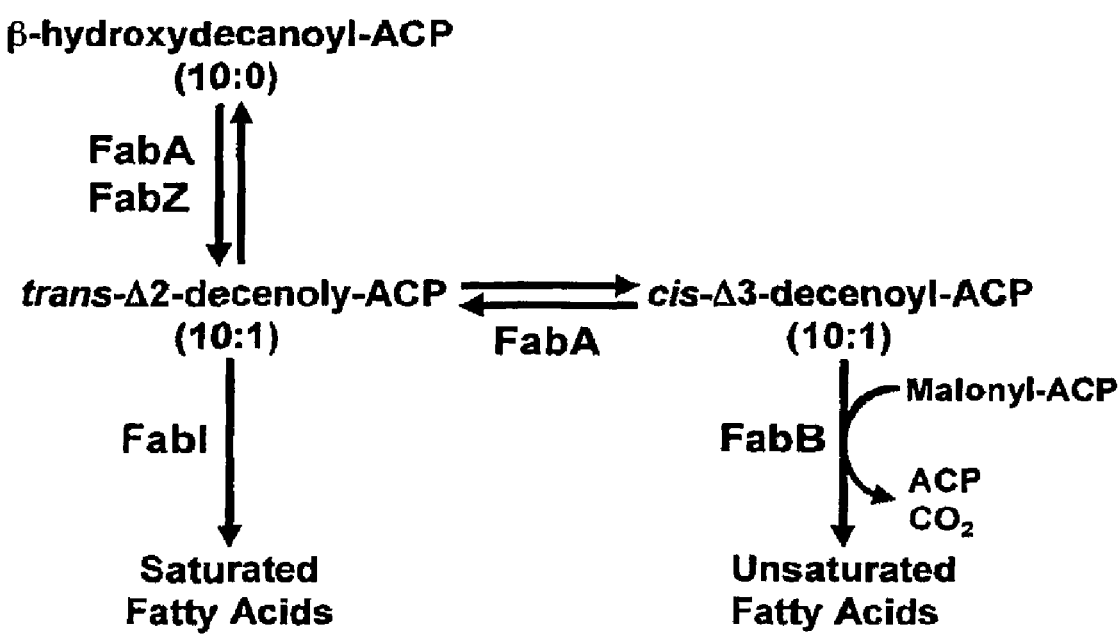
FIG. 10 depicts a branch point in unsaturated fatty acid biosynthesis of type II systems.

FIG. 10. Branch point in unsaturated fatty acid biosynthesis of type II systems. FabA is the only *E. coli* dehydratase capable of isomerizing trans-Δ3-decenoyl-ACP to cis-Δ2-decenoyl-ACP. The cis intermediate is elongated first by FabB and further by subsequent enzymes to form the unsaturated fatty acids. The trans intermediate is reduced by FabI and is further elongated to form the saturated fatty acids. See, Rock and Jackowski. *Biochem Biophys Res Commun* 292, 1155-1166 (2002).

In addition to dehydratase activity in the elongation cycle, FabA (β-hydroxydecanoyl-ACP dehydratase) isomerizes trans-$\Delta^2$-decenoyl-ACP to cis-$\Delta^3$-decenoyl-ACP, the initial step in unsaturated fatty acid biosynthesis. Once formed, cis-$\Delta^3$-decenoyl-ACP is subsequently elongated by FabB, the major rate controlling step in unsaturated fatty acid biosynthesis. Both enzymes are required for synthesis of unsaturated fatty acids and overexpression or mutation of either gene alters the saturated:unsaturated fatty acid ratio in *E. coli*. Elongation of unsaturated fatty acids is also carried out by FabF which specifically elongates cis-$\Delta^9$-16:1-ACP to cis-$\Delta^{11}$-18:1-ACP in response to temperature. The acyl-ACP end products of fatty acid synthesis are used for the formation of membrane phospholipids. However, intermediates of the pathway are also used in the biosynthesis of vitamins and other cofactors.

Fatty acids in *E. coli* and other bacteria may also be altered after biosynthesis. One common conversion is the synthesis of cyclopropane fatty acid derivatives from the 16:1 and 18:1 fatty acid components of phospholipids bilayer by the action of cyclopropane fatty acid synthase (Cfa). The specific physiological role of cyclopropane fatty acid derivates is not known; however, increases in cyclopropane fatty acids in *E. coli* cells have been associated with the onset of late exponential/early stationary phase of cell growth and stringent response to depletion of substrates ((Grogan and Cronan. *Microbiol Mol Biol Rev* 61, 429-441 (1997)).

Taking the observations together, it appears that accumulating intracellular HMG-CoA inhibits an early step in type II fatty acid biosynthesis, likely the conversion of malonyl-CoA to malonyl-ACP by FabD or the initiation of fatty acid elongation by FabB.

Fatty Acid Analysis of Growth Inhibited Strains is Consistent with Block of Fatty Acid Biosynthesis To further test the model of HMG-CoA toxicity, the fatty acid compositions of growth inhibited strains were analyzed. Using a two plasmid system in *E. coli* DP10, the changes in the fatty acid composition over time were compared between cells overexpressing tHMGR (pBad33MevT & pBad18HMGR), cells expressing only the MevT operon (pBad33MevT & pBad18), and a control strain expressing the inactive MevT operon (pMevT(C159A) & pBad18).

Cultures were incubated and induced in defined C media as above. Briefly, starter cultures of DP10 harboring either pBad33MevT & pBad18 (active mevalonate pathway), pBad33MevT and pBad18HMGR (increased expression of tHMGR), or pMevT(C159A) & pBad18 (inactive mevalonate pathway control) were inoculated from single colonies and incubated overnight at 37° C. in defined C medium (see above) supplemented with 0.06% glucose (to repress the $P_{BAD}$ promoters) and 50 µg/ml chloramphenicol and carbenicillin (for plasmid selection). Overnight starter cultures were diluted to an $OD_{600}$ of approximately 0.05 in defined C medium with antibiotics, incubated at 37° C. with continuous shaking and induced with the addition of 1.33 mM (0.02%) arabinose at $OD_{600}$ of ~0.25-0.30. Samples were taken for fatty acid analysis and dry cell weight determination immediately prior to induction and then at multiple time points after induction.

Figure 11A:
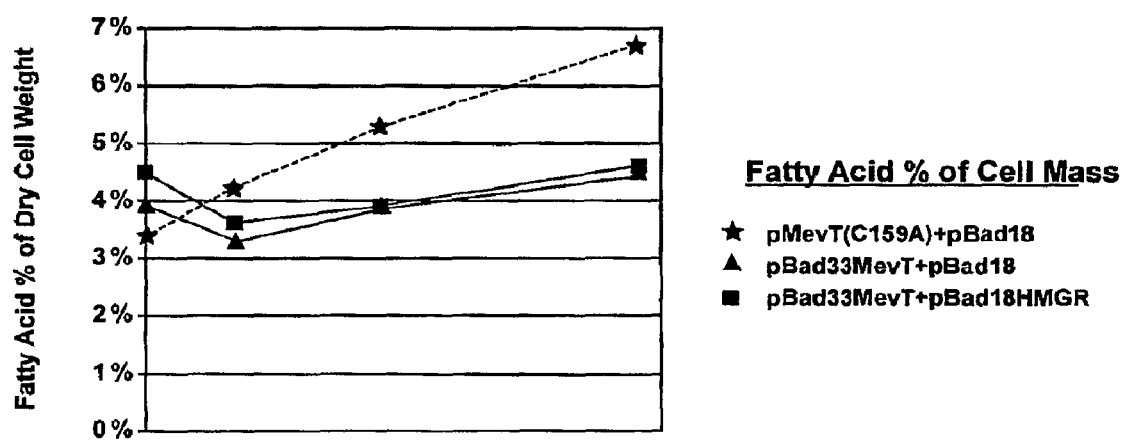
FIGS. 11A-D depict fatty acid analysis of cells overexpressing tHMGR and MevT operons.

The fatty acid composition of the three different strains changed significantly over time, as well as the percentage of cell biomass that was composed of fatty acids. In both strains with an active MevT operon (DP10 containing pBad33MevT & pBad18 and DP10 containing pBad33MevT & pBad18HMGR) the fatty acid percent of dry cell weight was lower at later times than in the inactive pathway control strain (DP10 containing pMevT(C159A) & pBad18, FIG. 11A).

Figure 11B:
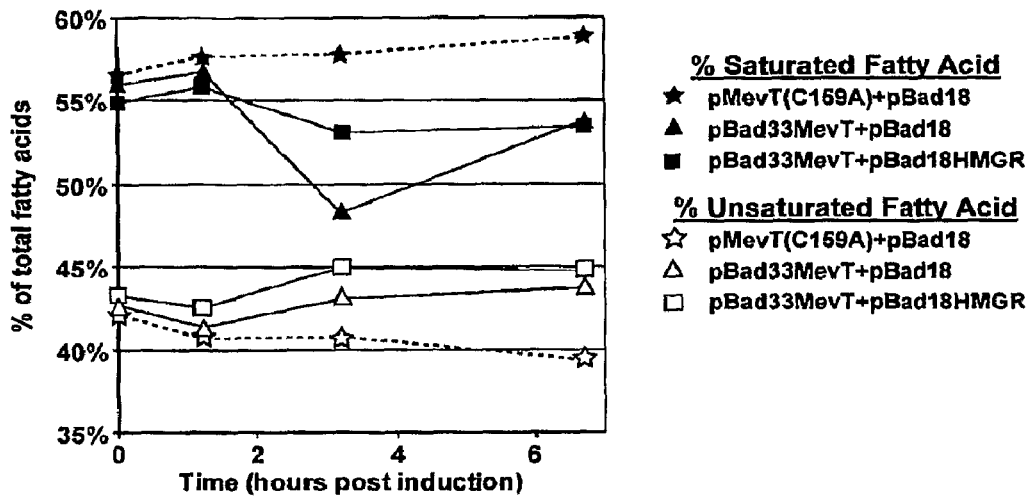

In comparison to the inactive pathway control strain, the total saturated fatty acid percentage of cells harboring the active MevT operons decreased over time, while the total unsaturated fatty acid percentage increased (FIG. 11B). Interestingly, cells overexpressing tHMGR (pBad33MevT & pBad18HMGR) accumulated less unsaturated fatty acid than cells expressing MevT alone. Saturated fatty acid levels in strains with additional tHMGR were also slightly higher than in the MevT only strain at later times, but remained significantly lower than the inactive pathway control.

Both observations appear consistent with inhibition of FabD in the engineered strains. As HMG-CoA accumulates in cells overexpressing MevT, it was observed that expression of both fabB and fabD are up-regulated. Inhibiting FabD activity restricts replenishment of the long-chain acyl-ACPs, the main product of the fatty acid biosynthesis cycle, while simultaneously, activity of unsaturated fatty acid synthesis increases (rate controlled by FabB). Therefore, one would expect to observe that the limited saturated fatty acids that are produced are rapidly converted to unsaturated fatty acids by up-regulation of fabB. If FabB were inhibited, an overall decrease in unsaturated fatty acid content would be expected (Broekman and Steenbakkers. *J Bacteriol* 116, 285-289 (1973))—opposite of what is observed. The observation that increased expression of tHMGR, which reduces HMG-CoA accumulation, also results in less of an increase in the unsaturated: saturated fatty acid ratio lends further support to this model.

Figure 11C:
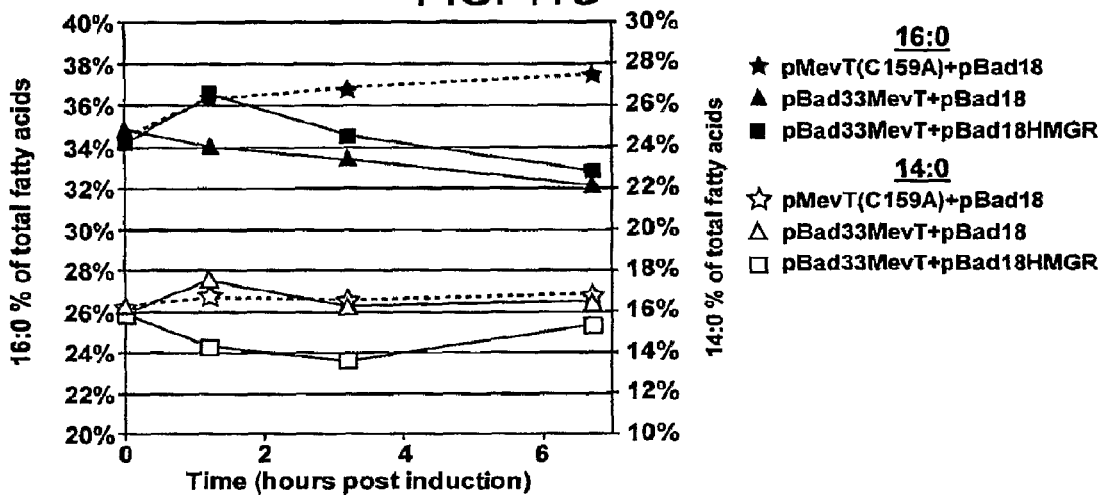
Figure 11D:
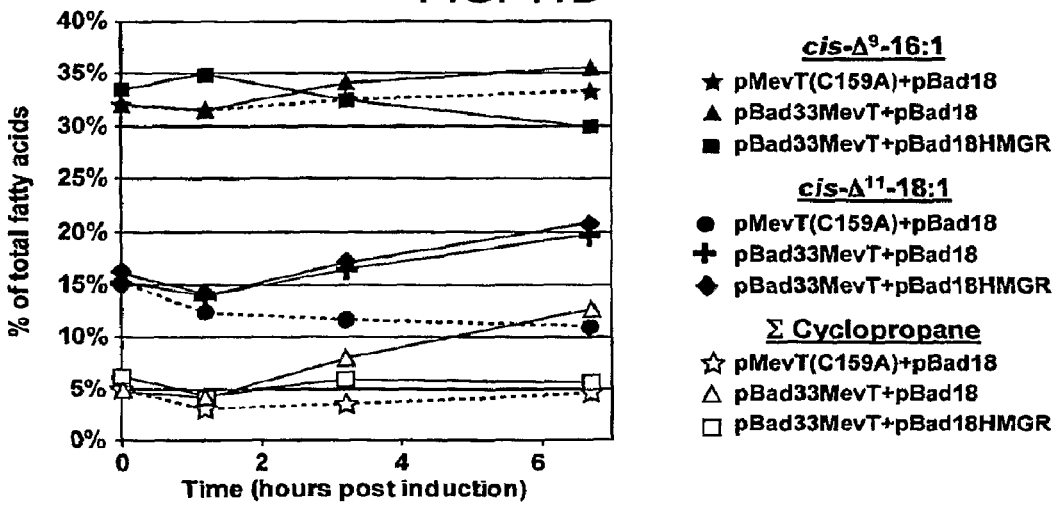

The profiles of the individual fatty acids also changed with the expression of the different constructs. The more prominent changes in cells expressing MevT alone, in comparison to the inactive pathway control strain, were a reduction in saturated fatty acid 16:0 and significant increases in unsaturated fatty acid cis-$\Delta^{11}$-18:1 and cyclopropane fatty acids. (FIGS. 11C and 11D). Co-expression of MevT and tHMGR resulted in less of a decrease in 16:0 and less of an increase in the total cyclopropane fatty acids. No significant difference in cis-$\Delta^9$-16:1 was observed between strains while 14:0 (the sum of the percentage of saturated 14:0 and 3-hydroxyl-14:0) decreased slightly with increased expression of tHMGR.

The reduction in 16:0 content in cells harboring pBad33MevT is consistent with the growth improvement observed when cultures were supplemented with exogenous 16:0 fatty acid (see Example 2). In comparison, the increase in cis-$\Delta^{11}$-18:1, decrease in 16:0, and non-change in cis-$\Delta^9$-16:1 content of growth inhibited cells is also similar to fatty acid profiles observed when cell growth is arrested by co-enzyme A depletion (Jackowski and Rock. *J Bacteriol* 166, 866-871 (1986)). However, this possible mode of cytotoxicity for cells harboring pBad33MevT is unlikely for analysis of intracellular acyl-CoA levels actually showed an increase in free co-enzyme A in those strains (FIG. 7A). Another possibility, is that as inhibition of FabD slows entry of new acyl-ACP chains into the biosynthesis cycle, while FabF activity is constant (no change in expression in microarray comparisons) and continues to elongate cis-$\Delta^9$-16:1 molecules to cis-$\Delta^{11}$-18:1; thereby cis-$\Delta^{11}$-18:1 is enriched at the expense of cis-$\Delta^9$-16:1 at the expense of saturated fatty acids.

The other substantial difference in the fatty acid profiles was the increased percentage of cyclopropane derivatives of unsaturated fatty acids in cells harboring pBad33MevT. To date, the increase of cyclopropane fatty acids in *E. coli* cells have only been associated with the onset of late exponential/ early stationary phase of cell growth and stringent response to depletion of substrates (Grogan and Cronan (1997) supra). The growth inhibited strains may be transitioning to a stationary phase of growth while the control strain is still growing exponentially. This observation does not confirm a specific cause of toxicity.

The fatty acid profiles of the growth inhibited strains do not completely match those of previous studies on *E. coli* containing temperature sensitive fabD mutant alleles. Transferring fabD mutants from permissive to non-permissive temperatures resulted in an increase in 14:0 content and a concomitant decrease in unsaturated fatty acids cis-$\Delta^9$-16:1 and cis-$\Delta^{11}$-18:1 (Harder et al. (1974) supra). However, it is expected that changes in fatty acid composition of the cells harboring pBad33MevT would not completely match the fabD mutants previously studied, for the temperature sensitive mutations completely inactivated enzyme function and killed cells at non-permissive temperatures. Although the accumulation of HMG-CoA inhibits cell growth, the inhibited strains maintain some viability by reprogramming gene expression (as seen by the microarray data). Additionally, the fatty acid profile of the wild-type, control strain in the previous study ((Harder et al. (1974) supra)) is substantially different than the fatty acid profiles of either *E. coli* DP10 harboring pMevT(C159A) (FIGS. 11B, 11C, and 11D) or DP10 without plasmid.

FIGS. 13A-D: Fatty acid analysis of cells over-expressing tHMGR and MevT operons. Fatty acid composition of *E. coli* DP10 harboring two plasmid systems for the production of mevalonate: inactive pathway control (pMevT(C159A)+ pBad18), MevT operon expressed alone (pBad33MevT+ pBad18), and MevT co-expressed with additional tHMGR (pBad33MevT+pBad18HMGR). (A) Percentage of cell mass that is fatty acid. (B) Percentage of total saturated and unsaturated fatty acids. (C) Profile of saturated fatty acids 14:0 and 16:0. (D) Profile of unsaturated fatty acids cis-$\Delta^9$-16:1, cis-$\Delta^{11}$-18:1, and total percentage of cyclopropane fatty acids cis-$\Delta^9$-17:0 and cis-$\Delta^{11}$-19:0 (Σ Cyclopropane). The t=0 sample for fatty acid analysis was taken immediately prior to induction. Saturated fatty acid 12:0 did not vary significantly between strains. Percentage of 14:0 includes 3-hydroxyl-14:0. Percentage cis-$\Delta^9$-16:1 and cis-$\Delta^{11}$-18:1 includes their cyclopropane derivatives.

Fatty acid analysis of strains inhibited by HMG-CoA accumulation depicts a general alteration of fatty acid metabolism consistent with inhibition of fatty acid biosynthesis. Fatty acid profiles of cells overexpressing MevT appeared to show the inhibition of FabD in the context of up-regulated fabB. A decrease in 16:0 content was observed in growth-inhibited cells, which correlates well with the fatty acid supplementation studies (see Example 2). The fatty acid compositions alone do not outright prove that FabD is inhibited, but they appear to disprove the inhibition of FabB. Considering the results of the media supplementation studies and fatty acid analysis together, it is likely that high intracellular levels of HMG-CoA inhibit FabD and thereby limit fatty acid biosynthesis. However, this inhibition can also be avoided by efficiently balancing carbon flux through the heterologous mevalonate pathway.

Example 2

Supplementing Growth Media with Specific Fatty Acids Alleviates Growth Inhibition Caused by the Accumulation of HMG-CoA in Engineered E. coli To further test the action of HMG-CoA on E. coli metabolism and design a method for alleviating growth inhibition, cells expressing the various MevT constructs were supplemented with fatty acids to test for deficiencies. E. coli strains carrying a temperature sensitive fabD allele have been shown to grow at non-permissive temperatures with the addition of either palmitic acid (16:0) (Harder et al. J Biol Chem 249, 7468-7475 (1974)) or a combination of palmitic and palmitoleic acid (cis-$\Delta^9$-16:1) (Harder et al. Proc Natl Acad Sci U S A 69, 3105-3109 (1972)), but not cis-$\Delta^9$-16:1 (Harder et al., (1974) supra). Due to the role of FabB in unsaturated fatty acid biosynthesis, temperature sensitive mutants of fabB show reduced unsaturated fatty acid content under non-permissive conditions but can grow with exogenous oleic acid (cis-$\Delta^9$-18:1) (Broekman and Steenbakkers. J Bacterial 116, 285-289 (1973)).

E. coli DP10 cells harboring pBad33, pBad33MevT, pMevT(C159A), pHMGS, or pHMGSR were incubated and induced in 96-well plates in fully defined C medium containing 50 µg/ml chloramphenicol (see material and methods) with supplemental cis-$\Delta^9$-18:1, 16:0, cis-$\Delta^9$-16:1, or a equal mass mixture of 16:0 and cis-$\Delta^9$-16:1. As stated above, the fatty acids were purchased from Sigma and employed at a concentration of 100 µg/ml in the presence of 400 µg/ml Brij (Sigma). Starter cultures of DP10 harboring the mevalonate pathway constructs were inoculated from single colonies and incubated overnight at 37° C. in defined C medium supplemented with 0.06% glucose (to repress the $P_{BAD}$ promoters) and chloramphenicol (for plasmid selection). Overnight starter cultures were used to inoculate fresh C medium in a 96-well microtiter plate. The microtiter cultures were incubated at 37° C. with continuous shaking and induced with the addition of 1.33 mM (0.02%) arabinose approximately 2 hours after inoculation. The optical density of the cultures was measured using a microtiter plate reader (SpectraMax, Molecular Devices).

Figure 12A:
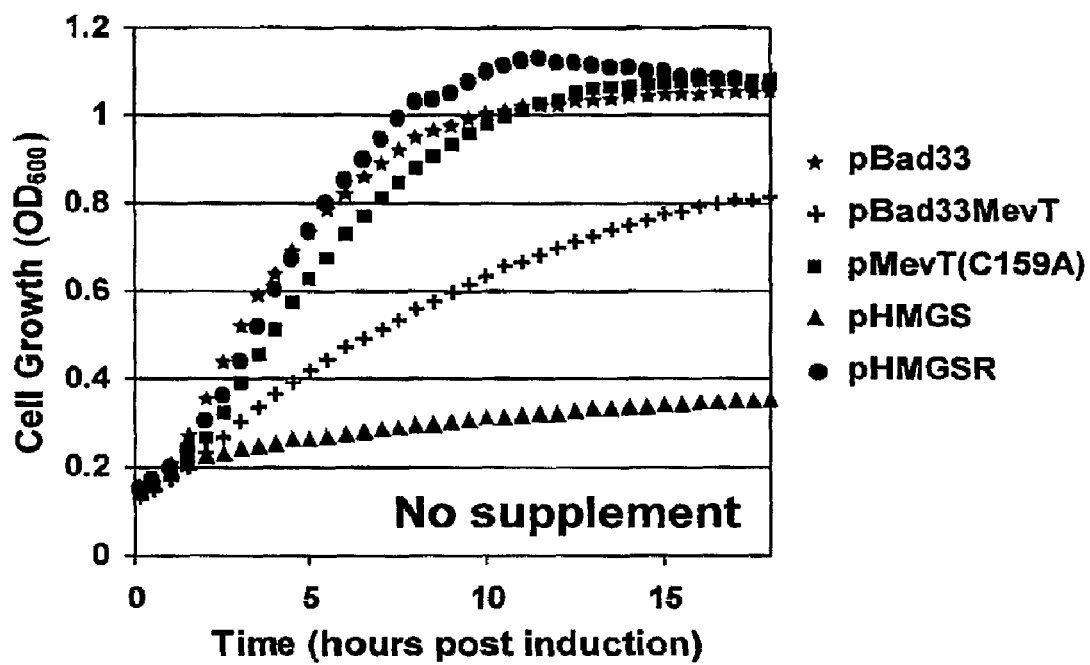
FIGS. 12A-E depict screening fatty acid supplements for increased growth of cells inhibited by the accumulation of HMG-CoA.
Figure 12B:
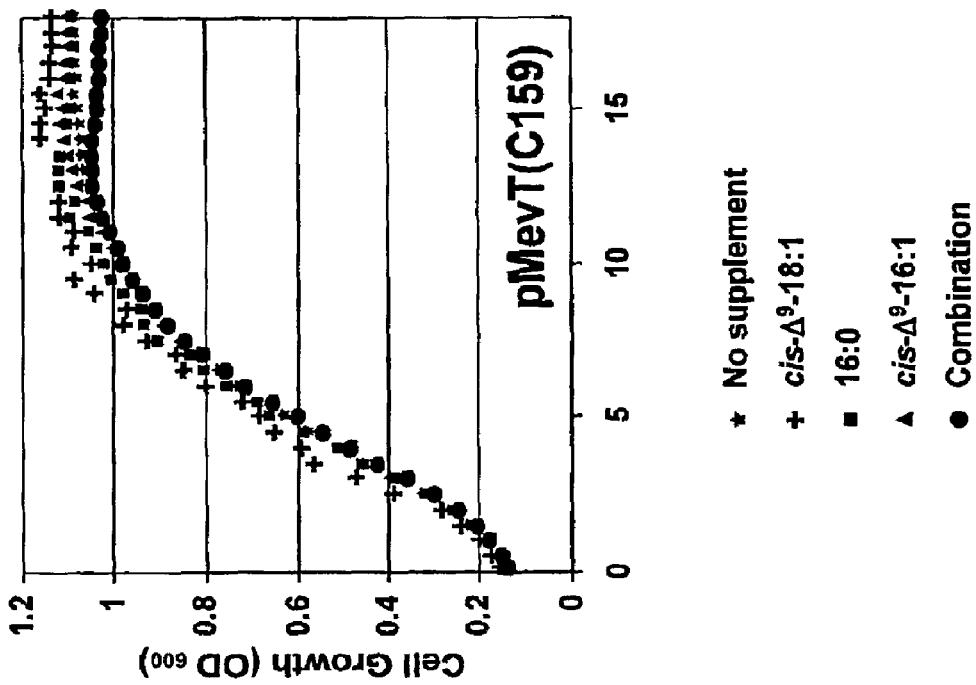
Figure 12C:
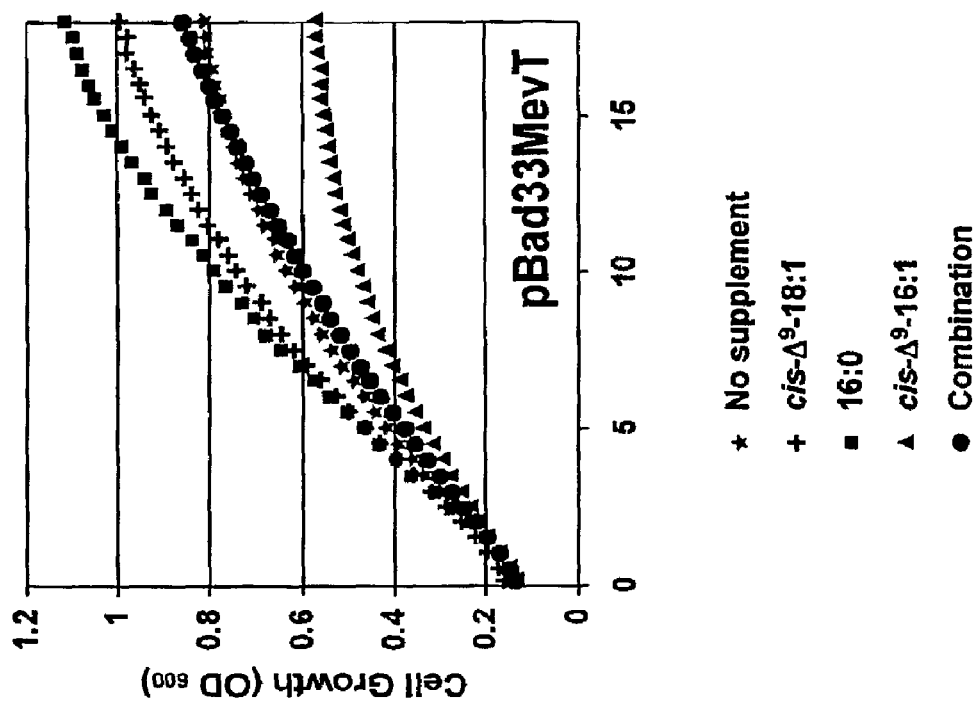
Figure 12E:
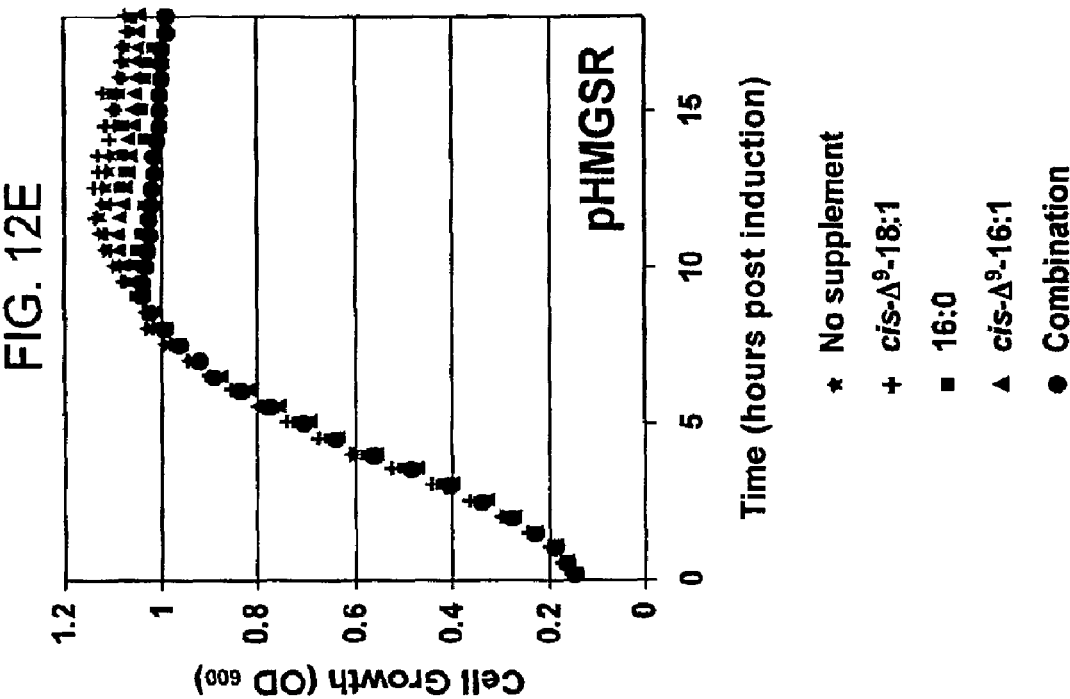
Figure 12D:
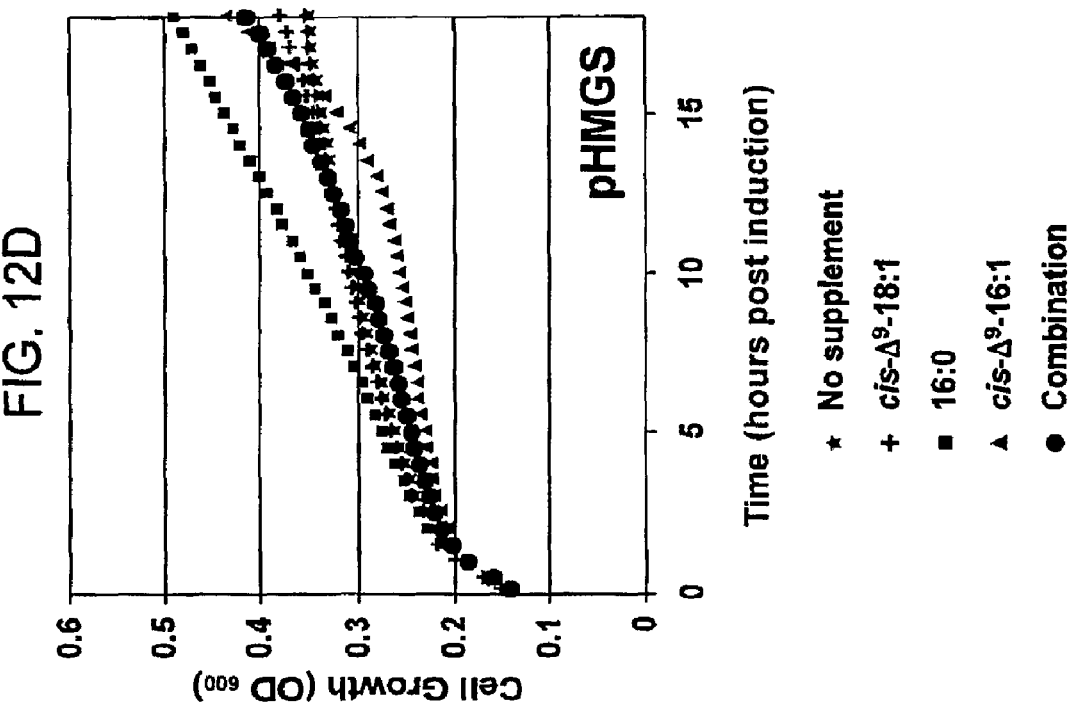

As demonstrated in the previous experiments with non-supplemented media, expression of the MevT operon from pBad33MevT or expression of HMGS alone (pHMGS) caused growth inhibition, while expression of the inactive operon, MevT(C159A) (pMevT(C159A)) or co-expression of HMGS and HMGR (pHMGSR) did not (FIG. 12A). Fatty acid supplementation had no effect on the growth of cells harboring pMevT(C159A) or pHMGSR (FIGS. 12C and 12E); however, the growth of strains containing pBad33MevT and pHMGS were significantly affected (FIGS. 12B and 12D). The addition of 16:0 and, to a lesser extent, cis-$\Delta^9$-18:1 improved the growth of MevT expressing cells (pBad33MevT), while only the addition of 16:0 had a clear, positive effect on the growth of cells containing pHMGS. Interestingly, the addition of cis-$\Delta^9$-16:1 proved to be detrimental to the growth of cells harboring either pBad33MevT or pHMGS, while cells incubated with the combination of 16:0 and cis-$\Delta^9$-16:1 grew similar to non-supplemented cultures. From the varying response of the growth inhibited cells to fatty acid supplementation, fatty acid biosynthesis appeared to be affected by the accumulation of HMG-CoA and the primary inhibition of the pathway appears to occur at FabD.

FIGS. 12A-E: Fatty acid supplementation of growth inhibited cells. Growth of E. coli DP10 expressing MevT gene constructs with and without fatty acid supplementation. Where indicated, the medium was supplemented with 100 µg/ml fatty acid in the presence of 400 µg/ml Brij 58. (A) Growth of non-supplemented cultures. Growth in supplemented and non-supplemented media of E. coli DP10 cells harboring: (B) pBad33MevT, (C) pMevT(C159A), (D) pHMGS, and (E) pHMGSR.

Although the addition of palmitic acid improved the growth of cells inhibited by HMG-CoA, the concentration added may have been too low to fully alleviate the deficiency. The addition of increasing concentration of 16:0 to E. coli DP10 cells containing pBad33MevT, pHMGS, or their inactive controls (pMevT(C159A) or pHMGS(C159A), respectively) was tested in larger scale baffled shake flasks. Defined C media containing 50 µg/ml chloramphenicol was supplemented with either 100 µg/ml or 200 µg/ml Palmitic acid (16:0) in the presence of 400 µg/ml Brij (Sigma) or not supplemented with any fatty acid. Starter cultures of DP10 harboring the mevalonate pathway constructs were inoculated from single colonies and incubated overnight at 37° C. in defined C medium supplemented with 0.06% glucose (to repress the $P_{BAD}$ promoters) and chloramphenicol (for plasmid selection). Overnight starter cultures were diluted to an $OD_{600}$ of 0.05 in fresh C medium, with or without fatty acid supplements, in baffled shake flasks, then incubated at 37° C. with continuous shaking and induced with the addition of 1.33 mM (0.02%) arabinose at an $OD_{600}$ of approximately 0.25. The optical density of the cultures was measured using a UV-Spectrophotometer (Beckman).

Figure 13B:
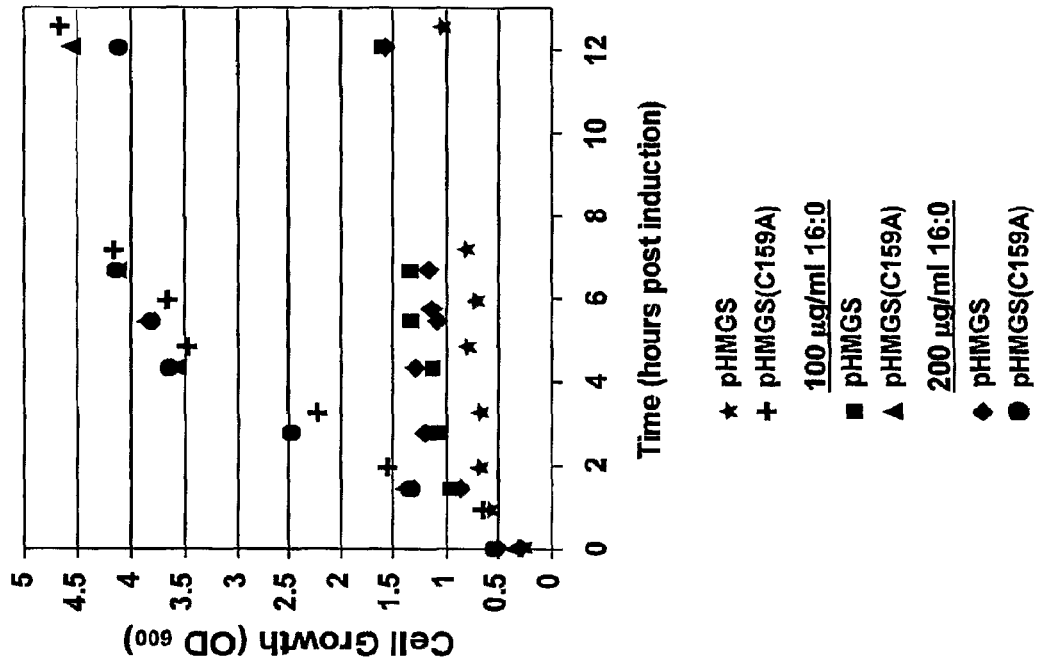
FIGS. 13A and 13B depict cell growth with increased supplementation of saturated fatty acid 16:0.
Figure 13A:
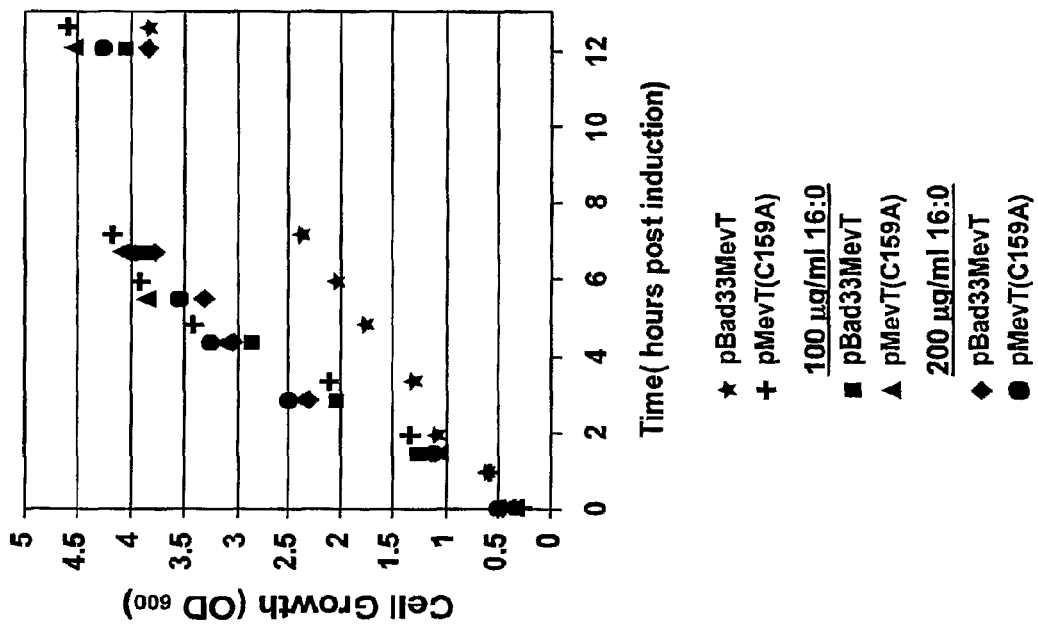

With increased aeration in baffled shake flakes, the addition of 100 µg/ml 16:0 to cell culture completely alleviated the growth inhibition caused by high expression of the MevT operon in E. coli, while only improving the growth of cells expressing HMGS alone (FIGS. 13A and 13B). Cell growth of the inactive pathway controls (DP10 harboring either pMevT(C159A) or pHMGS(C159A)) was not affected by the addition of 100 or 200 µg/ml palmitic acid. Increasing the concentration of 16:0 above 100 µg/ml had no additional effect on cell growth; however, the palmitic acid was not fully soluble in the in the aqueous media at the higher concentration. Although the addition of 16:0 didn't completely alleviate the growth inhibition of cells harboring pHMGS it did improve cell growth. As shown above, cells expressing HMGS quickly accumulated HMG-CoA and high levels of malonyl-CoA (up to 74% of measured acyl-CoAs) at the expense of both acetyl-CoA and free coenzyme A. By addition of 16:0, the strain may have been able to synthesize the required lipids; however, with the majority of coenzyme A locked in the form of malonyl-CoA, the cell may have also suffered from free coenzyme A deficiency (Jackowski and Rock. *J Bacteriol* 166, 866-871 (1986)). Altogether, the results of fatty acid supplementation strongly support the hypothesis that HMG-CoA is inhibiting fatty acid biosynthesis, likely by inhibiting the action of FabD.

FIGS. 13A and 13B. Cell growth with increased supplementation of saturated fatty acid 16:0. Growth of engineered cells with 100 µg/ml and 200 µg/ml 16:0. (A) DP10 containing pBad33MevT or pMevT(C159A), and (B) DP10 containing pHMGS or pHMGS(C159A). Cultures were induced with 1.33 mM arabinose at an $OD_{600}$ of approximately 0.25.

Example 3

Alleviating Growth Inhibition and Enhancing Isoprenoid Production by Increasing Media Osmolarity Coincident with the inhibition of fatty acid synthesis, we have observed evidence in microarray studies that suggest alteration of the lipid membrane in cells experiencing HMG-CoA toxicity. As discussed above, a portion of the stress response in cells harboring pBad33MevT corresponds to osmotic stress and oxidative stress. By inhibiting proper lipid formation, the lipid membrane may be altered causing an interruption in the electron transport chain—a major source of peroxide.

To further test if cells inhibited by the accumulation of HMG-CoA are suffering from osmotic stress, cells harboring pBad33MevT or pBad33 (the empty vector control) were incubated and induced in Luria Broth (LB) media with low (0.5 g/L) and high (10 g/L) concentrations of NaCl. For low concentration NaCl media (low osmolarity media), Luria Broth from Sigma (St. Louis, Mo.) was used (composition: 0.5 g/L NaCl, 10 g/L Tryptone, 5 g/L Yeast extract). For high concentration NaCl media (high osmolarity media), LB Broth MILLER from EMD Chemicals (Gibbstown, N.J.) was used (composition: 10 g/L NaCl, 10 g/L Tryptone, 5 g/L Yeast extract). Both culture media were supplemented with 1% (wt/vol) glycerol and 50 µg/ml chloramphenicol. Starter cultures of DH10B harboring either pBad33MevT or pBad33 were inoculated from single colonies and incubated overnight at 37° C. in LB media supplemented with 0.06% glucose (to repress the $P_{BAD}$ promoter) and chloramphenicol. Overnight starter cultures were diluted to an $OD_{600}$ of 0.05 in either the low or high NaCl media in baffled shake flasks, incubated at 37° C. with continuous shaking and induced with the addition of 2 mM arabinose at an $OD_{600}$ of approximately 0.39. The optical density of the culture was measured using a UV-Spectrophotometer (Beckman).

Figure 14:
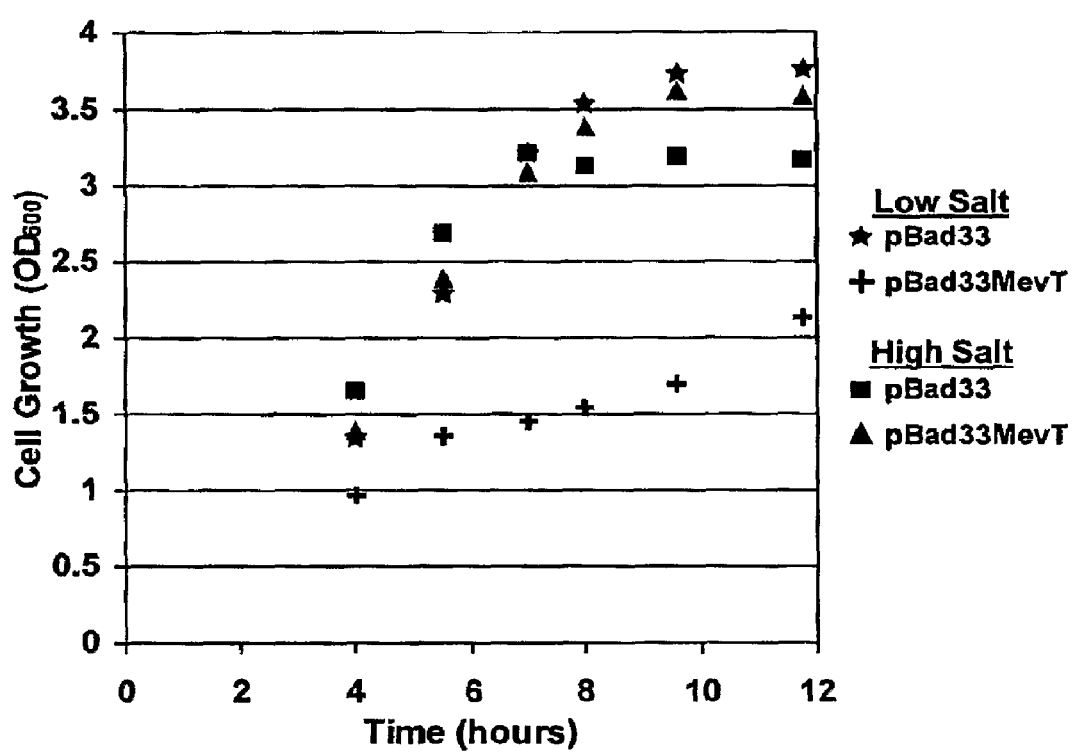
FIG. 14 depicts growth of HMG-CoA inhibited cells under high osmotic pressure.

Increasing salt concentration and thereby increasing the medium osmolarity effectively alleviated the growth inhibition of *E. coli* cells expressing the MevT operon from pBad33MevT (FIG. 14). Increasing medium osmolarity did not significantly affect the empty vector control strain (DH10B containing pBad33). The osmolality of the culture medium containing NaCl at a concentration of 10 g/L was determined to be about 452 mOsm/kg $H_2O$. The osmolality of the culture medium containing NaCl at a concentration of 0.5 g/L was determined to be about 125 mOsm/kg $H_2O$.

FIG. 16. Growth of HMG-CoA inhibited cells under high osmotic pressure. Growth of *E. coli* DH10B harboring pBad33MevT or pBad33 (empty vector control) in LB media containing 0.5 g/L NaCl (Low Salt) or 10 g/L NaCl (High Salt). Cell cultures were induced at an optical density of approximately 0.39.

By increasing the medium osmolarity, disruptions in the cell's lipid membrane may be compensated for. In studies of lipid membrane alterations caused by limited lipid biosynthesis, reports have demonstrated that increasing the osmolarity of the growth medium can compensate for inhibition of the early steps of fatty acid synthesis (Broekman and Steenbakkers. *J Bacteriol* 117, 971-977 (1974)). A minimal osmotic pressure of the medium appeared to be necessary to allow the growth of cells containing lipids with a changed fatty acid composition resulting from a fatty acid synthesis deficiency. The improved growth of HMG-CoA inhibited cells in higher osmolarity media directly supports our hypothesis that a block in fatty acid synthesis is altering the composition of the cell's lipid membrane.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A genetically modified prokaryotic host cell for the production of isoprenoids, wherein the host cell comprises an endogenous type II fatty acid biosynthetic pathway, and wherein the genetic modification comprises at least one nucleic acid encoding:
   i) a heterologous mevalonate pathway enzyme; and
   ii) a heterologous type II fatty acid biosynthetic enzyme, wherein said host cell exhibits reduced hydroxymethylglutaryl-CoA-mediated toxicity compared to a host cell that does not express the heterologous mevalonate pathway enzyme and the heterologous type II fatty acid biosynthetic enzyme.

2. The host cell of claim 1 wherein the host cell comprises all of the enzymes of the mevalonate pathway that convert acetyl-CoA to isopentenyl pyrophosphate.

3. The host cell of claim 1, wherein the at least one heterologous nucleic acid encodes acetoacetyl-CoA thiolase, hydroxymethylglutaryl-CoA synthase, hydroxymethylglutaryl-CoA reductase, mevalonate kinase, phosphomevalonate kinase, mevalonate pyrophosphate decarboxylase, isopentenyl pyrophosphate isomerase, and a prenyl transferase.

4. The host cell of claim 1 wherein the host cell is genetically modified with a plurality of heterologous nucleic acids that encode acetoacetyl-CoA thiolase, hydroxymethylglutaryl-CoA synthase, hydroxymethylglutaryl-CoA reductase, mevalonate kinase, phosphomevalonate kinase, mevalonate pyrophosphate decarboxylase, isopentenyl pyrophosphate isomerase, and a prenyl transferase.

5. The host cell of claim 1 wherein the type II fatty acid biosynthetic enzyme is an enzyme that converts malonyl-CoA to malonyl-ACP.

6. The host cell of claim 1 wherein the at least one heterologous nucleic acid encodes a plurality of type II fatty acid biosynthetic enzymes.

7. The host cell of claim 1 wherein the plurality of type II fatty acid biosynthetic enzymes includes an enzyme that converts malonyl-CoA to malonyl-ACP and an enzyme that converts acyl-ACP to β-ketoacyl-ACP.

8. The host cell of claim 7 wherein the plurality of type II fatty acid biosynthetic enzymes includes malonyl-CoA:ACP transferase and β-ketoacyl-ACP synthase I.

9. The host cell of claim 7 wherein the plurality of type II fatty acid biosynthetic enzymes includes FadD and FadB.

10. The host cell of claim 1, wherein the host cell is one that does not normally synthesize isopentenyl pyrophosphate via a mevalonate pathway.

11. The host cell of claim 1, wherein the host cell is *Escherichia coli*.

\* \* \* \* \*